(12) United States Patent
Scholefield et al.

(10) Patent No.: US 10,143,691 B2
(45) Date of Patent: Dec. 4, 2018

(54) PATHOGENIC CONTROL OF APOPTOSIS

(71) Applicant: CSIR, Pretoria (ZA)

(72) Inventors: Janine Scholefield, Johannesburg (ZA); Jerolen Naidoo, Pretoria (ZA); Musa M Mhlanga, Johannesburg (ZA); Samantha Barichievy, Gothenburg (SE)

(73) Assignee: CSIR, Pretoria (ZA)

( * ) Notice: Subject to any disclaimer, the term of this patent is extended or adjusted under 35 U.S.C. 154(b) by 0 days.

(21) Appl. No.: 15/503,610

(22) PCT Filed: Aug. 17, 2015

(86) PCT No.: PCT/IB2015/056247
§ 371 (c)(1),
(2) Date: Feb. 13, 2017

(87) PCT Pub. No.: WO2016/024257
PCT Pub. Date: Feb. 18, 2016

(65) Prior Publication Data
US 2017/0239248 A1    Aug. 24, 2017

(30) Foreign Application Priority Data

Aug. 15, 2014 (ZA) .................................. 2014/06021
Dec. 17, 2014 (ZA) .................................. 2014/09296

(51) Int. Cl.
*A61K 31/5025* (2006.01)
*A61K 38/17* (2006.01)
*A61K 31/277* (2006.01)
*A61K 31/497* (2006.01)
*A61K 31/496* (2006.01)

(52) U.S. Cl.
CPC ........ *A61K 31/5025* (2013.01); *A61K 31/277* (2013.01); *A61K 31/496* (2013.01); *A61K 31/497* (2013.01); *A61K 38/1709* (2013.01)

(58) Field of Classification Search
None
See application file for complete search history.

(56) References Cited

PUBLICATIONS

Huarte et al.,Cell, vol. 142, No. 3, Aug. 1, 2010, pp. 409-419.*
Dimitrova et al., Molecular Cell 54, 777-790, 2014.*
Busschots et al., Molecular Biosystems, vol. 5, No. 1, Jan. 1, 2009 pp. 21-31.*
International Search Report of International Patent Application No. PCT/IP2015/056247 dated Nov. 18, 2015.
Huarte, Malte et al., "A Large Intergenic Noncoding RNA Induced by p53 Mediates Global Gene Repression in the p53 Response", Cell, Aug. 1, 2010, pp. 409-419, vol. 142, No. 3.
Dimitrova, Nadya et al., "LincRNA-p21Activatesp21 Incisto Promote Polycomb Target Gene Expression and to Enforce the G1/S Checkpoint", Molecular Cell, Jun. 5, 2014, 777-790, vol. 54, No. 5.

(Continued)

*Primary Examiner* — Karl J Puttlitz
(74) *Attorney, Agent, or Firm* — McBee Moore Woodward & Vanik IP, LLC; Susan McBee

(57) ABSTRACT

The present invention relates to methods and compositions for modulating the control of apoptosis, specifically for modulating the interaction between hnRNP-K and lincRNA-p21 to induce or prevent apoptosis in the cell.

5 Claims, 40 Drawing Sheets

Specification includes a Sequence Listing.

(56) References Cited

PUBLICATIONS

Busschots, Katrien et al., "In search of small molecules blocking interactions between HIV proteins and intracellularcofactors", Molecular Biosystems, Jan. 1, 2009, pp. 21-31, vol. 5, No. 1.
Gong, Jian et al., "Down-regulation of HIV-1 infection by inhibition of the MAPK signaling pathway", Virologica Sinica, SP Wuhan Institute of Virology, CAS, Heidelberg, Apr. 7, 2011, pp. 114-122, vol. 26, No. 2.
Cooper, Arik, et al. "HIV-1 causes CD4 cell death through DNA-dependent protein kinase during viral integration." Nature 498.7454 (2013): 376.
Cummins, Nathan W., and Andrew D. Badley. "Anti-apoptotic mechanisms of HIV: lessons and novel approaches to curing HIV." Cellular and molecular life sciences 70.18 (2013): 3355-3363.
Fischer, April M., et al. "The role of erk1 and erk2 in multiple stages of T cell development." Immunity 23.4 (2005): 431-443.
Chang, Chiung-Fang, et al. "Polar opposites: Erk direction of CD4 T cell subsets." The Journal of Immunology 189.2 (2012): 721-731.
Chang, Lufen, and Michael Karin. "Mammalian MAP kinase signalling cascades." Nature 410.6824 (2001): 37.
Swingler, Simon, et al. "Apoptotic killing of HIV-1-infected macrophages is subverted by the viral envelope glycoprotein." PLoS pathogens 3.9 (2007): e134.

\* cited by examiner

PATHOGENIC CONTROL OF APOPTOSIS

CROSS-REFERENCE TO RELATED APPLICATIONS

This application is a National Stage entry of International Application No. PCT/IB2015/056247, filed Aug. 17, 2015, which claims priority to South African Patent Application No. 2014/06021, filed Aug. 15, 2014 and South African Patent Application No. 2014/09296, filed Dec. 17, 2014.

BACKGROUND OF THE INVENTION

Field of the Invention

The present invention relates to methods and compositions for modulating the control of apoptosis, specifically for modulating the interaction between hnRNP-K and lincRNA-p21 to induce or prevent apoptosis in the cell.

Description of Related Art

Research of apoptosis has increased substantially since the early 1990s due to its importance as a biological phenomenon as well as its role in a wide variety of diseases. Excessive apoptosis causes atrophy and can lead to neurodegenerative diseases, hematologic diseases, and tissue damage, whereas an insufficient amount of apoptosis results in uncontrolled cell proliferation, such as cancer.

The Human Immunodeficiency Virus type 1 (HIV-1) induces cytopathic effects and apoptosis in CD4+ T cells but is largely non-cytopathic in macrophages, thereby leading to long-term dissemination of the pathogen via macrophages. Pathogen-mediated apoptosis is triggered by double-strand breaks (DSBs), such as those induced by integrating retroviruses. Interestingly, HIV-1 induces such DSBs in macrophages but avoids instigating apoptosis in these cells.

Thousands of deliberate as well as unplanned DNA DSBs occur daily in human cells. Such defects can be deleterious, and a complex network that integrates DNA damage signalling and repair exists. DSBs can be lethal because there is no intact complementary strand to serve as a template for repair. DNA viruses can exist episomally but retroviruses must induce a DSB in host chromatin to integrate a DNA copy of their proviral genome following viral-mediated reverse transcription. As infecting retroviruses cannot coordinate the number of integration events and consequent DSBs per host cell, these viruses appear to have evolved mechanisms to suppress activation of proapoptotic genes. The p53 tumour suppressor protein is a core DNA damage transcription factor which plays a central role in the response to DNA damage with its activation leading to apoptosis, senescence or cell-cycle arrest. p53 induces these responses by regulating prosurvival factors such as CDKN1A/p21, as well as several proapoptotic proteins. In particular, p53 induces the long noncoding RNA lincRNA-p21 which coordinates apoptosis in a complex with its protein-binding partners (Huarte et al 2010).

The progressive decline of CD4+ T cells during HIV-1 infection is a hallmark of the disease. This is driven in part by viral integrase-mediated apoptosis (Cooper et al 2013) although abortive infection leading to pyroptosis accounts for the majority of death in these cells. Macrophages are permissive to HIV-1 infection but are largely spared the cytopathic effects of replicating virus, suggesting a selective impairment of the apoptotic response in these cells (Cummins and Badley 2013). Several viruses, including HIV-1 (Swingler et al 2013), can prevent apoptosis induced by TNF-related apoptosis-inducing ligand (TRAIL) in macrophages, but the fundamental molecular mechanism has heretofore remained unknown.

In a nuclear complex with its protein binding partner hnRNP-K, lincRNA-p21 orchestrates the apoptotic trigger by allowing for proper genomic localisation of hnRNP-K to specifically repress the transcription of prosurvival p53 target genes in the nucleus (Huarte et al 2010).

One important target of this complex is MAP2K1 which phosphorylates ERK2 to maintain a cellular survival cascade (Chang and Karin 2001). Activated ERK2 associates with the HIV-1 pre-integration complex (PIC) to facilitate successful integration in macrophages. JNK and Pin1 facilitate HIV-1 integration in activated CD4+ T cells, possibly as ERK2 expression is shut down in these cells following differentiation (Fischer et al 2005, Chang et al 2012) and is thus unavailable for viral use.

It has been observed that Adenovirus onco-proteins are able to inactivate the DNA repair MRN complex at viral replication centers, masking host genome instabilities that are instigated by this generally non-integrative DNA virus. Furthermore, the phosphorylation of p53 at key residues, required to ensure its stabilisation as well as to facilitate DNA binding, is also inhibited in adenovirus-infected cells. Intriguingly, in the presence of exogenous genotoxic stress, p53 was phosphorylated at multiple residues and thus stabilised to a greater extent than untreated cells, but the presence of adenovirus ensured that p53 failed to activate downstream transcription. As the constitutive expression of p53 in the absence of DNA damage is controlled through HDM2-mediated degradation, the phosphorylation of p53 is synonymous with its resistance to such degradation and transcription of downstream effectors. Given that viruses contribute to 20% of cancers worldwide, it is important to understand how genomic instabilities are propagated following challenge, as well as how apoptosis is evaded.

The results presented herein provide insights into pathogenic control of apoptosis and DNA damage via host long non-coding RNAs involved in regulating cellular survival, and present a potential therapeutic intervention strategy for HIV-1 infection and cancers related to viral infections.

SUMMARY OF THE INVENTION

The present invention provides for a method of modulating apoptosis in a cell, said method comprising modulating the interaction between hnRNP-K and lincRNA-p21 to induce apoptosis in the cell.

According to a first aspect of the invention there is provided for a method for modulating apoptosis in a cell infected with a retrovirus, the method comprising elevating levels of full-length lincRNA-p21 in the cell and inducing localisation of hnRNP-K to the nucleus of the cell wherein in response to a double stranded break in the cell's DNA, caused by the infection with the retrovirus, lincRNA-p21 associates with hnRNP-K in the nucleus and induces apoptosis in the cell.

In one embodiment of the invention the retrovirus is Human Immunodeficiency Virus.

In one embodiment of the invention the levels of lincRNA-p21 in the cell are elevated by either activating the transcription of lincRNA-p21 in the cell or by transfecting the cell with full-length lincRNAp21. It will be appreciated that the transcription of lincRNA-p21 may be upregulated by promoting transcription of lincRNA-p21 by any method known to those of skill in the art. In an alternative embodiment lincRNA-p21 may be introduced into the cell by transfection.

In another embodiment of the invention localisation of hnRNP-K to the nucleus of the cell may be induced by inhibiting either HDM2, MAP2K1 or ERK2 activity in the cell.

It will be appreciated that (−)-4-(4,5-Bis(4-chlorophenyl)-2-(2-isopropoxy-4-methoxyphenyl)-4,5-dihydro-1H-imidazole-1-carbonyl)piperazin-2-one, binds to and inhibits HDM2. It will further be appreciated that 1,4-diamino-2,3-dicyano-1,4-bis(2-aminophenylthio)butadiene, and wherein the binds to and inhibits MAP2K1. It will also be appreciated that 5-(2-phenylpyrazolo[1,5-a]pyridin-3-yl)-1H-pyrazolo[3,4-c]pyridazin-3-amine, binds to and inhibits ERK2.

In one embodiment of the invention the inhibition of HDM2 by the inhibitor results in the release of the negative regulation of hnRNP-K, which induces localisation of hnRNP-K to the nucleus thus allowing hnRNP-K to associate with lincRNA-p21 and thus activate the apoptotic pathway.

In another embodiment of the invention the inhibition of MAP2K1 by the inhibitor leads to the inhibition of ERK2 resulting in the release of the negative regulation hnRNP-K, and which induces localisation of hnRNP-K to the nucleus thus allowing hnRNP-K to associate with lincRNA-p21 and thus activate the apoptotic pathway.

In yet another embodiment of the invention the inhibition of ERK2 by the inhibitor leads to the release of the negative regulation of hnRNP-K, which induces localisation of hnRNP-K to the nucleus thus allowing hnRNP-K to associate with lincRNA-p21 and thus activate the apoptotic pathway.

In a second aspect of the invention there is provided for an inhibitor of HDM2, MAP2K1 or ERK2 for use in modulating apoptosis in a cell infected with a retrovirus, wherein the inhibitor induces localisation of hnRNP-K to the nucleus, and wherein in response to a double stranded break in the cell's DNA caused by the infection with the retrovirus, lincRNA-p21 associates with hnRNP-K in the nucleus and induces apoptosis in the cell.

In one embodiment of the invention the inhibitor is (−)-4-(4,5-Bis(4-chlorophenyl)-2-(2-isopropoxy-4-methoxyphenyl)-4,5-dihydro-1H-imidazole-1-carbonyl) piperazin-2-one, and the inhibitor binds to and inhibits HDM2.

In another embodiment of the invention the inhibitor is 1,4-diamino-2,3-dicyano-1,4-bis(2-aminophenylthio)butadiene, and the inhibitor binds to and inhibits MAP2K1.

In yet another embodiment of the invention the inhibitor is 5-(2-phenylpyrazolo[1,5-a]pyridin-3-yl)-1H-pyrazolo[3,4-c]pyridazin-3-amine, and the inhibitor-amine binds to and inhibits ERK2.

In one embodiment of the invention the inhibitor results in inhibition of HDM2. The inhibition of HDM2 by the inhibitor results in the release of the negative regulation of hnRNP-K, this induces localisation of hnRNP-K to the nucleus, allowing hnRNP-K to associate with lincRNA-p21 and thus activate the apoptotic pathway.

In another embodiment of the invention the inhibitor results in inhibition of MaP2K1. The inhibition of MAP2K1 by the inhibitor further leads to the inhibition of ERK2 resulting in the release of ERK2's negative regulation of hnRNP-K and which induces localisation of hnRNP-K to the nucleus, allowing hnRNP-K to associate with lincRNA-p21 and thus activate the apoptotic pathway.

In one embodiment of the invention the inhibitor results in inhibition of HDM2. The inhibition of ERK2 by the inhibitor results in the release of the negative regulation of hnRNP-K, this induces localisation of hnRNP-K to the nucleus, allowing hnRNP-K to associate with lincRNA-p21 and thus activate the apoptotic pathway.

It will be appreciated that release of the negative regulation of hnRNP-K by inhibiting HDM2, MAP2K1 or ERK2 leads to localisation of hnRNP-K to the nucleus. In order to stimulate apoptosis lincRNA-p21 levels may be artificially increased in the nucleus by upregulating the transcription of lincRNA-p21 by any method known to those of skill in the art. In an alternative embodiment lincRNA-p21 levels may be elevated by introducing lincRNA-p21 into the cell by transfection.

BRIEF DESCRIPTION OF THE DRAWINGS

Non-limiting embodiments of the invention will now be described by way of example only and with reference to the following figures.

HIV1 integration occurs approximately 16 hours post-infection of Ghost(3) reporter cells and Tat-mediated activation of an integrated LTR-driven GFP reporter can be detected approximately 48 hours post-infection.

Figure 2:
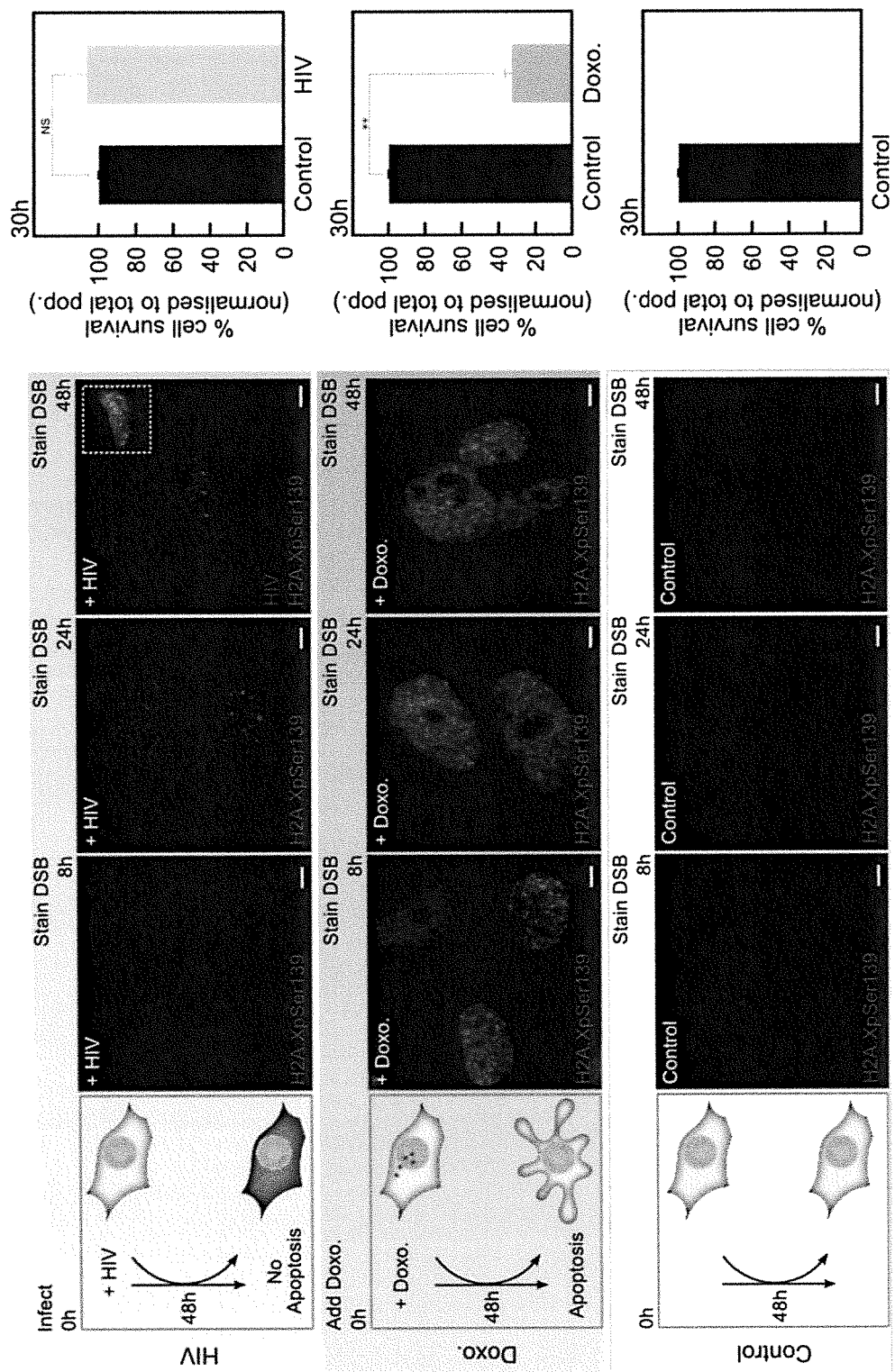

FIG. 2: HIV1 induces DSBs during integration but evades cellular apoptosis by masking DNA damage HIV1 infection of Ghost(3) cells induces DSBs over 48 hours as detected by H2A.XpSer139 immunofluorescence staining but does not lead to caspase 3-mediated apoptosis (displayed as percentage cell survival; n=3000). Doxorubicin treatment (Doxo.) over the same time course yields extensive H2A.XpSer139 staining followed by apoptosis.

Figure 3:
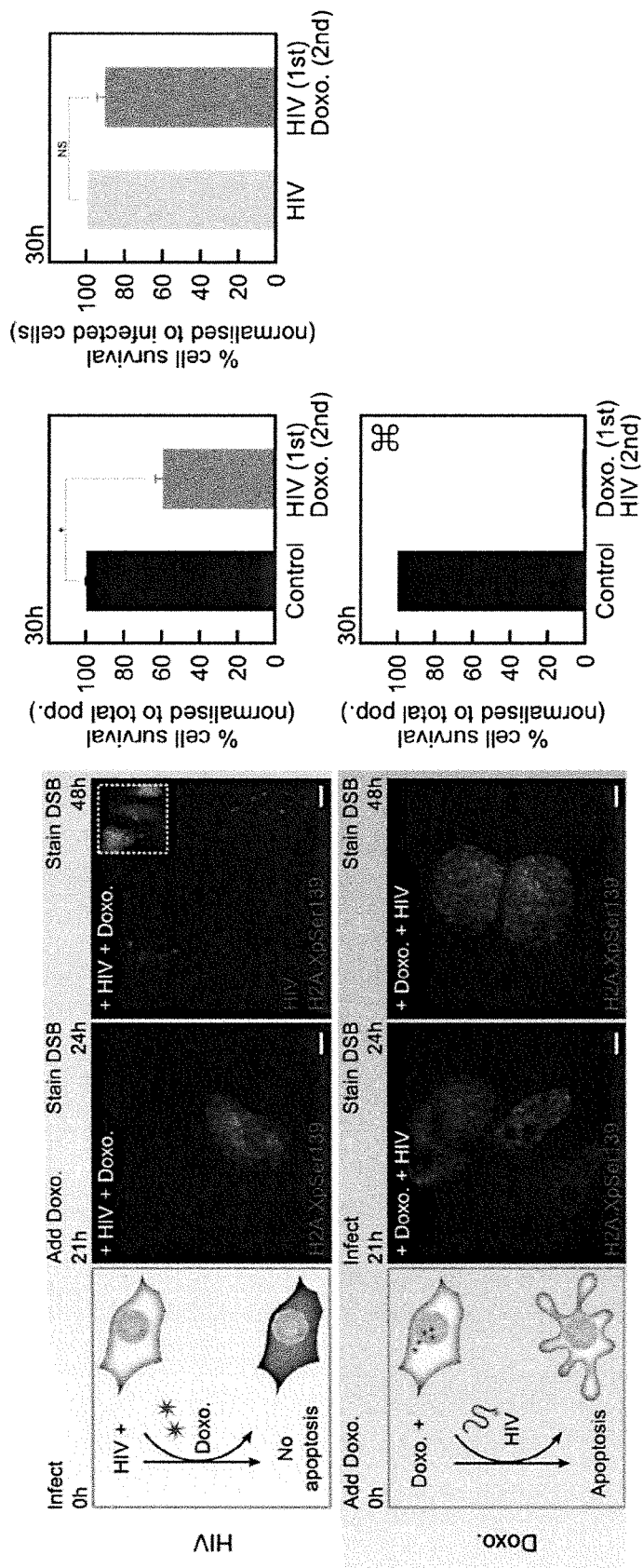

FIG. 3: HIV1 induces DSBs during integration but evades cellular apoptosis by masking DNA damage HIV1 infection protects against additional lethal DNA damage. Ghost(3) cells infected 24 hours prior to Doxorubicin treatment (+HIV+Doxo.) have numerous DSBs but do not undergo apoptosis when normalised to infected cells (HIV (1st) Doxo. (2nd); orange bars). Cells infected after exposure to Doxorubicin (+Doxo.+HIV) have extensive H2A.XpSer139 staining and do undergo apoptosis. ⌘ Too few attached cells (<20) were present for statistical analysis.

Figure 4:
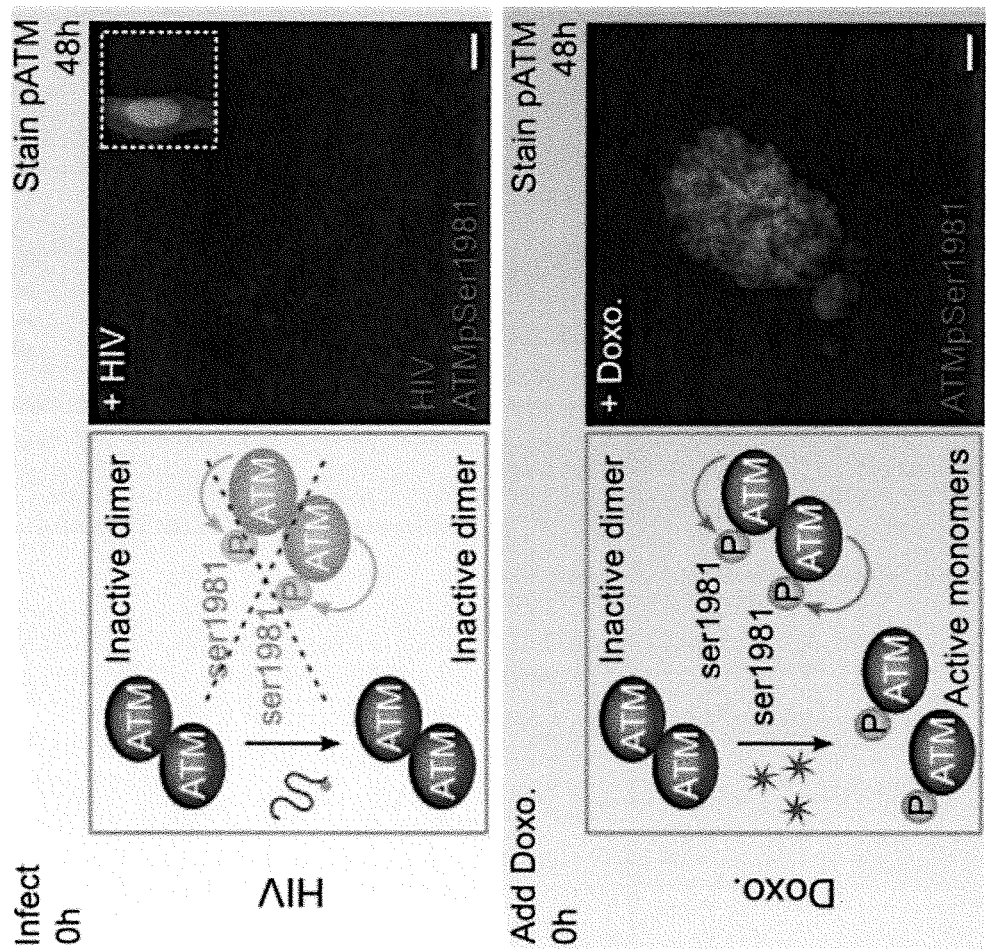

FIG. 4: HIV1 induces DSBs during integration but evades cellular apoptosis by masking DNA damage ATM is not activated in response to HIV1 infection. Inactive ATM dimers do not undergo auto-phosphorylation of serine residue 1981 in response to HIV-induced DSBs as measured by immunofluorescence staining (ATMpSer1981) in Ghost(3) cells. Phosphorylated ATM is detected in Doxorubicin-treated cells.

Figure 5:
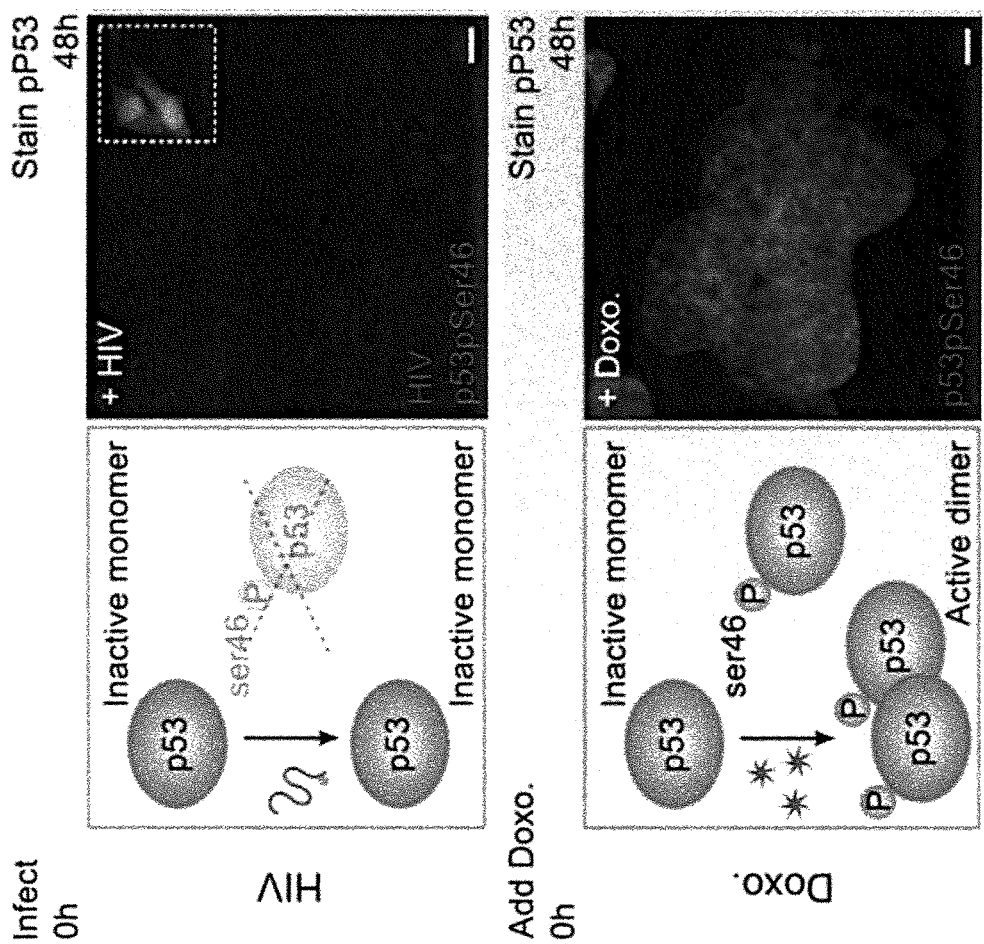

FIG. 5: HIV1 induces DSBs during integration but evades cellular apoptosis by masking DNA damage The apoptotic mark on p53 is not activated in HIV-infected cells. Inactive p53 monomers are not phosphorylated at serine residue 46 in response to HIV1 infection of Ghost(3) cells as measured by immunofluorescence staining (p53pSer46). Activated p53 dimers are detected in Doxorubicin-treated cells.

Figure 6:
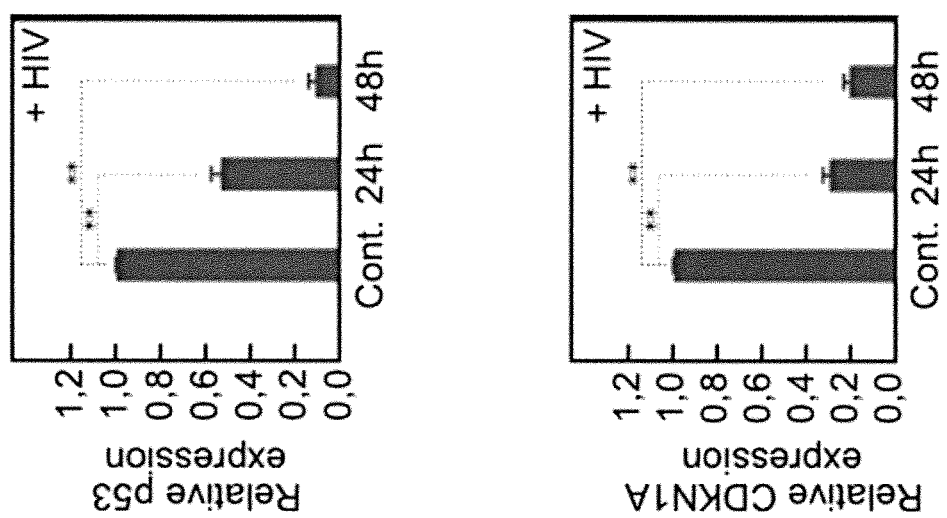

FIG. 6: HIV1 induces DSBs during integration but evades cellular apoptosis by masking DNA damage HIV1 infection significantly decreases p53 and CDKN1A/p21 expression over time relative to HPRT housekeeping gene. Quantitative real-time RTPCR analysis of HIV-infected Ghost(3) cells normalised to uninfected cells (mean±SD of 3 biological replicates). Cells were counterstained with DAPI; Scale bars=10 μM; Two-tailed paired Student T-test, *p<0.001, p<0.01, *p<0.05, NS (not significant).

Figure 7:
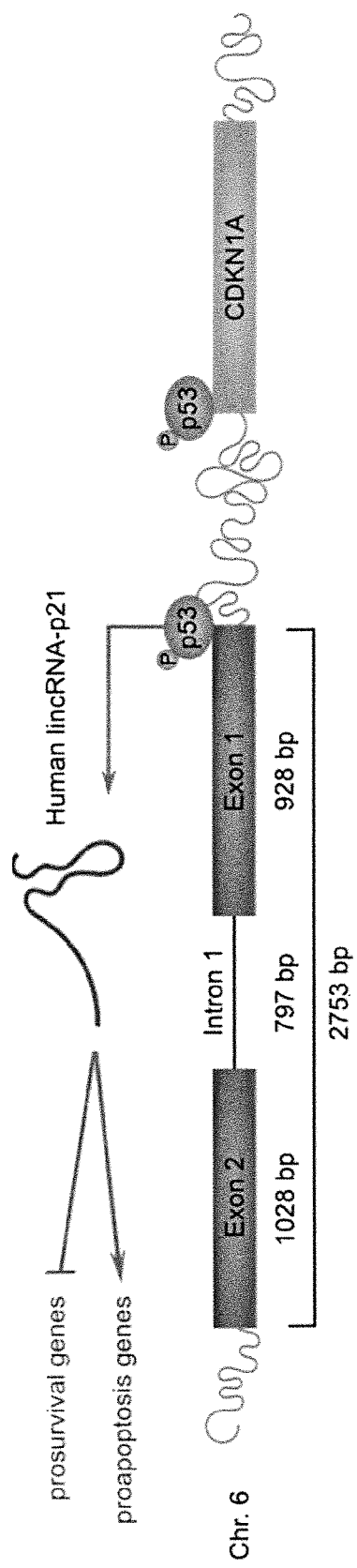

FIG. 7: HIV1 infection prevents enhanced lincRNAp21 expression by sequestering HuR in the nucleus Human lincRNAp21, which is located upstream of CDKN1A/p21 on chromosome 6 and comprised of 2 exons and a single intron, is transcribed by p53 in response to DNA damage. LincRNAp21 mediates cellular apoptosis by down-regulating prosurvival genes and upregulating proapoptosis genes FIG. 8: HIV1 infection prevents enhanced lincRNAp21 expression by sequestering HuR in the nucleus HIV1 infection does not lead to enhanced lincRNAp21 expression. Doxorubicin-induced (Doxo.) DNA damage significantly increases lincRNAp21 expression over time as compared to HIV-infected and untreated control in Ghost(3) cells as measured by RNA FISH spot counts and represented in a box and whisker plot. n, number of nuclei (n=903; ~100 nuclei per treatment). Notably, smFISH lincRNAp21 spot count analysis at 48 hours of Doxorubicin-treated cells is reduced due to the high number of dead cells.

Figure 9:
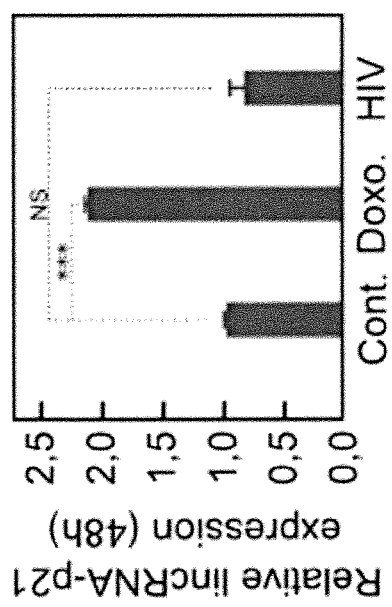

FIG. 9: HIV1 infection prevents enhanced lincRNAp21 expression by sequestering HuR in the nucleus HIV-induced DNA damage does not lead to enhanced lincRNAp21 expression. Quantitative real-time RTPCR analysis of lincRNAp21 expression at 48 hours relative to HPRT housekeeping gene in Doxorubicin-treated (Doxo.) and infected Ghost(3) cells normalised to untreated cells (mean±SD of 3 biological replicates).

Figure 10:
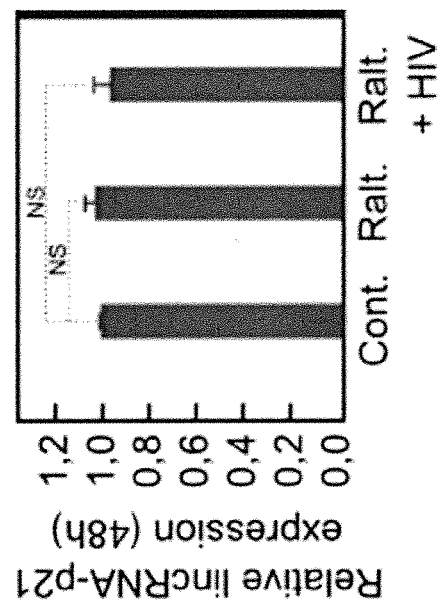

FIG. 10: HIV1 infection prevents enhanced lincRNAp21 expression by sequestering HuR in the nucleus Raltegravir (Ralt.) does not affect lincRNAp21 expression. Quantitative real-time RTPCR analysis of lincRNAp21 expression at 48 hours relative to HPRT housekeeping gene in infected Ghost(3) cells normalised to uninfected cells (mean±SD of 3 biological replicates).

Figure 11:
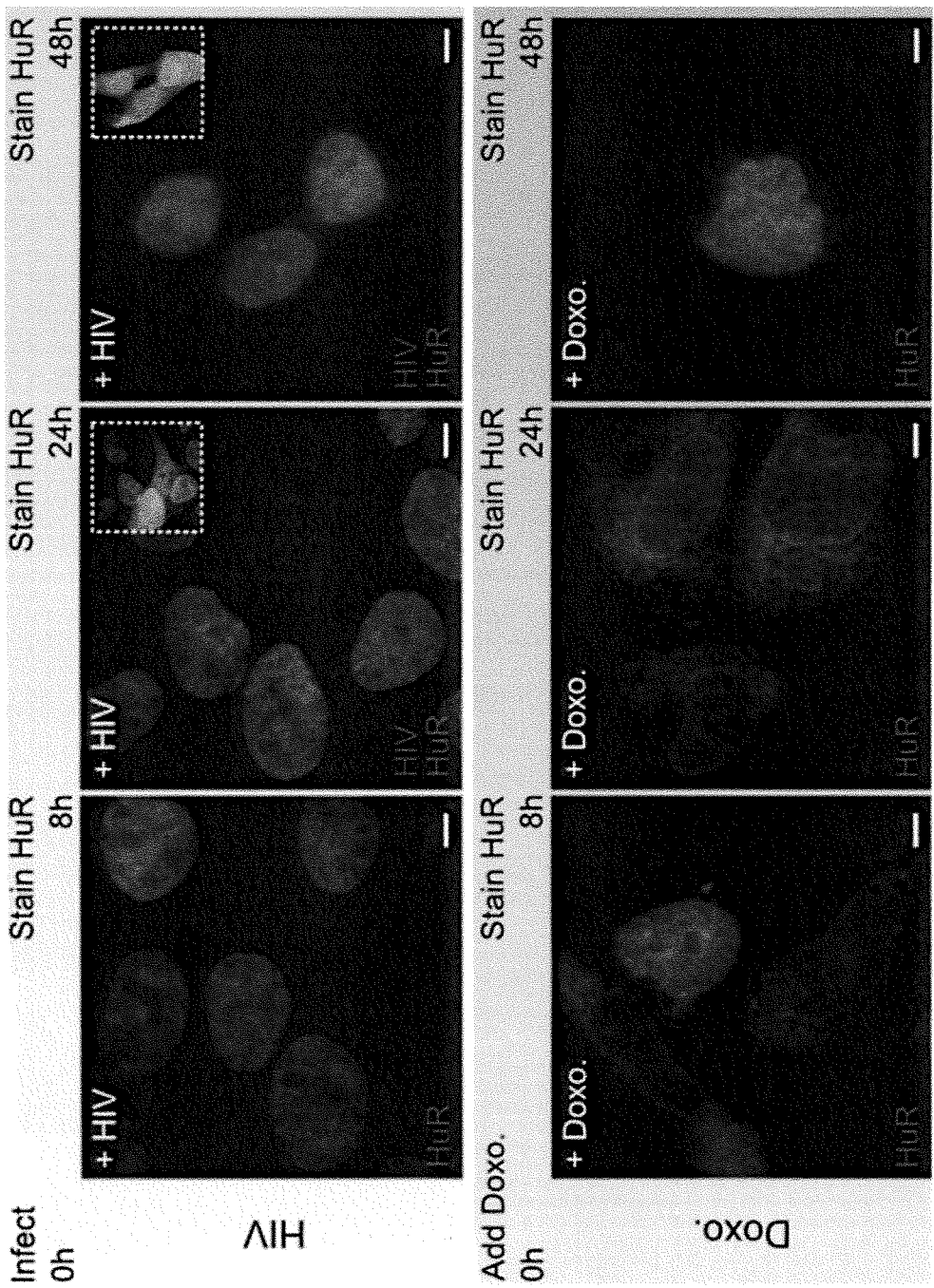

FIG. 11: HIV1 infection prevents enhanced lincRNAp21 expression by sequestering HuR in the nucleus HIV1 prevents cytoplasmic location of HuR. Immuno-fluorescence staining reveals cytoplasmic HuR within 8 hours of Doxorubicin-treated (Doxo.) Ghost(3) cells while HIV-infected cells show nuclear HuR up until 48 hours.

Figure 12:
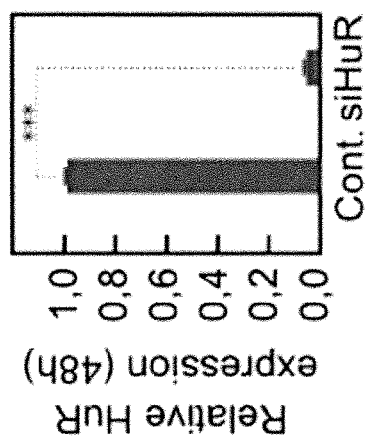

FIG. 12: HIV1 infection prevents enhanced lincRNAp21 expression by sequestering HuR in the nucleus HuR expression is significantly decreased following 48 hours of exposure to siHuR in Ghost(3) cells.

Figure 13:
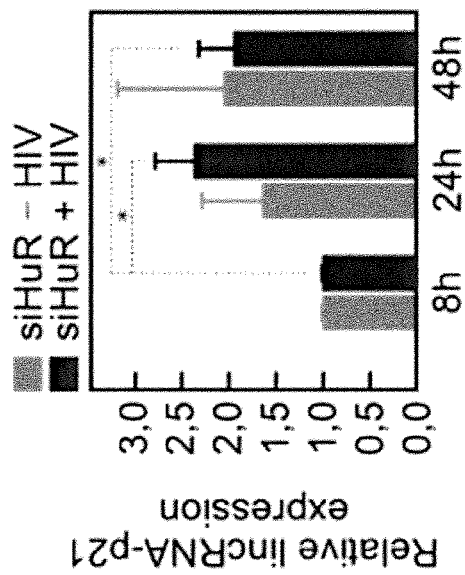

FIG. 13: HIV1 infection prevents enhanced lincRNAp21 expression by sequestering HuR in the nucleus LincRNAp21 expression increases in the absence of HuR. Quantitative real-time RTPCR analysis of lincRNAp21 expression over time relative to HPRT housekeeping gene in HIV-infected and uninfected Ghost(3) cells treated for 48 hours prior to infection with an siRNA targeted to HuR (mean±SD of 3 biological replicates).

Figure 14:
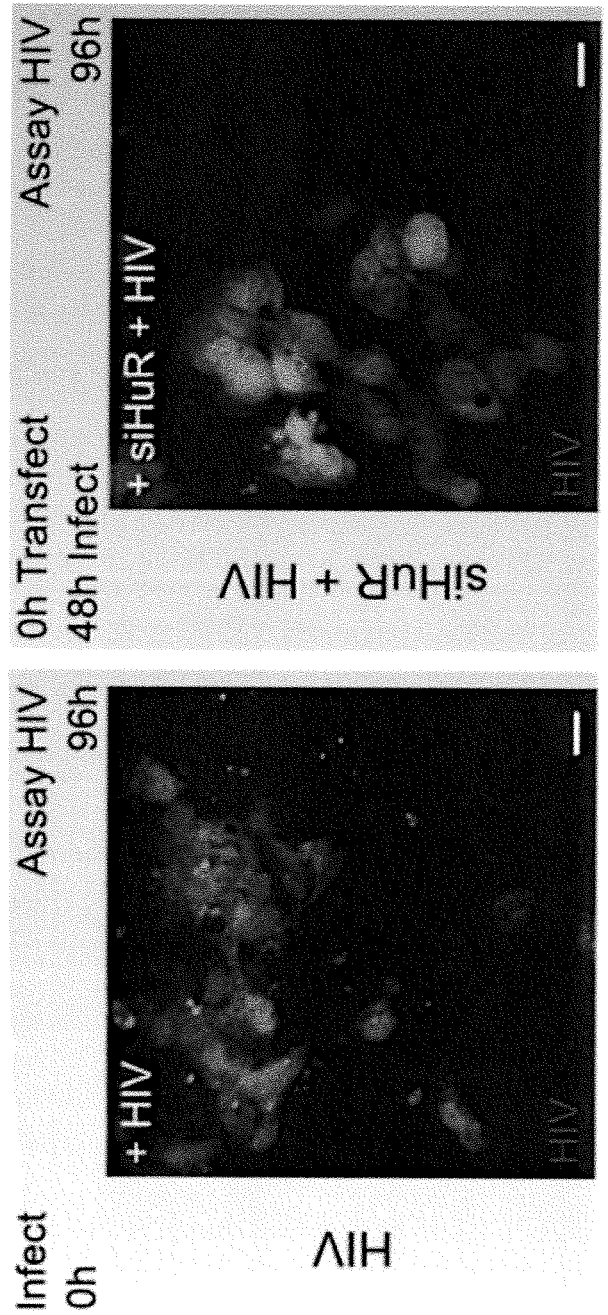

FIG. 14: HIV1 infection prevents enhanced lincRNAp21 expression by sequestering HuR in the nucleus siHuR-treated cells support HIV1 replication to the same extent as untreated cells. Ghost(3) cells transfected with siHuR 48 hours prior to infection for 48 hours support HIV1 replication to the same extent as untransfected cells, as indicated by GFP expression. Scale bar=5 μM.

Figure 15:
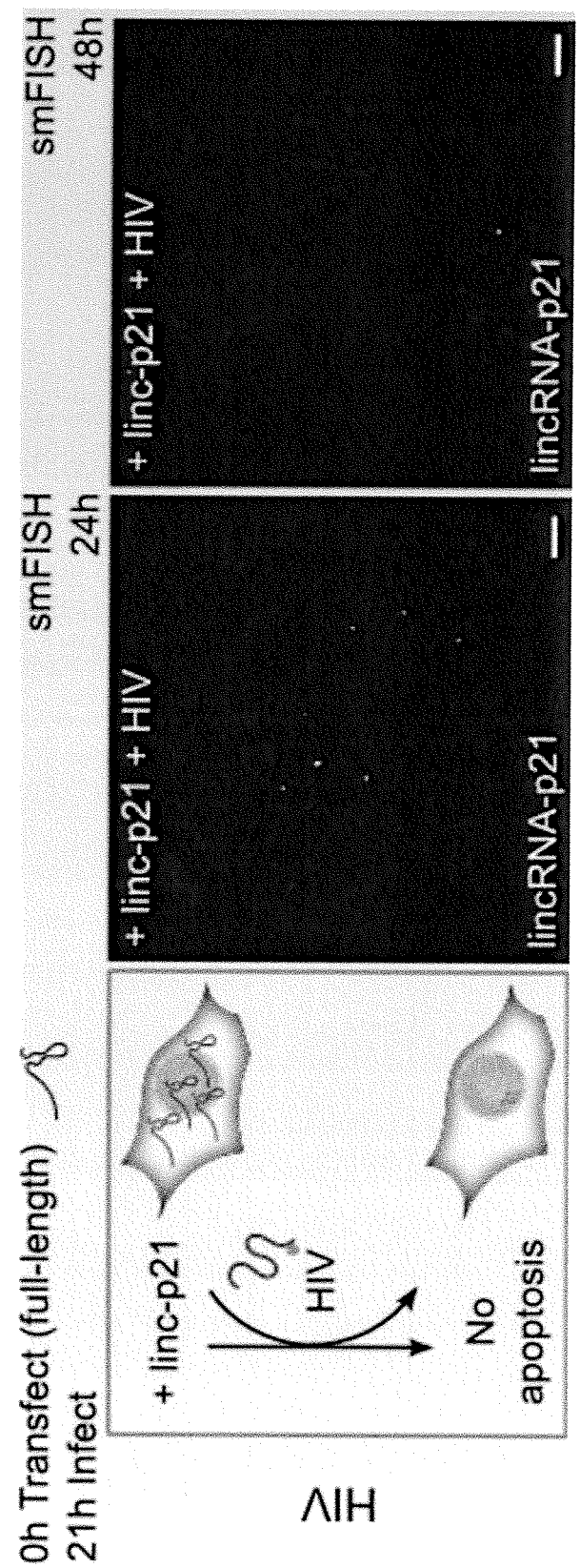

FIG. 15: HIV1 infection prevents enhanced lincRNAp21 expression by sequestering HuR in the nucleus Exogenous full-length lincRNAp21 expression is reduced in HIV-infected cells. CMVdriven full-length lincRNAp21 transfected 24 hours prior to HIV1 infection of Ghost(3) cells detected by RNA FISH over time.

Figure 16:
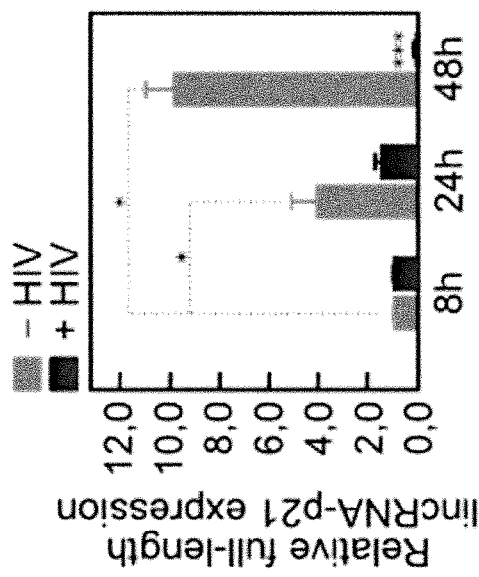

FIG. 16: HIV1 infection prevents enhanced lincRNAp21 expression by sequestering HuR in the nucleus Exogenous full-length lincRNAp21 expression is reduced in HIV-infected cells. Quantitative real-time RTPCR analysis of lincRNAp21 expression over time relative to HPRT housekeeping gene in HIV-infected and uninfected Ghost(3) cells (mean±SD of 3 biological replicates). Cells were counterstained with DAPI; Scale bars=10 μM; Two-tailed paired Student T-test, *p<0.001, p<0.01, *p<0.05, NS (not significant).

Figure 17:
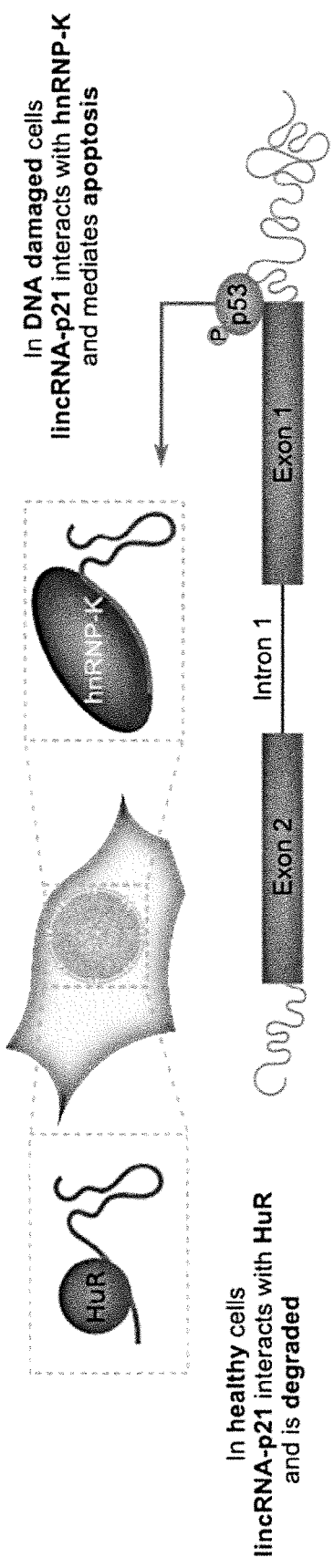

FIG. 17: HIV1 prevents nuclear localisation of lincRNAp21 protein binding partner hnRNPK In healthy cells, lincRNAp21 associates with HuR and is degraded. In response to p53-mediated transcription, lincRNAp21 associates with hnRNPK in the nucleus of DNA-damaged cells and regulates apoptosis by localising hnRNPK to the promoters of p53 repressed genes.

Figure 18:
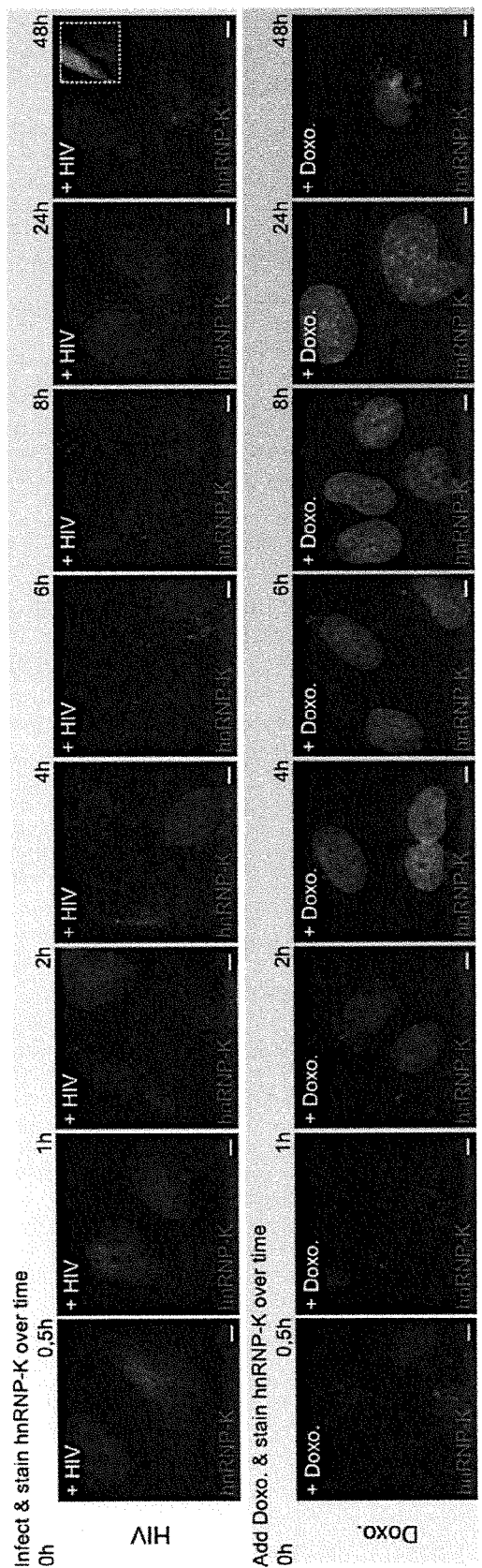

FIG. 18: HIV1 prevents nuclear localisation of lincRNAp21 protein binding partner hnRNPK HIV1 prevents nuclear localisation of hnRNPK. Immuno-fluorescence staining reveals nuclear hnRNPK within 2 hours of Doxorubicin-treated (Doxo.) Ghost(3) cells while HIV-infected cells show cytoplasmic hnRNPK throughout all 8 time points spanning the same 48 hour time course.

Figure 19:
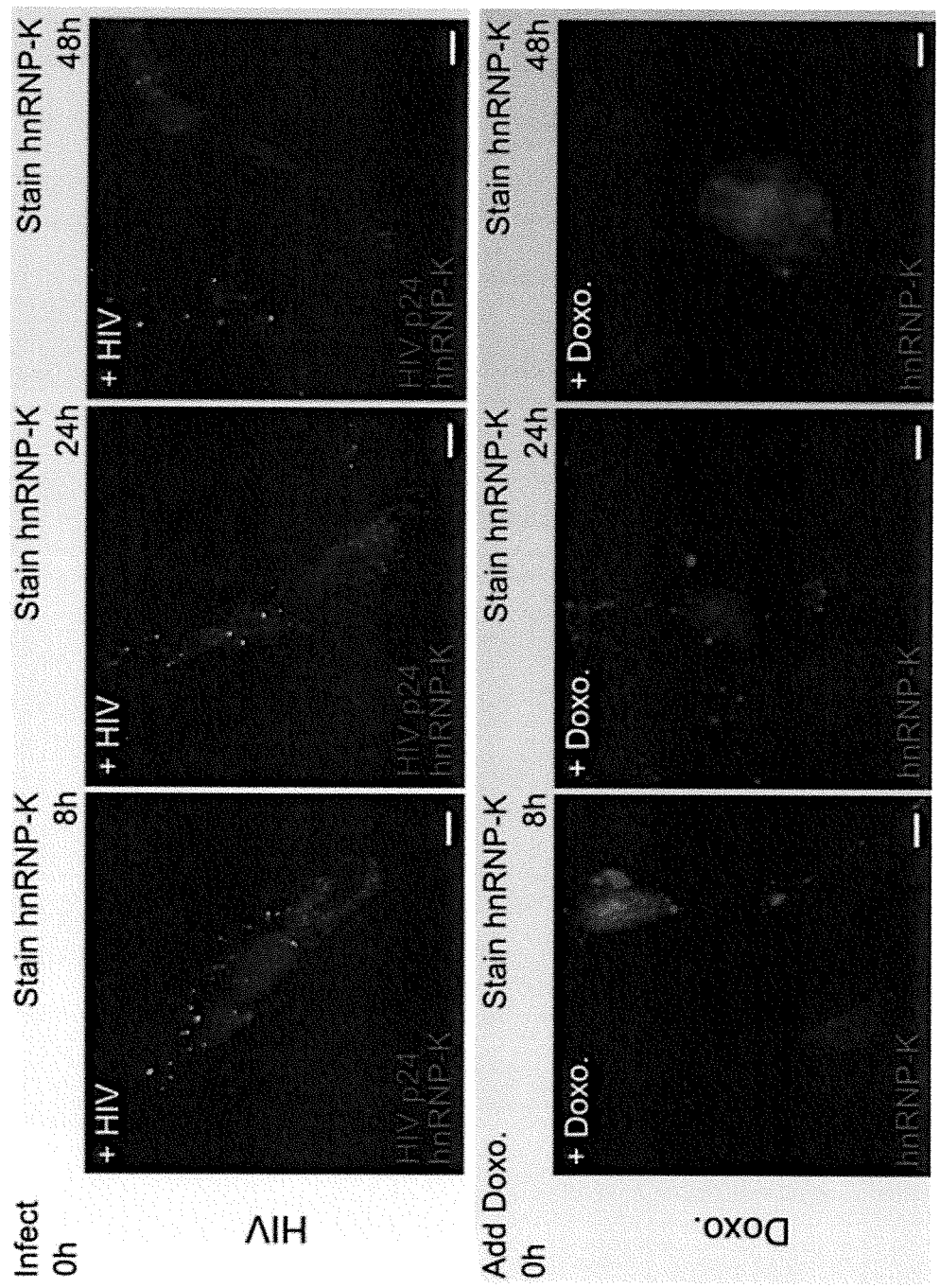

FIG. 19: HIV1 prevents nuclear localisation of lincRNAp21 protein binding partner hnRNPK HIV1 prevents nuclear localisation of hnRNPK. Immuno-fluorescence staining reveals nuclear hnRNPK within 8 hours of Doxorubicin-treated (Doxo.) primary macrophages while HIV-infected cells (p24 staining) show cytoplasmic hnRNPK throughout the same 48 hour time course.

Figure 20:
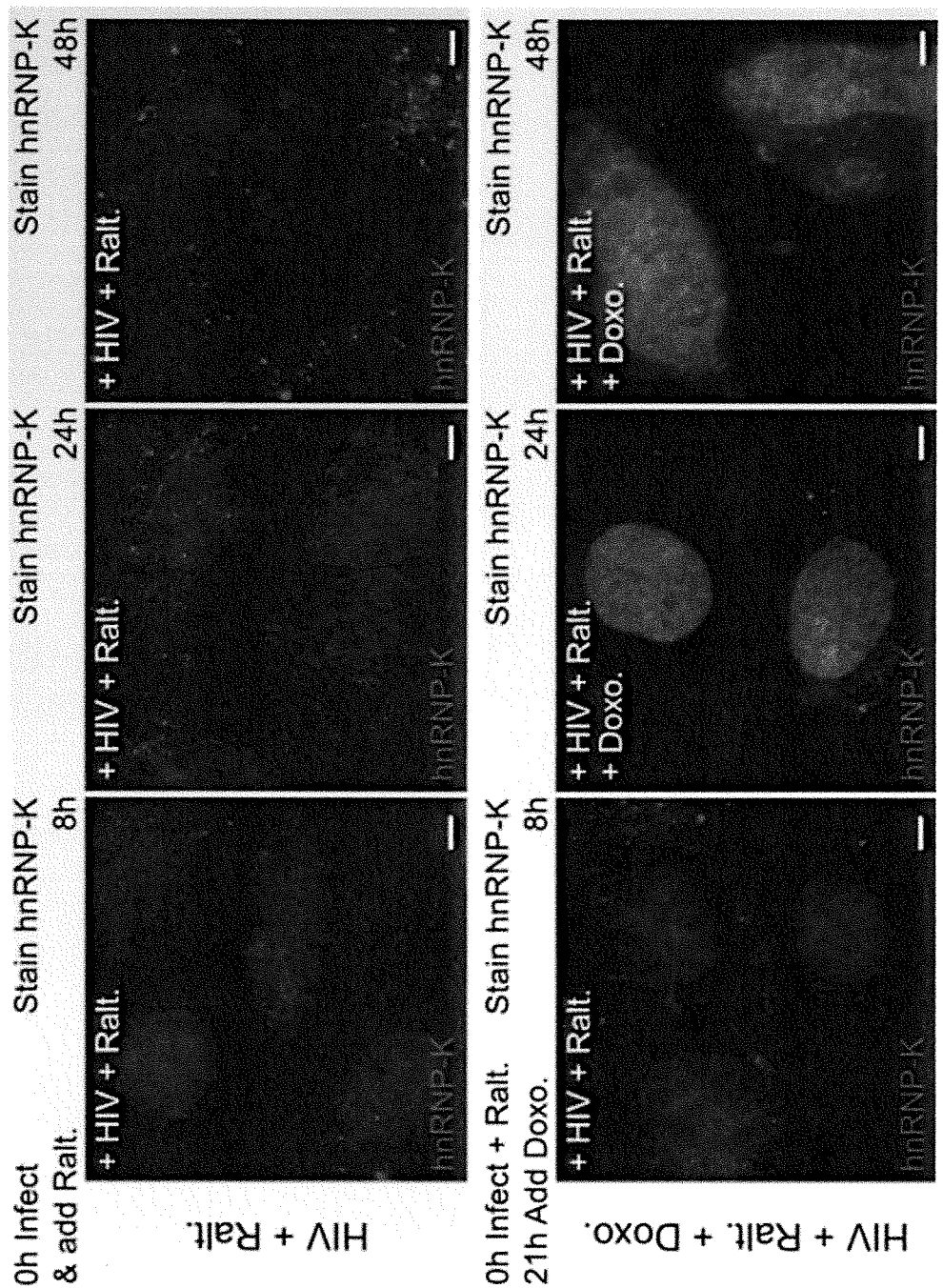

FIG. 20: HIV1 prevents nuclear localisation of lincRNAp21 protein binding partner hnRNPK Viral control of cytoplasmic hnRNPK requires integration. Ghost(3) cells concurrently infected and exposed to Raltegravir (Ralt.) show no GFP expression and cytoplasmic hnRNPK as expected in the absence of DNA damage. Similarly treated cells exposed to Doxorubicin at 21 hours show nuclear hnRNPK within 3 hours of chemical-induced DNA damage.

Figure 21:
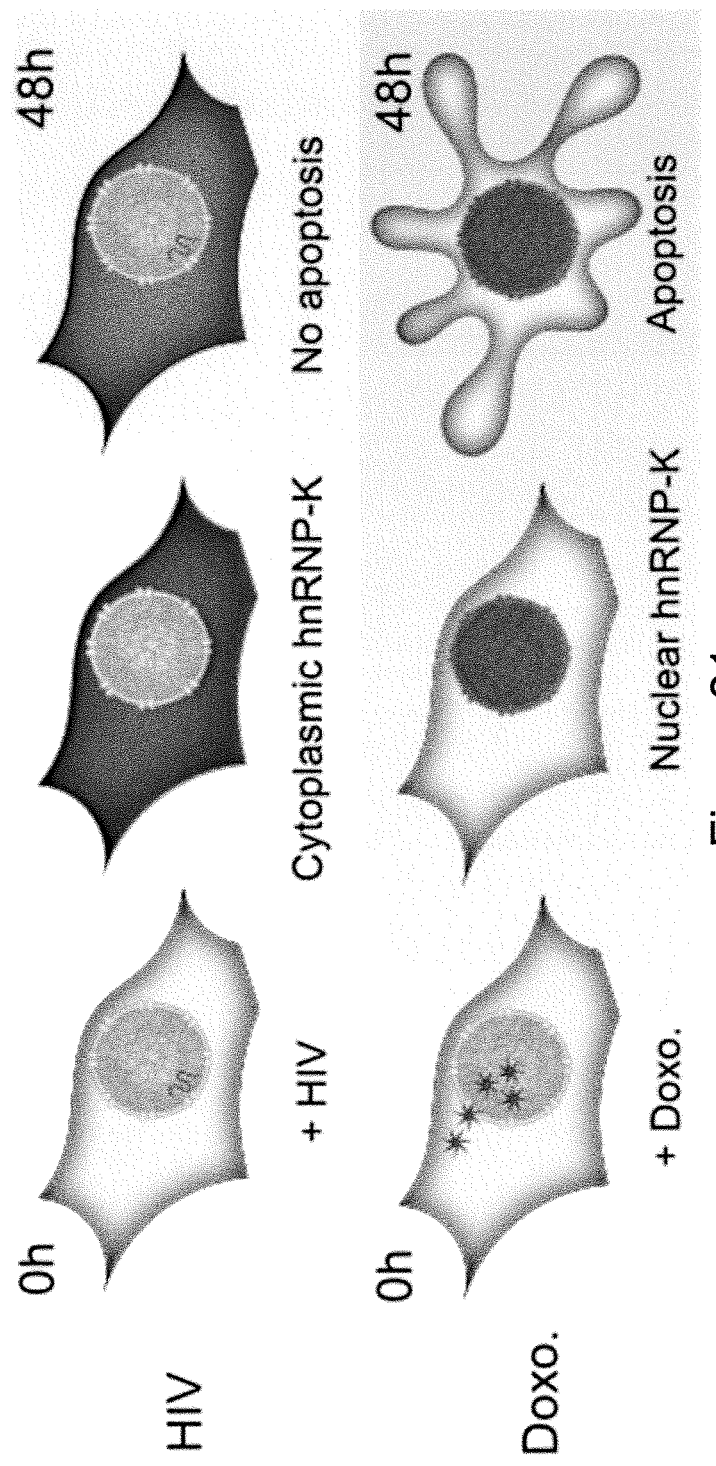

FIG. 21: HIV1 prevents nuclear localisation of lincRNAp21 protein binding partner hnRNPK HIV1 integration excludes hnRNPK from the nucleus thereby negating the proper localisation required to mediate apoptosis as seen in Doxorubicin-treated cells. Cells were counterstained with DAPI; Scale bars=10 μM FIG. 22: Exogenous full-length lincRNAp21 together with Nutlin3a treatment induces nuclear hnRNPK and apoptosis in HIV-infected cells hnRNPK is negatively regulated by HDM2 and can be activated by Nutlin3a. Both p53 and hnRNPK are activated in response to DNA damage (i) and both are negatively regulated by HDM2 (ii). Nutlin3a (Nut.3) binds HDM2 and releases its negative regulation of p53 and hnRNPK (iii).

Figure 23:
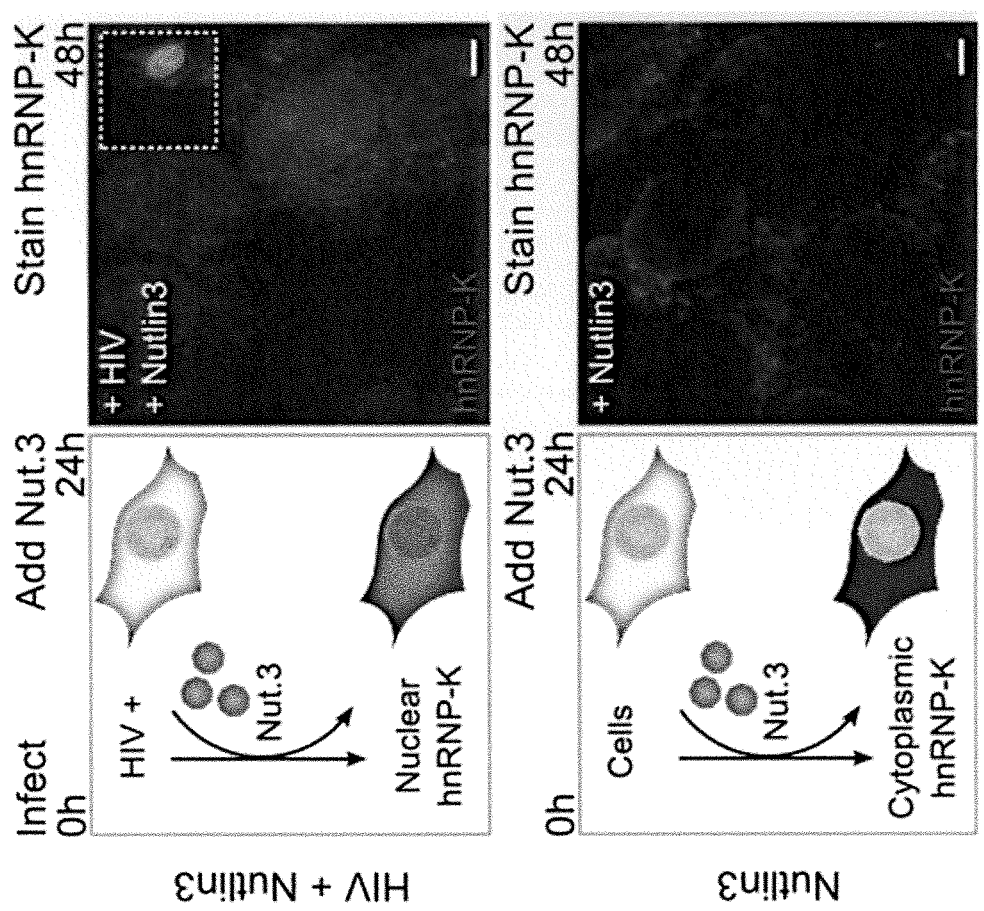

FIG. 23: Exogenous full-length lincRNAp21 together with Nutlin3a treatment induces nuclear hnRNPK and apoptosis in HIV-infected cells Nutlin3a treatment leads to nuclear hnRNPK of HIV-infected cells only. Exposure of Ghost(3) cells to Nutlin3a (Nut.3) 24 hours post-infection leads to nuclear localisation of hnRNPK at 48 hours in GFP-positive cells only. Nutlin3aexposed cells show cytoplasmic hnRNPK as expected in the absence of DNA damage.

Figure 24:
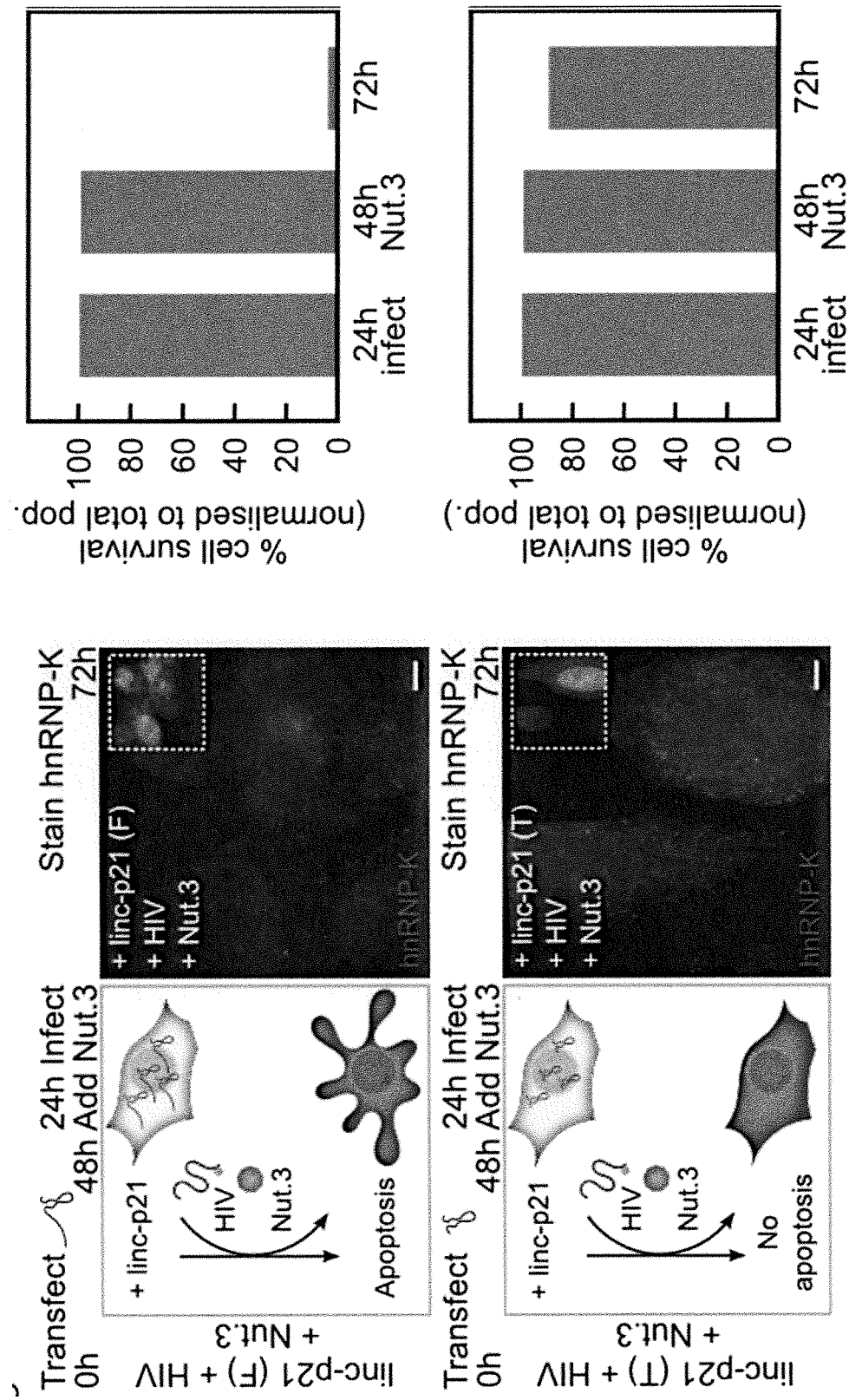

FIG. 24: Exogenous full-length lincRNAp21 together with Nutlin3a treatment induces nuclear hnRNPK and apoptosis in HIV-infected cells Exogenous full-length lincRNAp21 expression and Nutlin3a treatment lead to nuclear hnRNPK and apoptosis in HIV-infected cells. Ghost(3) cells transfected for 24 hours with full-length (F) exogenous lincRNAp21 prior to HIV1 infection for 24 hours followed by Nutlin3a (Nut.3) treatment show nuclear hnRNPK and undergo apoptosis within 24 hours of Nutlin3a addition. Similarly treated cells transfected with truncated (T) exogenous lincRNAp21 show nuclear hnRNPK but do not undergo apoptosis.

Figure 25:
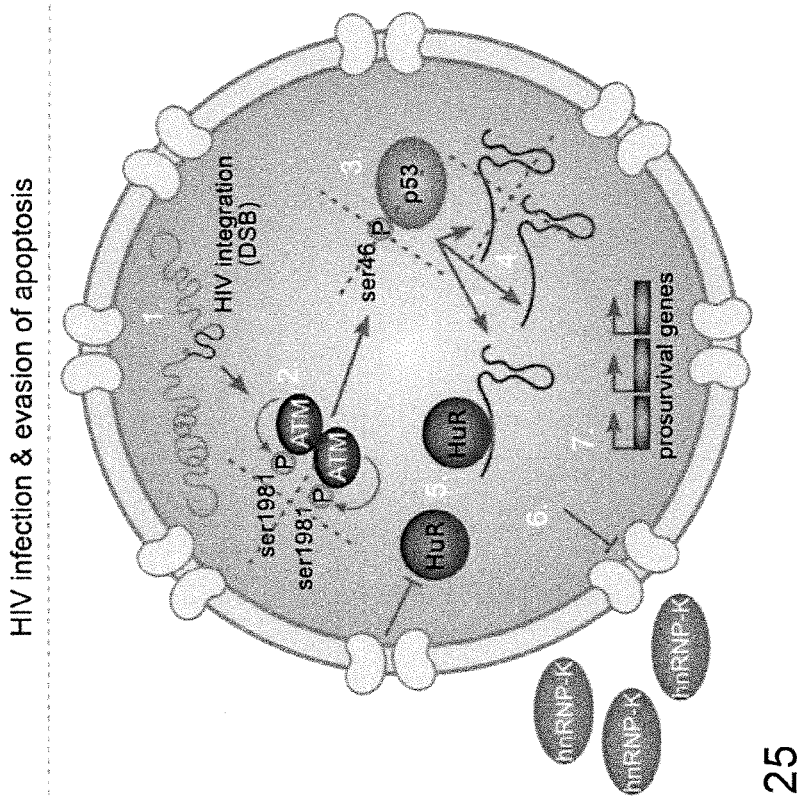
Figure 25:
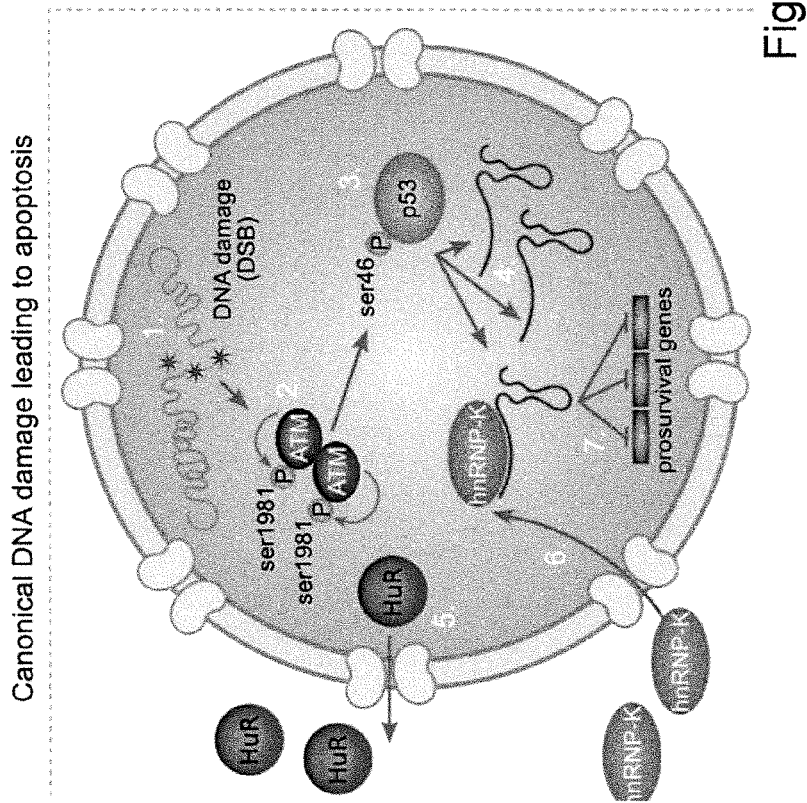

FIG. 25: Exogenous full-length lincRNAp21 together with Nutlin3a treatment induces nuclear hnRNPK and apoptosis in HIV-infected cells Hypothetical model of HIV-mediated manipulation of lincRNAp21, HuR and hnRNPK to evade cellular apoptosis. When compared to canonical DNA damage, both HIV1 integration and Doxorubicin induce DSBs (1). However, in HIV1 infected cells this does not lead to autophosphorylation and activation of ATM at serine $_{1981}$ (2) or subsequent phosphorylation of p53 at serine 46 (3). The p53pSer46 apoptosis mark leads to increased lincRNAp21 transcription (4) and translocation of HuR to the cytoplasm (5) of canonically DNA damaged cells only. In addition, lincRNAp21 associates with hnRNPK in the nucleus (6) of canonically DNA damaged cells only leading to suppression of prosurvival genes (7). As HIV1 is able to alter the location of HuR (5) and hnRNPK (6), lincRNAp21 expression is low and prosurvival genes are not repressed (7) in infected cells thus the virus is able to evade apoptosis.

Figure 26:
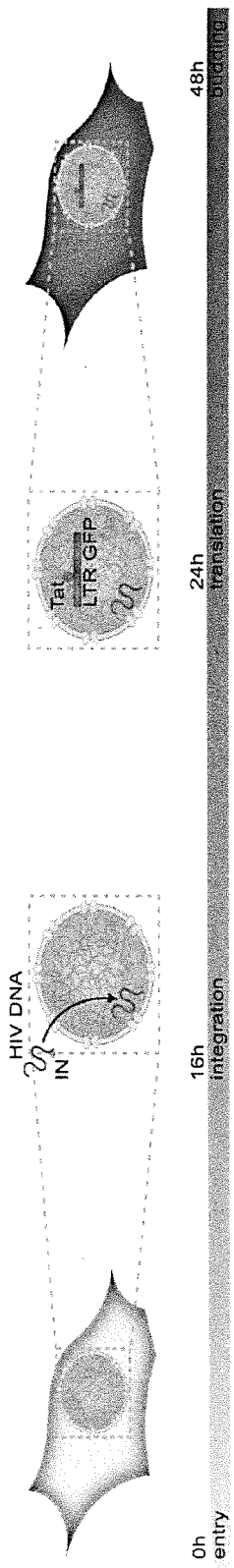

FIG. 26: HIV-1 masks IN-induced DSBs and prevents lincRNA-p21 up-regulation

HIV-1 integration occurs approximately 16 hours post-infection of Ghost(3) reporter cells and Tat-mediated activation of an integrated LTR-driven GFP reporter can be detected approximately 48 hours post-infection.

Figure 27:
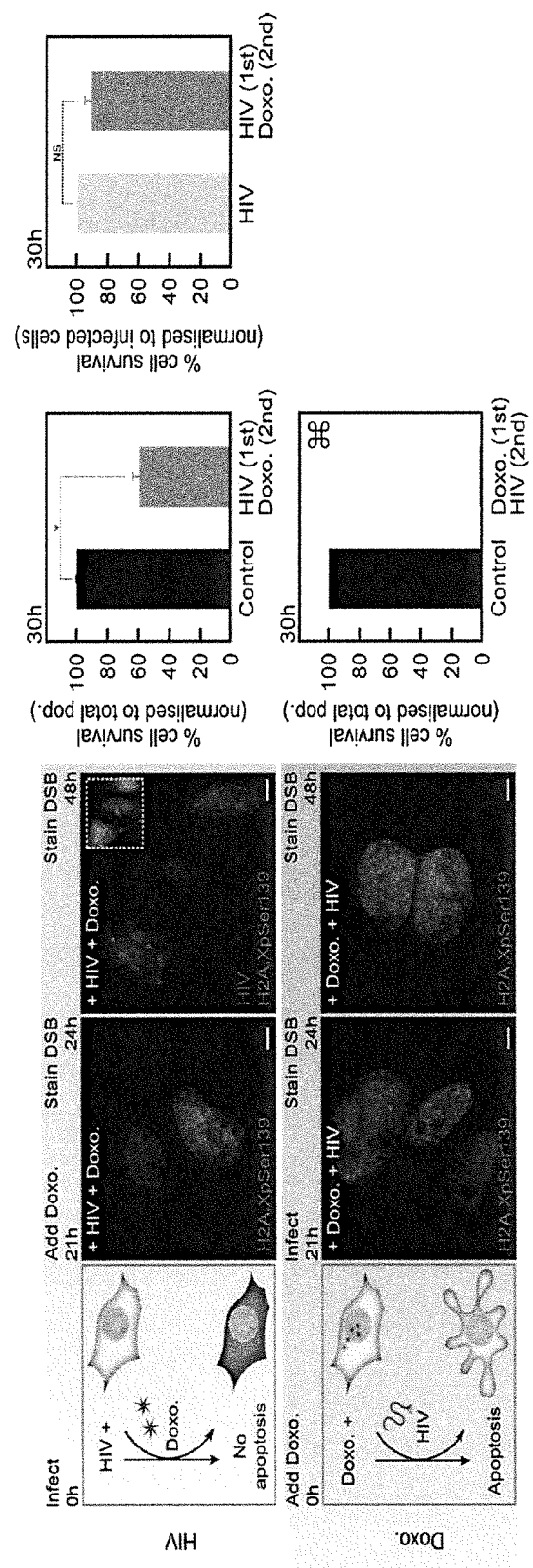

FIG. 27: HIV-1 masks IN-induced DSBs and prevents lincRNA-p21 up-regulation

HIV-1 infection protects against additional lethal DNA damage. Ghost(3) cells infected 24 hours prior to Doxorubicin treatment (+HIV+Doxo.) have numerous DSBs as detected by H2A.XpSer139 immunofluorescence staining but do not undergo apoptosis when normalised to infected cells (HIV (1st) Doxo. (2nd)). Cells infected after exposure to Doxorubicin (+Doxo.+HIV) have extensive H2A.XpSer139 staining and do undergo apoptosis. ⌘ Too few attached cells (<20) were present for statistical analysis. Cells were counterstained with DAPI; Scale bars=10 μM; Two-tailed paired Student T-test, *p<0.001, p<0.01, *p<0.05, NS (not significant)

Figure 28:
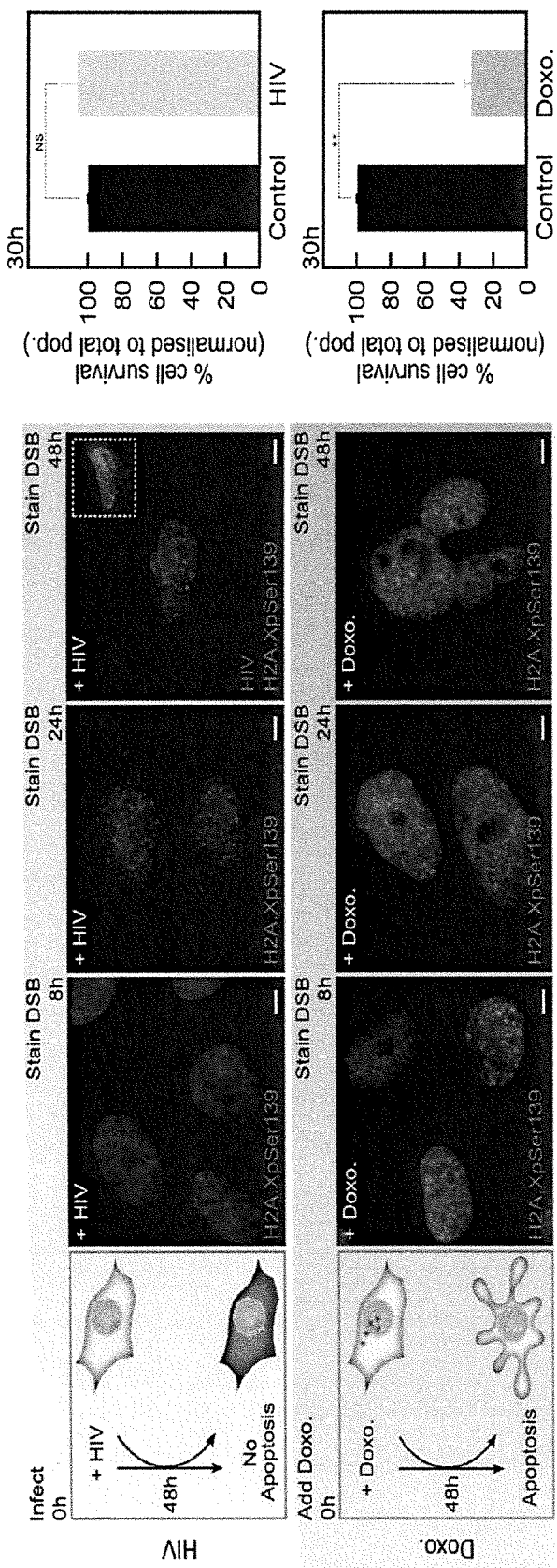

FIG. 28: HIV-1 masks IN-induced DSBs and prevents lincRNA-p21 up-regulation

ATM is not activated in response to HIV-1 infection. Inactive ATM dimers do not undergo autophosphorylation of serine residue 1981 in response to HIV-induced DSBs as measured by immunofluorescence staining (ATMpSer1981) in Ghost(3) cells. Phosphorylated ATM is detected in Doxorubicin-treated cells. Cells were counterstained with DAPI; Scale bars=10 μM; Two-tailed paired Student T-test, *p<0.001, p<0.01, *p<0.05, NS (not significant)

Figure 29:
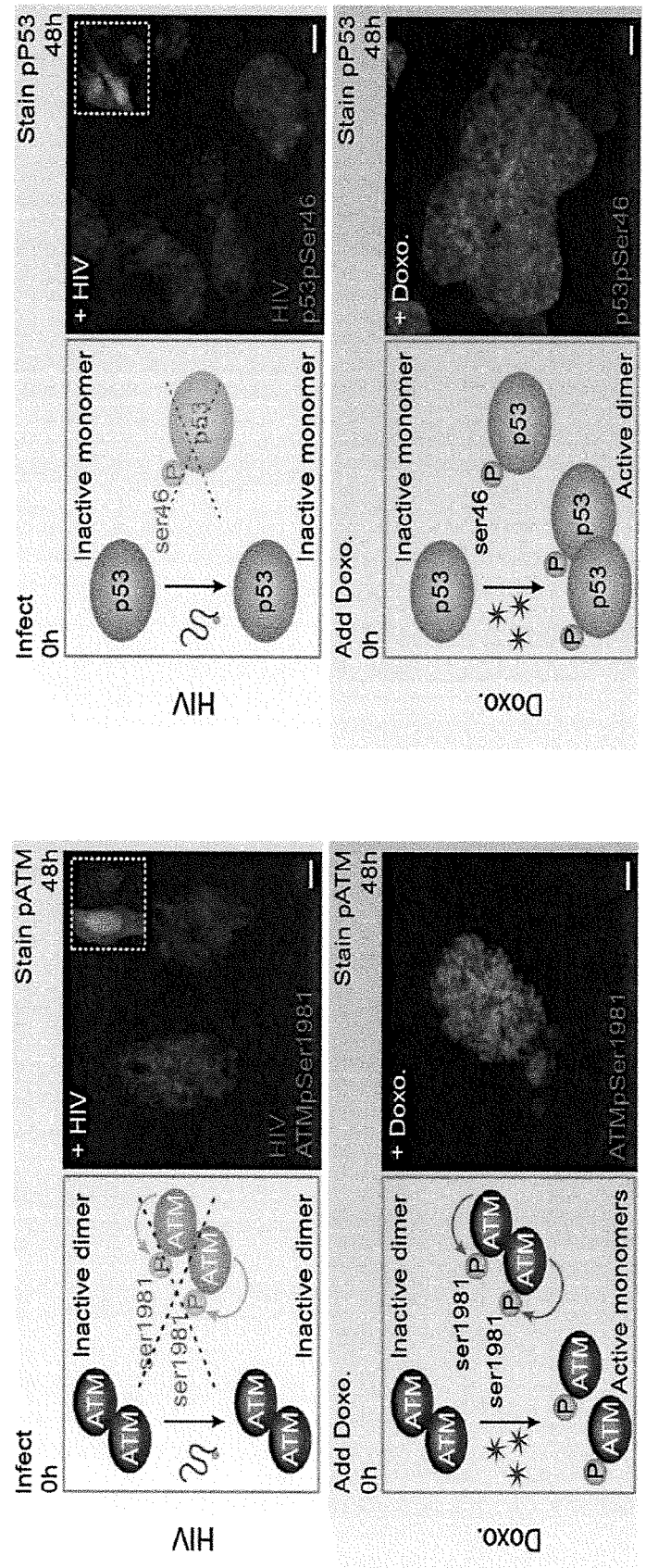

FIG. 29: HIV-1 masks IN-induced DSBs and prevents lincRNA-p21 up-regulation

The apoptotic mark on p53 is not activated in HIV-infected cells. Inactive p53 monomers are not phosphorylated at serine residue 46 in response to HIV-1 infection of Ghost(3) cells as measured by immunofluorescence staining (p53pSer46). Activated p53 dimers are detected in Doxorubicin-treated cells. Cells were counterstained with DAPI; Scale bars=10 μM; Two-tailed paired Student T-test, *p<0.001, p<0.01, *p<0.05, NS (not significant)

Figure 30:
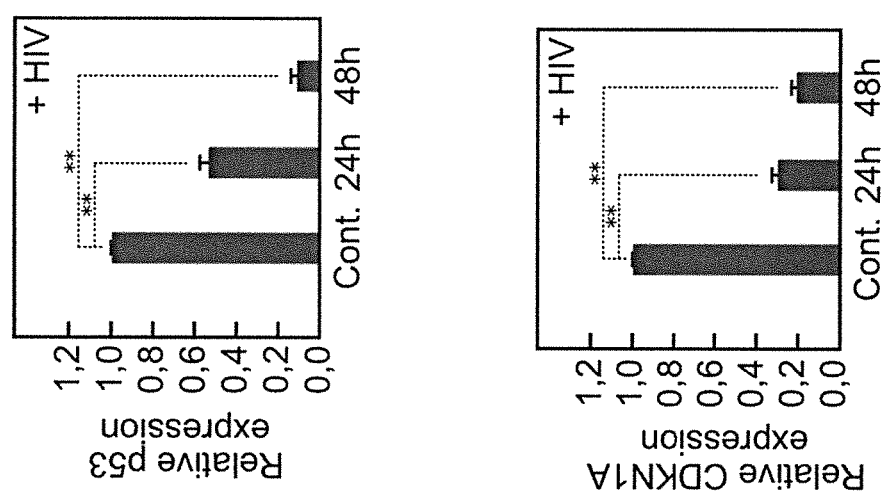

FIG. 30: HIV-1 masks IN-induced DSBs and prevents lincRNA-p21 up-regulation

HIV-1 infection significantly decreases p53 (upper panel) and CDKN1A/p21 (lower panel) expression over time relative to HPRT housekeeping gene. Quantitative real-time RT-PCR analysis of HIV-infected Ghost(3) cells normalised to uninfected cells (mean±SD of 3 biological replicates).

Figure 31:
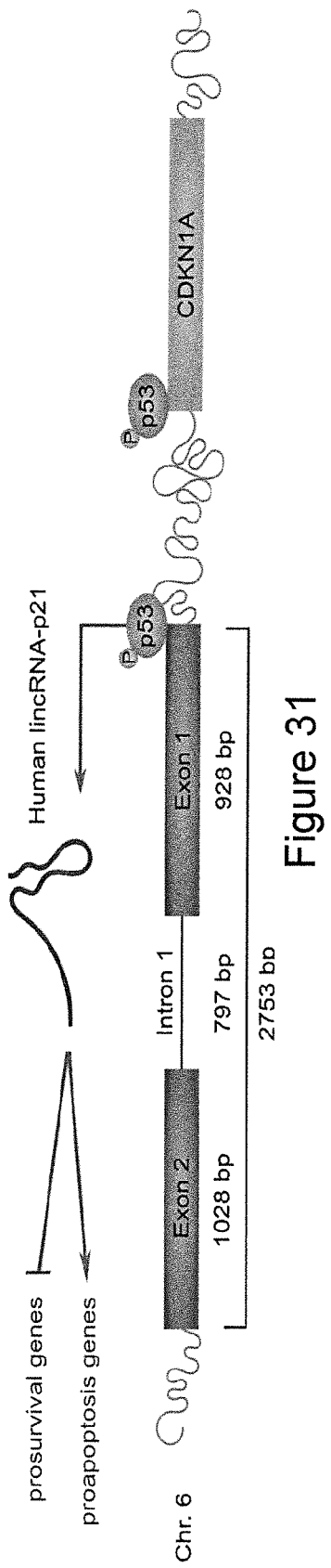

FIG. 31: HIV-1 masks IN-induced DSBs and prevents lincRNA-p21 up-regulation

Human lincRNA-p21, which is located upstream of CDKN1A/p21 on chromosome 6 and comprised of 2 exons and a single intron, is transcribed by p53 in response to DNA damage. LincRNA-p21 mediates cellular apoptosis by down-regulating prosurvival genes and up-regulating proapoptosis genes.

Figure 32:
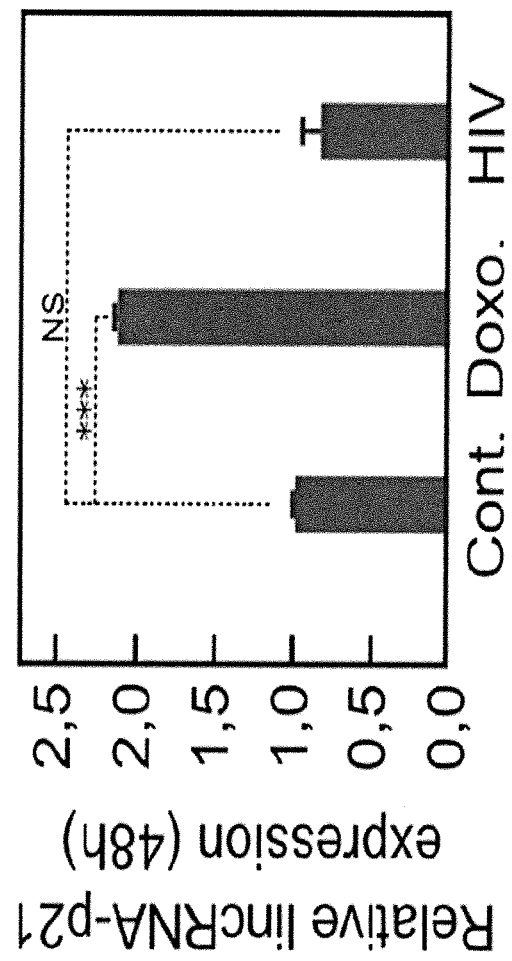

FIG. 32: HIV-1 masks IN-induced DSBs and prevents lincRNA-p21 up-regulation

HIV-induced DNA damage does not lead to enhanced lincRNA-p21 expression. Quantitative real-time RT-PCR analysis of lincRNA-p21 expression at 48 hours relative to HPRT housekeeping gene in Doxorubicin-treated (Doxo.) and infected Ghost(3) cells normalised to untreated cells (mean±SD of 3 biological replicates).

Figure 33:
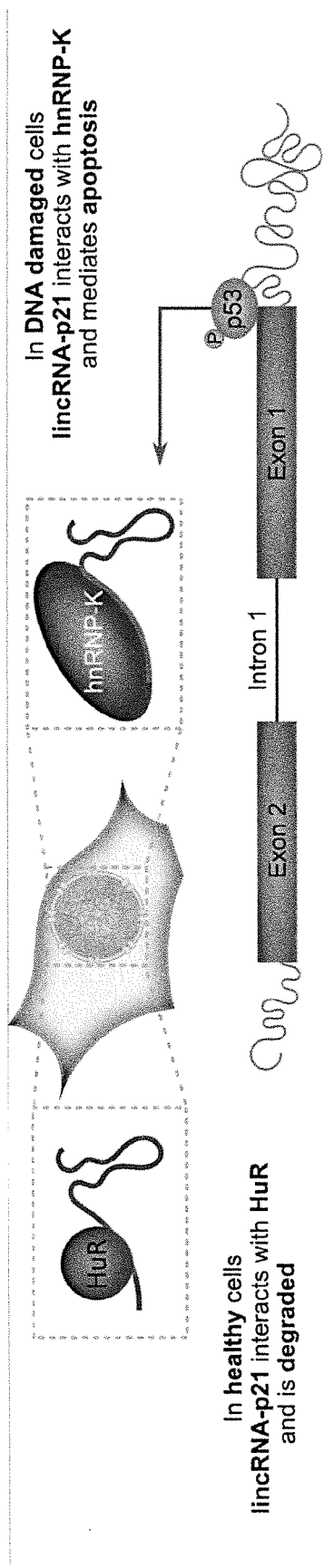

FIG. 33: HIV-1 alters cellular location of lincRNA-p21's protein partners

LincRNA-p21 has two cellular protein binding partners. In healthy cells, lincRNA-p21 associates with HuR in the nucleus and is degraded. In response to p53-mediated transcription, lincRNA-p21 associates with hnRNP-K in the nucleus of DNA-damaged cells and regulates apoptosis by localising hnRNP-K to the promoters of p53-repressed genes.

Figure 34:
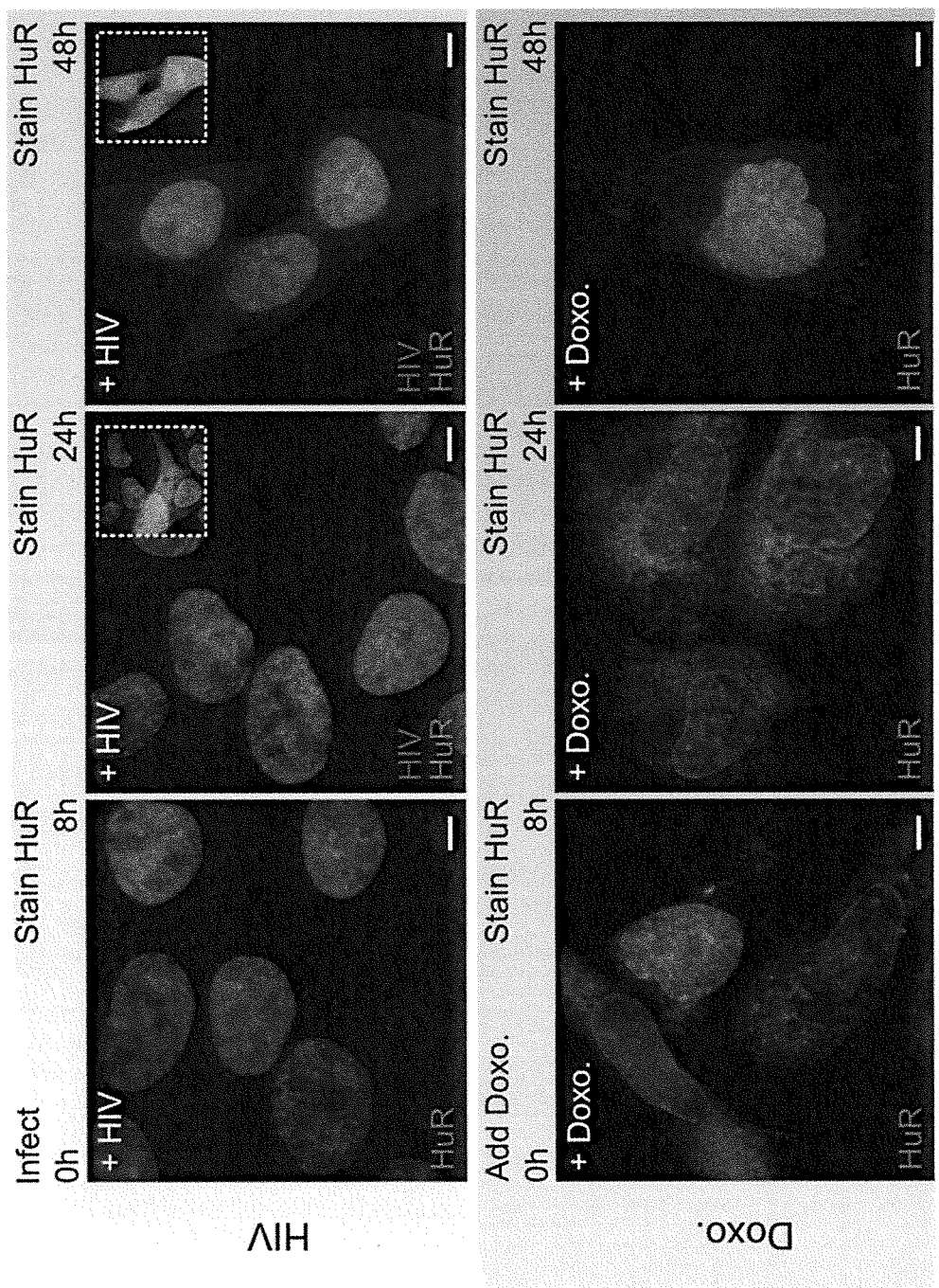

FIG. 34: HIV-1 alters cellular location of lincRNA-p21's protein partners

HIV-1 prevents cytoplasmic location of HuR. Immunofluorescence staining reveals cytoplasmic HuR within 8 hours of Doxorubicin-treated (Doxo.) Ghost(3) cells while HIV-infected cells show nuclear HuR up until 48 hours. Cells were counterstained with DAPI; Scale bars=10 μM; Two-tailed paired Student T-test, *p<0.001, p<0.01, *p<0.05, NS (not significant).

Figure 35:
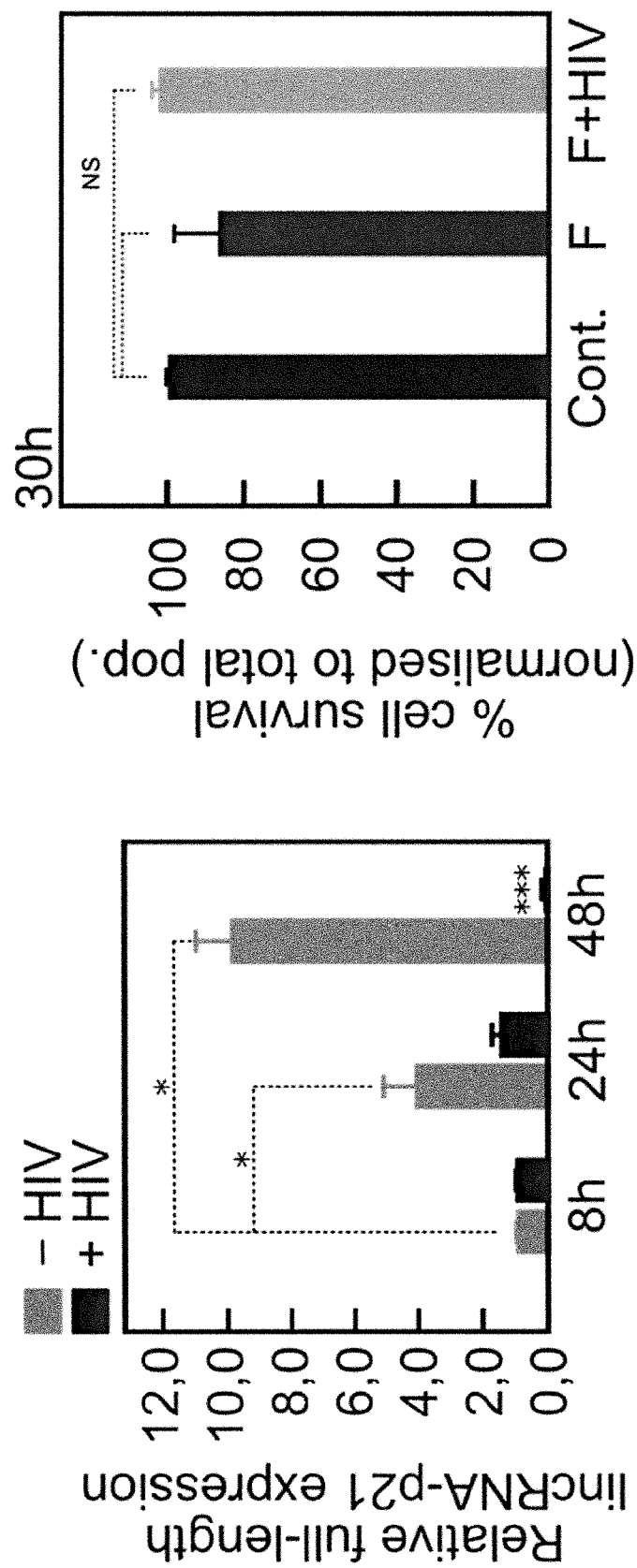

FIG. 35: HIV-1 alters cellular location of lincRNA-p21's protein partners

LincRNA-p21 expression increases in the absence of HuR but does not affect HIV replication. Quantitative real-time RT-PCR analysis (left panel) of lincRNA-p21 expression over time relative to HPRT housekeeping gene in HIV-infected (dark grey) and uninfected (light grey) Ghost(3) cells treated for 48 hours prior to infection with an siRNA targeted to HuR (mean±SD of 3 biological replicates). siHuR-treated cells support HIV-1 replication to the same extent as untreated cells, as indicated by GFP expression (right panel). Scale bar=5 μM.

Figure 36:
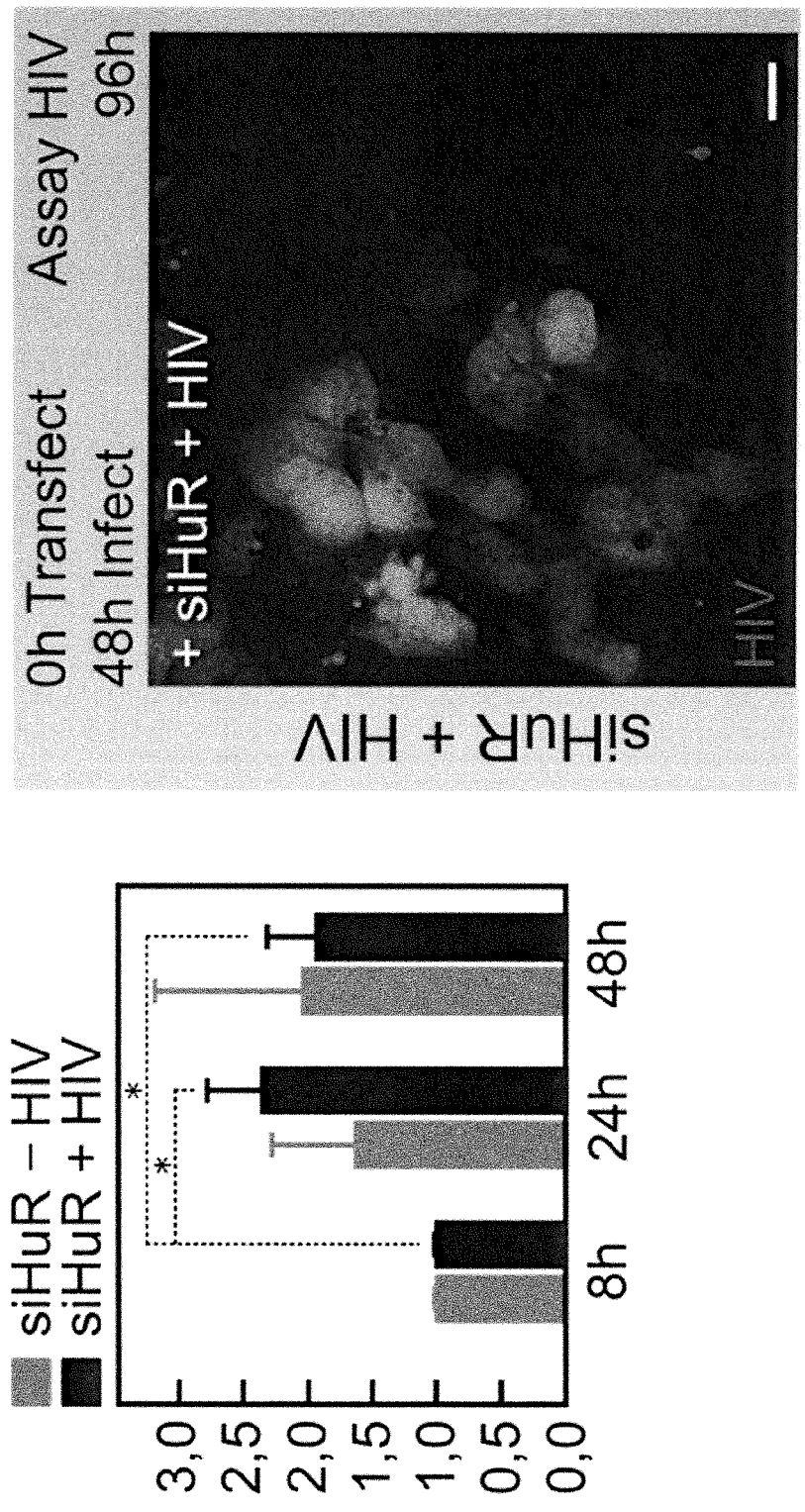

FIG. 36: HIV-1 alters cellular location of lincRNA-p21's protein partners

Exogenous full-length lincRNA-p21 expression is reduced and viability is maintained in HIV-infected cells. Quantitative real-time RT-PCR analysis (left panel) of lincRNA-p21 expression over time relative to HPRT housekeeping gene in HIV-infected (dark grey) and uninfected (light grey) Ghost(3) cells (mean±SD of 3 biological replicates). Cell viability (right panel) does not change in the presence of exogenous lincRNA-p21 (blue) relative to uninfected cells (black) unless Doxorubicin (Doxo.) is present (orange). Cells were counterstained with DAPI; Scale bars=10 µM; Two-tailed paired Student T-test, *p<0.001, p<0.01, *p<0.05, NS (not significant).

Figure 37:
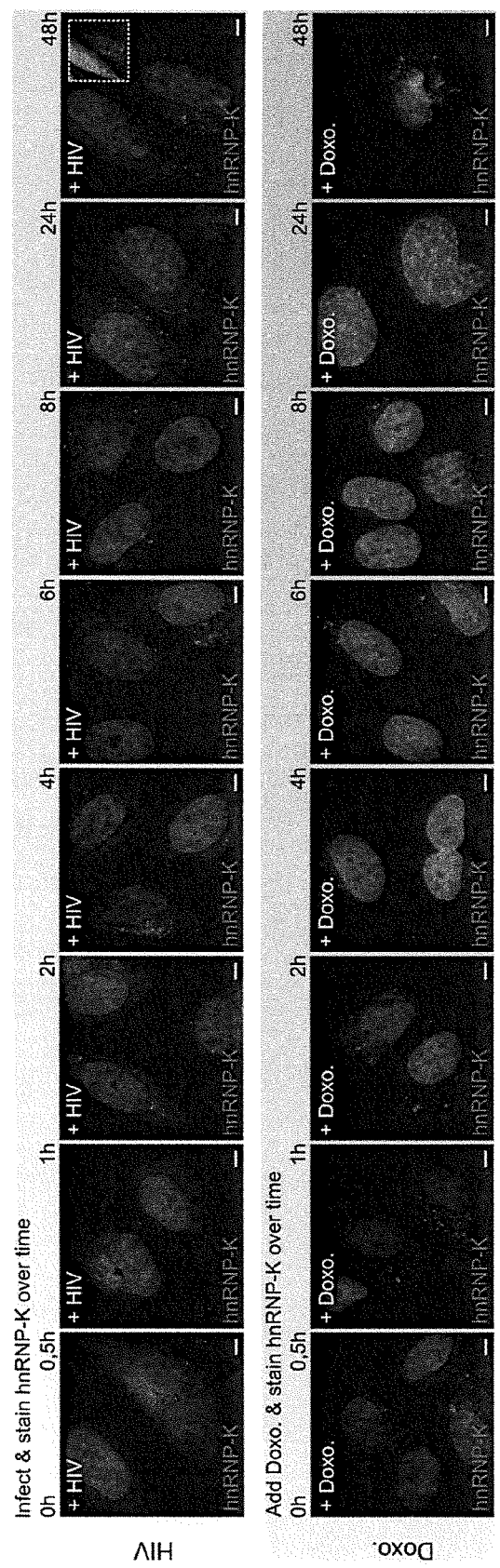

FIG. 37: HIV-1 alters cellular location of lincRNA-p21's protein partners

HIV-1 prevents nuclear localisation of hnRNP-K in Ghost (3) cells. Immunofluorescence staining reveals nuclear hnRNP-K within 2 hours of Doxorubicin-treated (Doxo.) cells while HIV-infected cells show cytoplasmic hnRNP-K throughout all 8 time points spanning the same 48 hour time course. Cells were counterstained with DAPI; Scale bars=10 µM; Two-tailed paired Student T-test, *p<0.001, p<0.01, *p<0.05, NS (not significant).

Figure 38:
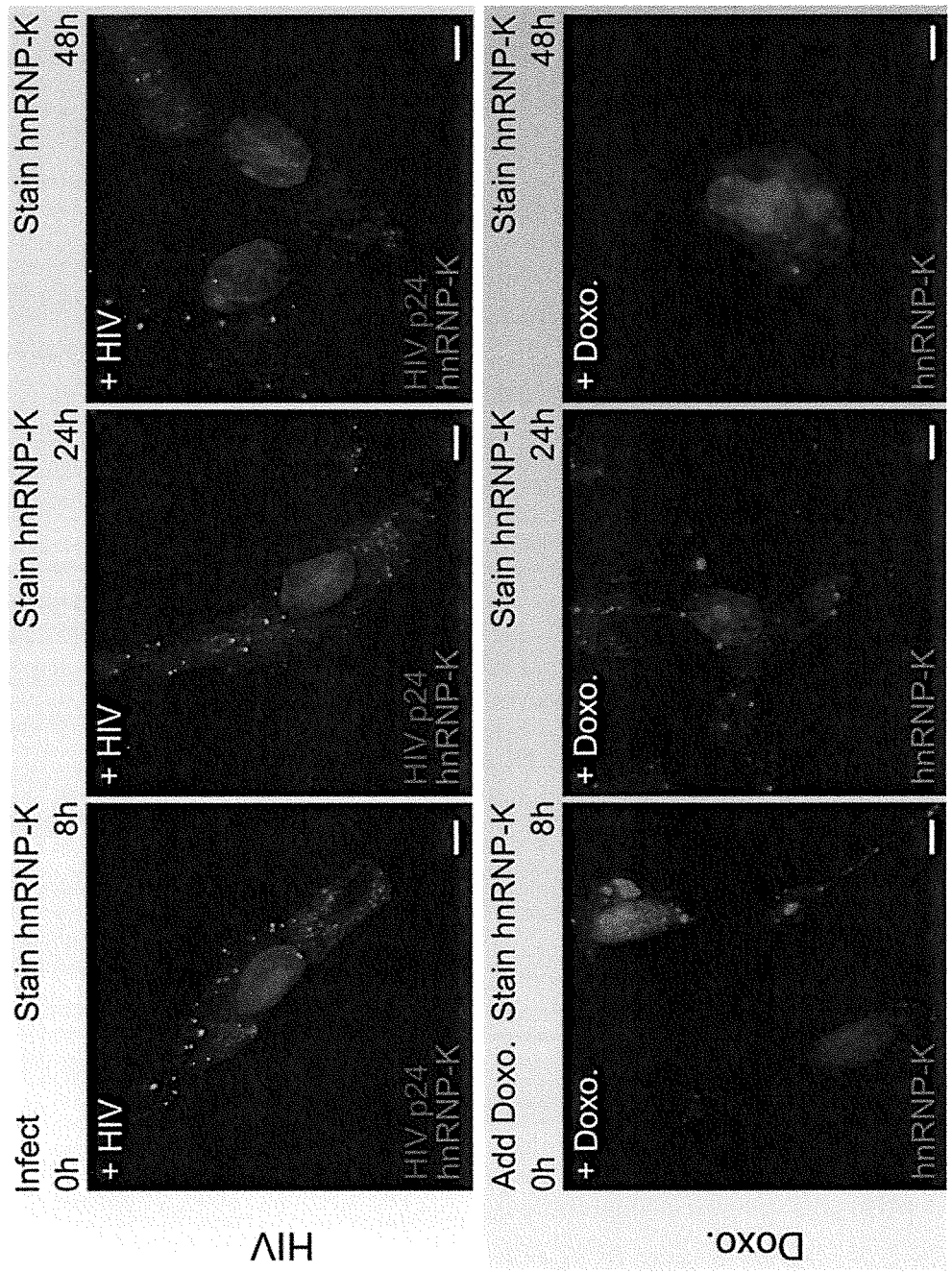

FIG. 38: HIV-1 alters cellular location of lincRNA-p21's protein partners

HIV-1 prevents nuclear localisation of hnRNP-K in iPSC-derived macrophages. Immunofluorescence staining reveals nuclear hnRNP-K within 8 hours of Doxorubicin-treated (Doxo.) macrophages while HIV-infected cells (green p24 staining) show cytoplasmic hnRNP-K throughout the same 48 hour time course. Cells were counterstained with DAPI; Scale bars=10 µM; Two-tailed paired Student T-test, *p<0.001, p<0.01, *p<0.05, NS (not significant).

Figure 39:
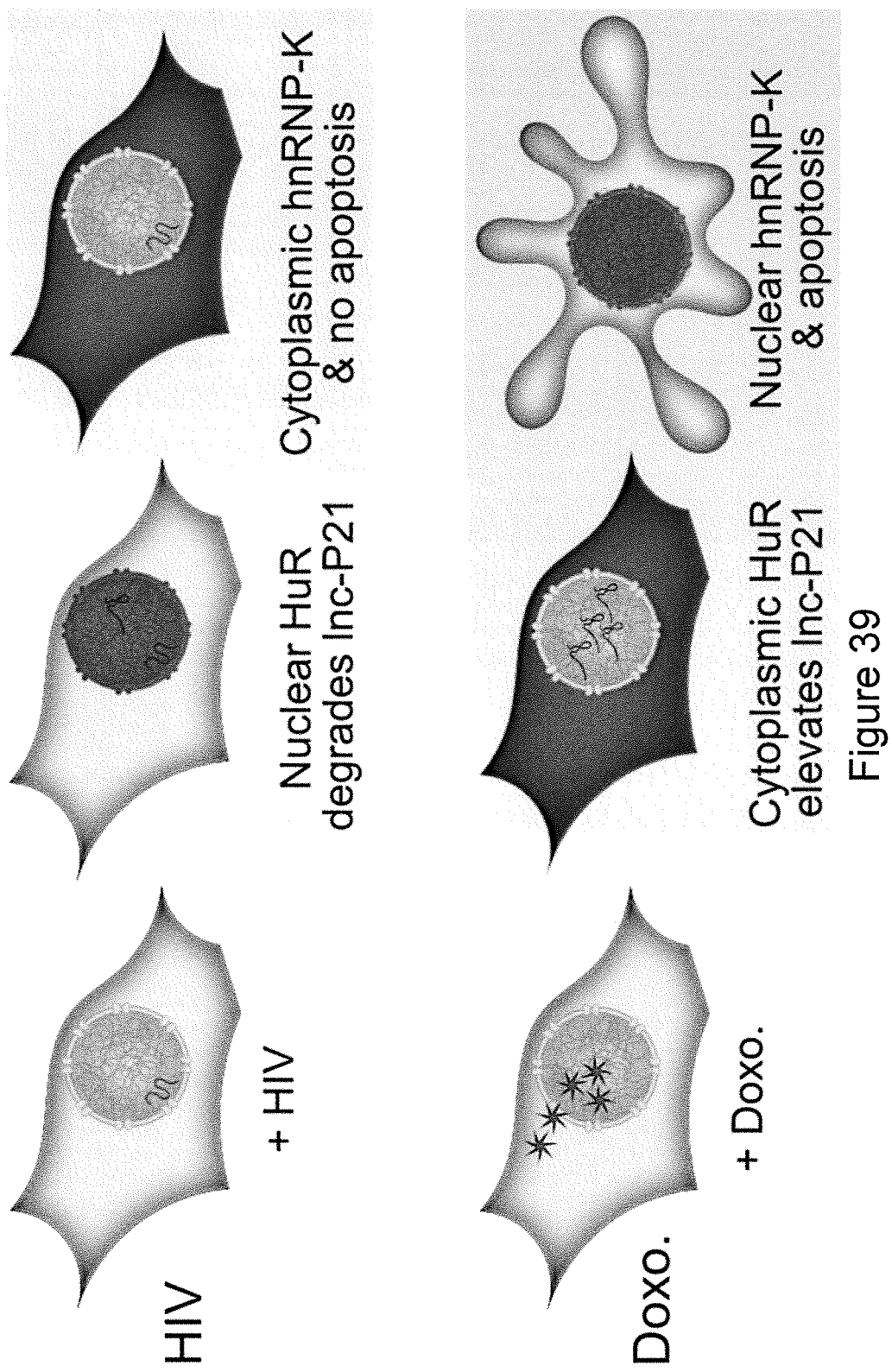

FIG. 39: HIV-1 alters cellular location of lincRNA-p21's protein partners

HIV-1 integration sequesters HuR in the nucleus of cells leading to degradation of lincRNA-p21. The virus also excludes hnRNP-K from the nucleus thereby negating the proper localisation required to mediate apoptosis as seen in Doxorubicin-treated cells.

Figure 40:
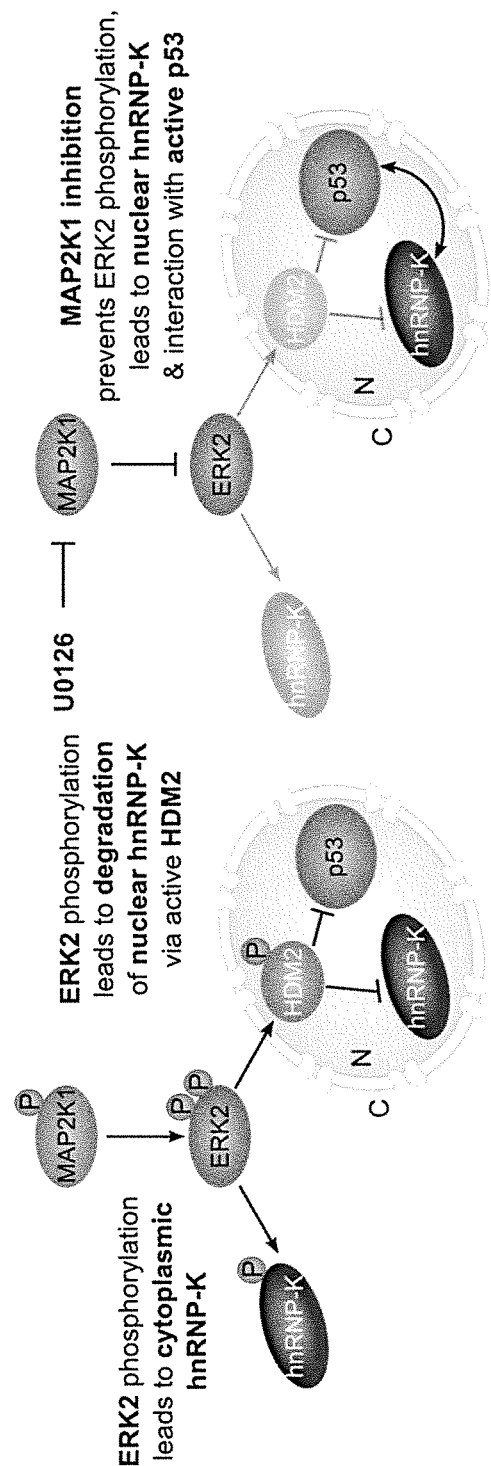

FIG. 40: HIV-1 requires MAP2K1/ERK2 to control cytoplasmic hnRNP-K

Activated MAP2K1 specifically phosphorylates ERK2 leading to cytoplasmic accumulation of phosphorylated hnRNP-K. Simultaneously, ERK2 activation of HDM2 ensures ubiquitin-mediated degradation of nuclear hnRNP-K and p53 (i). Inhibition of MAP2K1 prevents ERK2-mediated accumulation of hnRNP-K, and releases the negative regulation of HDM2 on nuclear hnRNP-K and p53.

Figure 41:
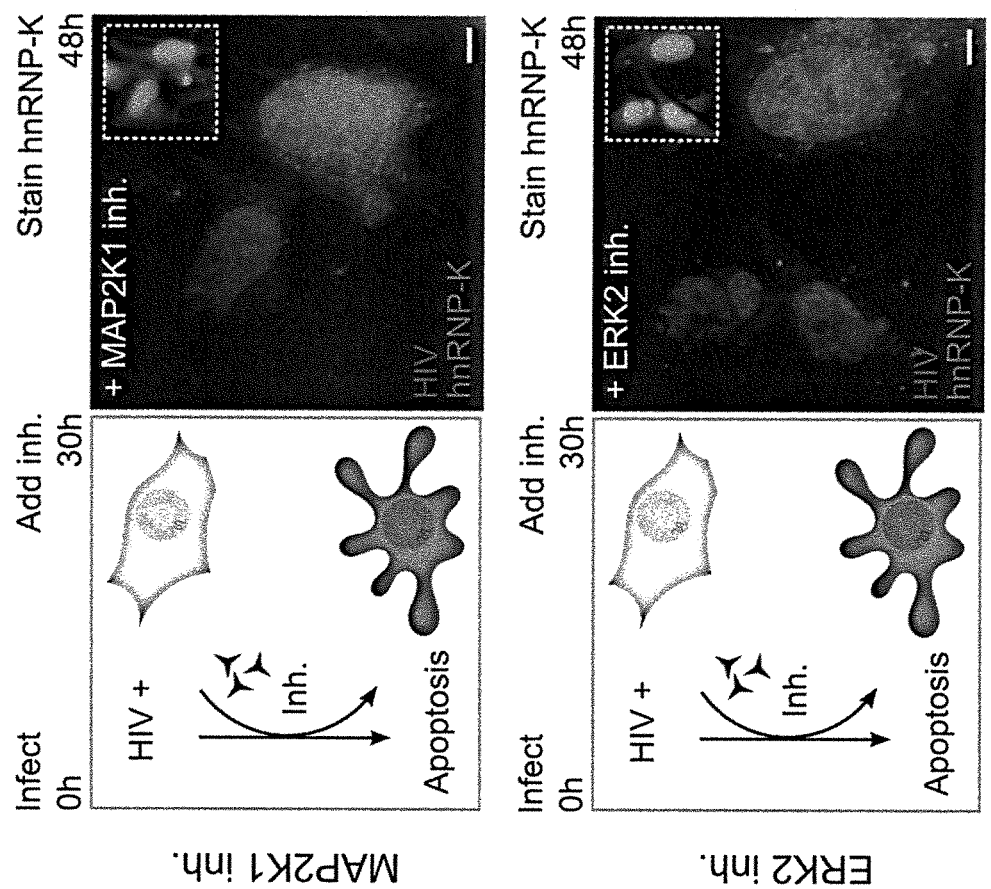

FIG. 41: HIV-1 requires MAP2K1/ERK2 to control cytoplasmic hnRNP-K

Inhibition of MAP2K1 or ERK2 allows for nuclear localisation of hnRNP-K and apoptosis in HIV-infected cells. Immunofluorescence staining reveals nuclear hnRNP-K following the addition of either a MAP2K1 (upper panel) or ERK2 (lower panel) inhibitor in HIV-infected Ghost(3) cells. Cells were counterstained with DAPI; Scale bars=10 µM; Two-tailed paired Student T-test, *p<0.001, p<0.01, *p<0.05, NS (not significant).

Figure 42:
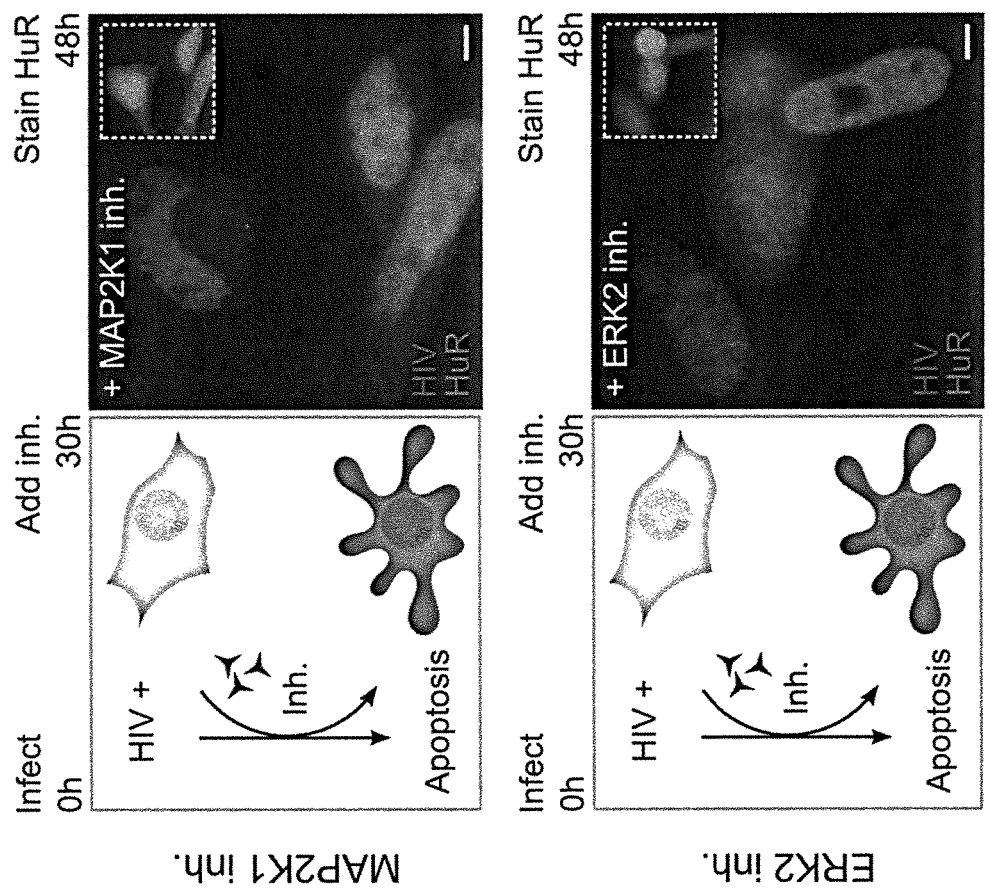

FIG. 42: HIV-1 requires MAP2K1/ERK2 to control cytoplasmic hnRNP-K

HIV-1 requires MAP2K1 to control HuR localisation. Immunofluorescence staining reveals cytoplasmic (and nuclear) HuR following the addition of a MAP2K1 inhibitor (upper panel) in HIV-infected cells only. Cytoplasmic HuR is not observed in HIV-infected cells treated with an ERK2 inhibitor (lower panel). Cells were counterstained with DAPI; Scale bars=10 µM; Two-tailed paired Student T-test, *p<0.001, p<0.01, *p<0.05, NS (not significant).

Figure 43:
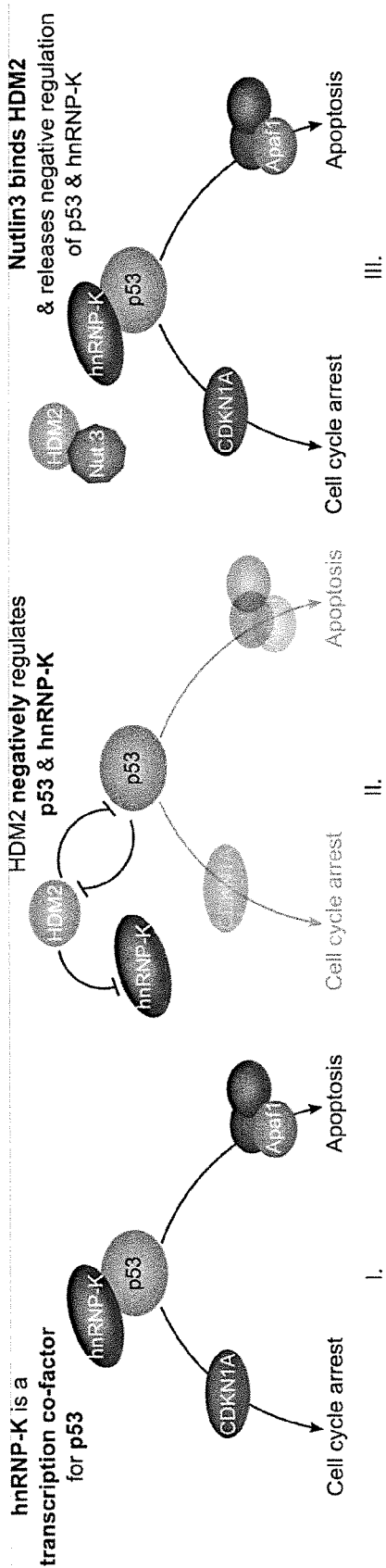

FIG. 43: Nutlin3a confirms HIV-mediated evasion of apoptosis centres on nuclear hnRNP-K hnRNP-K is negatively regulated by HDM2 and can be activated by Nutlin3a. Both p53 and hnRNP-K are activated in response to DNA damage (i) and both are negatively regulated by HDM2 (ii). Nutlin3a (Nut.3) binds HDM2 and releases its negative regulation of p53 and hnRNP-K (iii).

Figure 44:
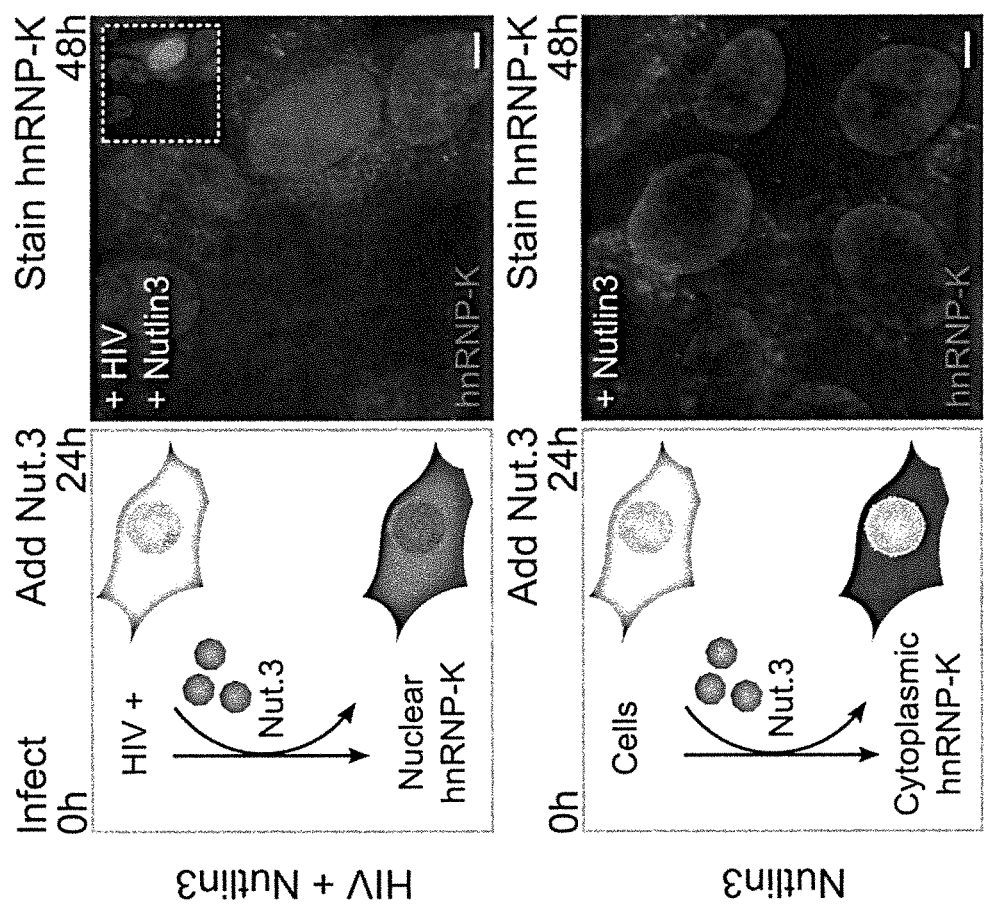

FIG. 44: Nutlin3a confirms HIV-mediated evasion of apoptosis centres on nuclear hnRNP-K Nutlin3a treatment leads to nuclear hnRNP-K of HIV-infected cells only. Exposure of Ghost(3) cells to Nutlin3a (Nut.3) 24 hours post-infection leads to nuclear localisation of hnRNP-K at 48 hours in GFP-positive cells only. Nutlin3a-exposed cells show cytoplasmic hnRNP-K as expected in the absence of DNA damage. Cells were counterstained with DAPI; Scale bars=10 µM.

Figure 45:
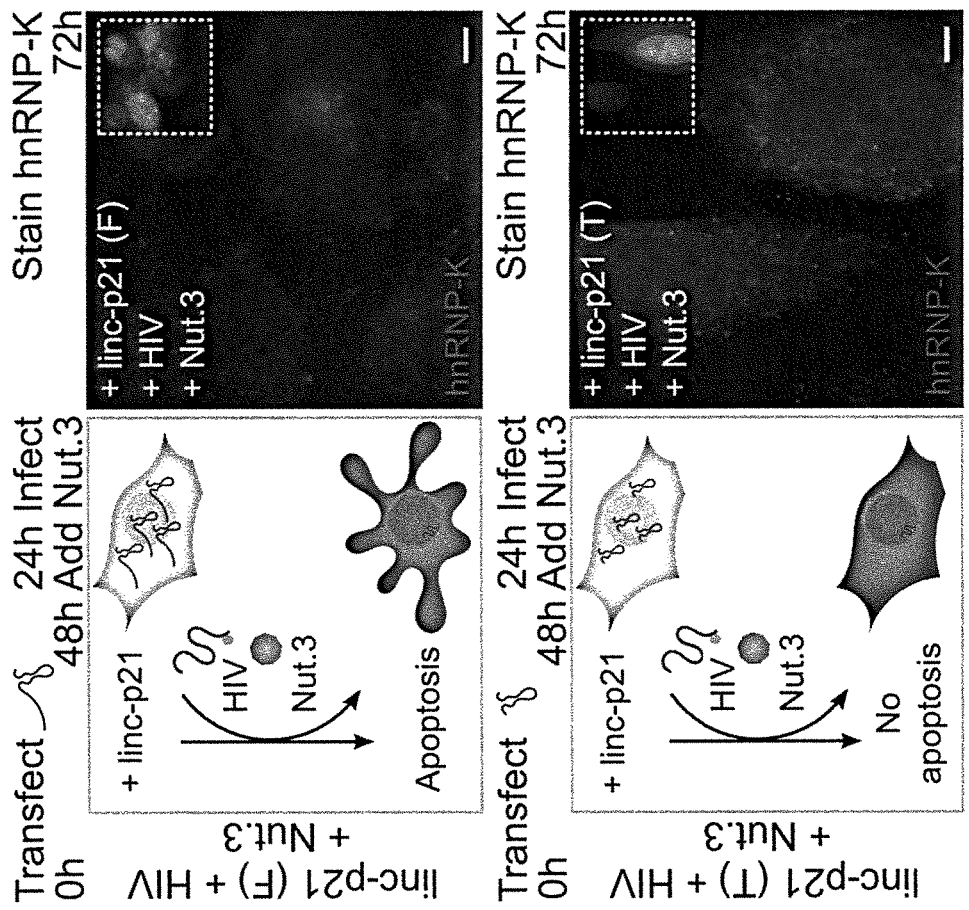

FIG. 45: Nutlin3a confirms HIV-mediated evasion of apoptosis centres on nuclear hnRNP-K Exogenous full-length lincRNA-p21 expression and Nutlin3a treatment lead to nuclear hnRNP-K and apoptosis in HIV-infected cells. Ghost(3) cells transfected for 24 hours with full-length (F) exogenous lincRNA-p21 prior to HIV-1 infection for 24 hours followed by Nutlin3a (Nut.3) treatment show nuclear hnRNP-K and undergo apoptosis within 24 hours of Nutlin3a addition. Similarly treated cells transfected with truncated (T) exogenous lincRNA-p21 show nuclear hnRNP-K but do not undergo apoptosis. Cells were counterstained with DAPI; Scale bars=10 µM.

Figure 46:
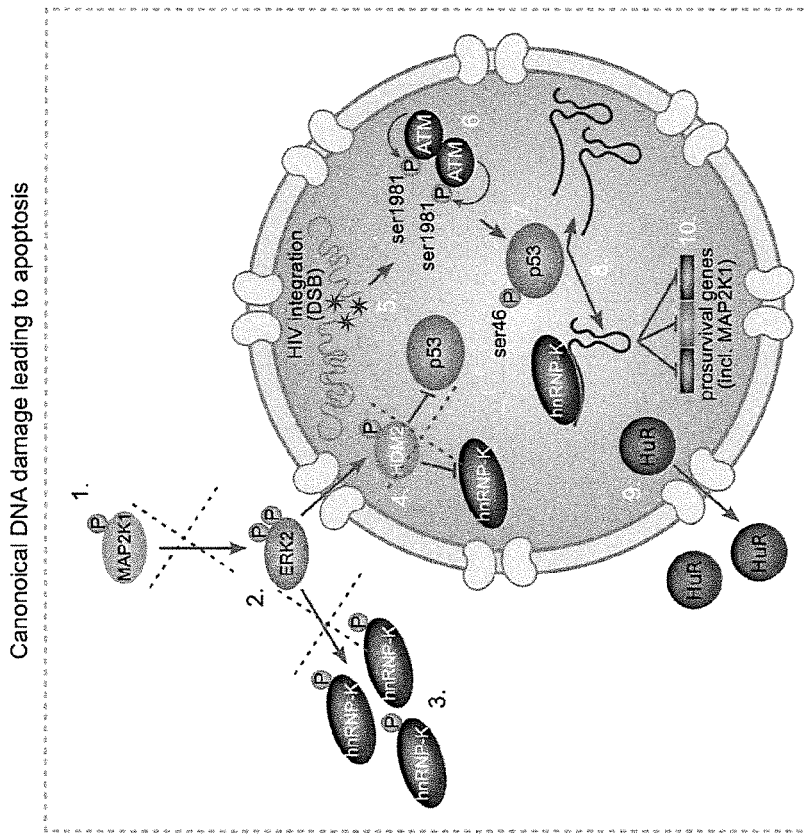
Figure 46:
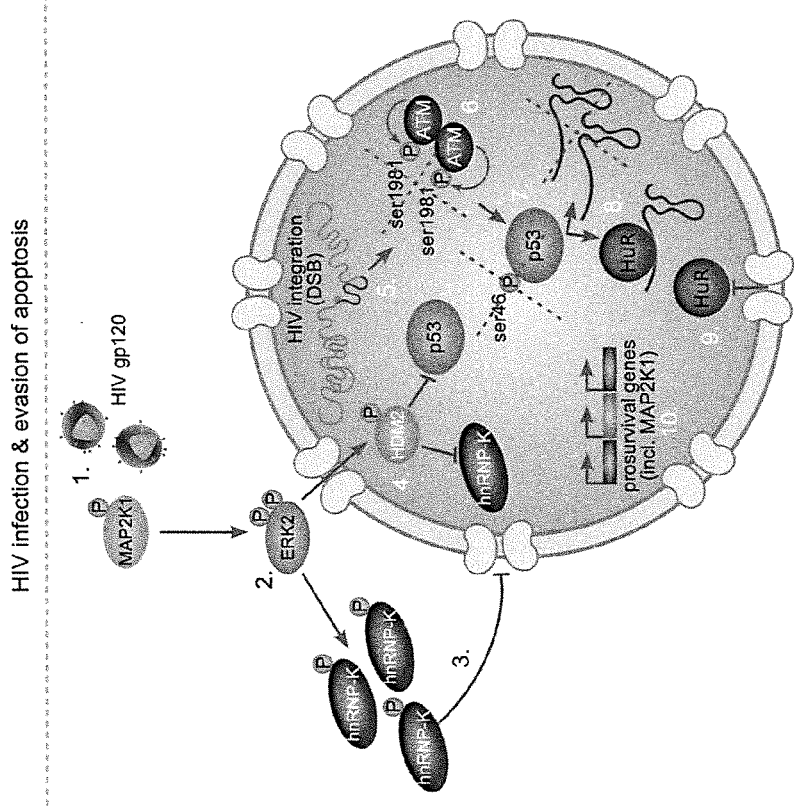

FIG. 46: Hypothetical model of HIV-mediated manipulation of lincRNA-p21, HuR and hnRNP-K to evade cellular apoptosis

DETAILED DESCRIPTION OF A PREFERRED EMBODIMENT

During canonical DNA damage, the MAP2K1/ERK2 pathway is inactivated. However, during infection, HIV-1 ensures activated MAP2K1 (1) continues to phosphorylate ERK2 (2) thereby leading to cytoplasmic accumulation of hnRNP-K (3) as well as phosphorylation of HDM2 (4). The latter action of ERK2 ensures ubiquitin-mediated degradation of nuclear hnRNP-K as well as p53. When compared to canonical DNA damage, both HIV-1 integration and Doxorubicin induce DSBs (5). However, in HIV-1-infected cells this does not lead to autophosphorylation and activation of ATM at serine 1981 (6) or subsequent phosphorylation of p53 at serine 46 (7). The p53pSer46 apoptosis mark leads to increased lincRNA-p21 transcription and association with hnRNP-K (8), as well as translocation of HuR to the cytoplasm (9) of canonically DNA damaged cells only. Nuclear lincRNA-p21/hnRNP-K complexes lead to suppression of prosurvival genes in canonically DNA damaged cells only (10). As HIV-1 is able to alter the location of hnRNP-K (3) and HuR (9), lincRNA-p21 expression is low and prosurvival genes, including MAP2K1, are not repressed in infected cells (10) thus the virus is able to evade apoptosis.

DETAILED DESCRIPTION OF THE INVENTION

The present invention will now be described more fully hereinafter with reference to the accompanying drawings, in which some, but not all embodiments of the invention are shown.

The invention as described should not be limited to the specific embodiments disclosed and modifications and other embodiments are intended to be included within the scope of the invention. Although specific terms are employed herein, they are used in a generic and descriptive sense only and not for purposes of limitation.

As used throughout this specification and in the claims which follow, the singular forms "a", "an" and "the" include the plural form, unless the context clearly indicates otherwise.

The terminology and phraseology used herein is for the purpose of description and should not be regarded as limiting. The use of the terms "comprising", "containing", "having" and "including" and variations thereof used herein, are meant to encompass the items listed thereafter and equivalents thereof as well as additional items.

The term "apoptosis" refers to the highly regulated and controlled process of programmed cell death that may occur in multicellular organisms as result of intracellular apoptotic signalling in response to a stress.

The term "cancer" refers to human cancers and carcinomas, sarcomas, adenocarcinomas, lymphomas, leukemias, etc., including but not limited to solid tumors and lymphoid cancers, kidney, breast, lung, kidney, bladder, colon, ovarian, prostate, pancreas, stomach, brain, head and neck, skin, uterine, testicular, esophagus, and liver cancer, lymphoma, including non-Hodgkin's and Hodgkin's lymphoma, leukemia, and multiple myeloma.

The terms "overexpress," "overexpression" or "overexpressed" interchangeably refer to a gene that is transcribed or translated at a detectably greater level, in comparison to a normal cell. Overexpression therefore refers to both overexpression of protein and/or RNA (due to increased transcription, post transcriptional processing, translation, post translational processing, altered stability, and/or altered protein degradation), as well as local overexpression due to altered protein traffic patterns (increased nuclear localization), and augmented functional activity, e.g., as in an increased enzyme hydrolysis of substrate.

The term "inhibitor" refers to an agent that, by way of non-limiting example, inhibits expression of a polypeptide or polynucleotide of the invention or bind to, partially or totally block stimulation or enzymatic activity, decrease, prevent or delay activation, inactivate, desensitize, or down regulate the activity of a polypeptide or polynucleotide of the invention, e.g., antagonists.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI website: ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

The term "up-regulation" refers to the process by which a cell increases the quantity of a cellular component, such as RNA or protein, in response to an external variable or stimulus.

The following examples are provided by way of illustration and not by way of limitation.

EXAMPLE 1

Cell Culture

Ghost(3) cells (AIDS Research and Reference Reagent Program, Division of AIDS, NIAID, NIH) were cultured in DMEM (Invitrogen) supplemented with 10% heat-inactivated fetal bovine serum (FBS; Biochrom), 0.2 mM GlutaMAX™ (Life Tech), 500 µg/mL G418 (Sigma), 100 µg/mL Hygromycin (Sigma) and 1 µg/mL Puromycin (Sigma). Mouse NIH3T3 cells (AIDS Research and Reference Reagent Program, Division of AIDS, NIAID, NIH) were cultured in DMEMF12 (Invitrogen) supplemented with 10% heat-inactivated FBS and 0.2 mM GlutaMAX™ (Life Tech). HEK293T and TZMBI cells (AIDS Research and Reference Reagent Program, Division of AIDS, NIAID, NIH) were cultured in DMEM (Invitrogen) supplemented with 10% heat-inactivated FBS. Macrophages were derived from induced pluripotent stem cells (28), characterised (29) and cultured in XVivo15 media (Lonza) supplemented with 1× Glutamax (Invitrogen), 50 µM β-mercaptoethanol (Sigma), 25 ng/mL IL3 (Invitrogen) and 100 ng/mL MCSF (Peprotech).

Viral Plasmids, Virus Stocks, Infections and Drugs

Viral stocks were generated by co-transfecting HEK293T cells with HIV1 clones BaL.01 and pSG3Δenv (AIDS Research and Reference Reagent Program, Division of AIDS, NIAID, NIH) using Fugene6 (Roche). Supernatants were collected 48 hours post-transfection, supplemented with FBS to a final concentration of 20% and stored in aliquots at 80° C. Viral stocks were titred using TZMBI cells and used to infect Ghost(3) cells using an MOI=1.0, or IPSO-derived macrophages using an MOI=0.5. Where indicated, Ghost(3) cells were treated with 10 µM of either Raltegravir, Maraviroc, Tenofovir (AIDS Research and Reference Reagent Program, Division of AIDS, NIAID, NIH) or Nutlin3a (Sigma) for up to 48 hours.

Cloning and Transfections

Ghost(3) cells were transfected for 48 hours prior to infection with 25 nM (final concentration) of ONTARGETplus human HuR/ELAV1 siRNA SMARTpool (5' GAC AAA AUC UUA CAG GUU U 3' (SEQ ID NO:1), 5' GAC AUG UUC UCU CGG UUU G 3' (SEQ ID NO:2), 5' ACA AAU AAC UCG CUC AUG C 3' (SEQ ID NO:3), 5' GCU CAG AGG UGA UCA AAG A 3' (SEQ ID NO:4); ThermoScientific) using RNAiMax (Invitrogen). Mouse fulllength lincRNAp21 (3073 bp) (GenBank Accession Number: HM210889) and truncated lincRNAp21 (1889 bp) sequences were synthesised (GeneArt, Life Technologies) and subcloned via 5' SacI and 3' EcoRI into pCiNeo (Promega). Ghost(3) cells were transfected for 21 hours prior to infection with either construct using Lipofectamine2000 (Invitrogen).

RNA FISH Probes

RNA FISH on Ghost(3) cells was performed according to Raj, 2008 and on primary macrophages according to Schaffer, 2013. For both methods 48 20mer probes (Biosearch) targeted to human lincRNAp21 were synthesised baring a 30-amino-modifier C6dT. The amino group was subsequently conjugated to the following NHSester dyes: ATTO565, ATTO647N (ATTOTEC) or Alexa Fluor 647 (Invitrogen). Briefly, oligonucleotide probes were ethanol precipitated and resuspended in 0.1 M sodium tetraborate (Sigma). Approximately 0.3 mg of the NHSester dye (ATTOTEC) was dissolved in dimethyl sulphoxide (Sigma). The dye solution was added to the probe solution and incubated overnight in the dark at 37° C. Following the conjugation reaction, the probes were ethanol precipitated overnight, and resuspended in 0.1 M triethyl ammonium (Sigma). Conjugated probes were separated and purified to enrich for dyeconjugated probes by reverse phase HPLC on a C18 column.

RNA Fish

For each experiment, Ghost(3) cells were infected or treated with 500 nM Doxorubicin (Sigma) on coverslips, fixed for 10 mins in fresh 4% paraformaldehyde at room temperature, then washed 3 times in PBS and permeabilised overnight in 70% ethanol at 4° C. Coverslips were washed once in PBS and hybridised overnight in a humidified chamber at 37° C. in 50 µL of hybridisation buffer (10% dextran sulfate, 1 mg/ml E. coli tRNA, 2 mM vanadyl ribonucleoside complex, 0.02% RNase-free BSA, 10% formamide) together with 50 ng of dye-conjugated single molecule RNA FISH probes. Coverslips were washed 3 times (30 mins each on an orbital shaker) in wash buffer (10% formamide, 2×SCC). Cells were incubated in equilibration buffer (0.4% glucose, 2×SCC) for 5 mins and counter stained with 1 mg/ml DAPI (4',6-diamidino-2-phenylindole; Life Technologies). Coverslips were mounted in glox buffer (3.7 mg/ml glucose oxidase, 1 U catalase) and imaged. Primary macrophages were similarly treated with the following exceptions: cells were fixed in ice-cold methanol for 10 mins at 20° C.; coverslips were hybridised for 5 mins at 37° C. in 50 µL of hybridisation buffer together with 1 µg of dyeconjugated single molecule RNA FISH probes.

Immunofluorescence

For each experiment, Ghost(3) cells or IPSC-derived primary macrophages were infected or treated with 500 nM Doxorubicin on coverslips, fixed for 10 mins in fresh 4% paraformaldehyde at room temperature, then washed 3 times in PBS and permeabilised for 10 mins in ice-cold methanol at 20° C. Coverslips were washed once in PBS and incubated in blocking buffer (5% goat serum, 0.3% TritonX100 in PBS) for 60 mins at room temperature. Cells were incubated in primary antibody solution (1% BSA, 0.3% Triton X100 in PBS) overnight at 4° C. Double strand breaks were detected using rabbit polyclonal anti-phosphohistone H2A.X Ser139 (Cell Signaling). Activated ATM was detected using rabbit monoclonal anti-phosphoATM Ser1981 (Cell Signaling). The ability of p53 to regulate apoptosis was detected using rabbit polyclonal antiphosphop53 Ser46 (Cell Signaling). Viral p24 was detected using mouse monoclonal anti-HIV1p24 (AIDS Research and Reference Reagent Program, Division of AIDS, NIAID, NIH). HuR was detected using mouse monoclonal anti-HuR 3A2 (Santa Cruz Biotechnology). hnRNPK was detected using goat polyclonal anti-hnRNPK P20 (Santa Cruz Biotechnology). Coverslips were washed 3 times (5 mins each on an orbital shaker) with wash buffer (0.05% Tween20 in PBS), followed by incubation with secondary antibodies conjugated to either Atto550 or Atto565 or Atto647 for 60 mins at room temperature. Coverslips were washed 3 times (5 mins each on an orbital shaker) with wash buffer (0.05% Tween20 in PBS). Coverslips were incubated in equilibration buffer (0.4% glucose, 2×SCC) for 5 mins and counter stained with 1 mg/ml DAPI (4',6-diamidino-2-phenylindole; Life Technologies). Coverslips were mounted in glox buffer (3.7 mg/ml glucose oxidase, 1 U catalase) and imaged.

Quantitative RT-PCR

For each experiment, Ghost(3) cells or IPSO-derived primary macrophages were infected or treated with 500 nM Doxorubicin over time and total RNA was extracted from cells using TRIzol® (Life Technologies), treated with RQ1 RNase-free DNase (Promega) and reverse transcribed using SuperScript III Reverse Transcriptase (Life Technologies). Quantitative RTPCR was performed using Sso Fast EvaGreen™ supermix (BioRad) on a BioRad CFX96 real-time PCR detection system. PCR primer sets used: p53 (forward 5' TGA CAC GCT TCC CTG GAT TG 3' (SEQ ID NO:5), reverse 5' ACC ATC GCT ATC TGA GCA GC 3'(SEQ ID NO:6)), CDKN1A/p21 (forward 5' AGT CAG TTC CTT GTG GAG CC 3' (SEQ ID NO:7), reverse 5' AGG AGA ACA CGG GAT GAG GA 3'(SEQ ID NO:8)), bclxL (forward 5' TAG CCA TCT GTG CCC ACT CT 3' (SEQ ID NO:9), reverse 5' GCT CCA CAC TCC ACA CTA CC 3'(SEQ ID NO:10)), HIV1 Gag (5' GGC CTT CAG CCC AGA AGT AA 3'(SEQ ID NO:11), reverse 5' CTT TAT GGC TGG GTC CTC CC 3'(SEQ ID NO:12), lincRNAp21 (forward 5' CAG GGA ACC CCT TCA ATC CC 3'(SEQ ID NO:13), reverse 5' TTT TTG CCC ACA TGA GCC TG 3' (SEQ ID NO:14)), HuR (forward 5' AGA GCG ATC AAC ACG CTG AA 3' (SEQ ID NO:15), reverse 5' TAA ACG CAA CCC CTC TGG AC 3' (SEQ ID NO:16)) and HPRT (forward 5' GCA GCC CTG GCG TCG TGA TTA 3' (SEQ ID NO:17), reverse 5' CGT GGG GTC CTT TTC ACC AGC A 3' (SEQ ID NO:18)).

Apoptosis Assay

Apoptosis was measured in Ghost(3) cells 30 hours post-infection or drug treatment using the NucView™ 488 Caspase3 Assay Kit (Biotium) in a 96 well format. Data was analysed in MATLAB using a probabilistic region method to measure cell attachment and expressed as percentage cell survival. Notably, as the kit was only available with a 488 nM dye, cells were analysed at the 30 hour time-point to minimise GFP input from the integrated Tat driven reporter. An average of 3000 cells per condition were analysed with the exception of cells treated with Doxorubicin followed by HIV-infection (FIG. 3), cells transfected with lincRNAp21 overexpression constructs followed by Doxorubicin treatment, and cells transfected with full-length lincRNAp21, infected with HIV1 and treated with Nutlin3 (FIG. 25). These latter conditions (⌘) yielded too few attached cells (<20) at 30 hours for similar analysis.

Western Blot

IPSO derived macrophages were infected for 6 or 24 hours followed by lysis in RIPA buffer (50 mM TrisHCl pH 7.5, 150 mM KCl, 1 mM EDTA, 0.5% Triton X100) supplemented with protease inhibitors (Roche) for 30 mins at room temperature on an orbital shaker. Lysates were centrifuged for 10 mins at 9000×g and 4° C., and supernatants were pre-cleared using the same conditions. Total protein was quantified using a Bradford Assay (Sigma), equal concentrations of protein per sample were mixed with sample loading buffer (BioRad), separated by 15% denaturing PAGE and transferred to PVDF. Blots were blocked in 0.8% milk prior to incubation with mouse monoclonal antiHIV1p24 (AIDS Research and Reference Reagent Program, Division of AIDS, NIAID, NIH) or anti-actin C11 (Santa Cruz Biotechnology) antibodies. Appropriate secondary antibodies were detected by chemiluminescence using an ECL kit (BioRad) according to the manufacturer's protocol.

Imaging and Analysis

Cells were imaged on a custom built Nikon Ti Eclipse wide-field TIRF microscope using a 100×N.A. 1.49 Nikon Apochromat TIRF oil immersion objective. Imaging was done using mercury lamp illumination through the appropriate filter sets at low camera gain in each of the fluorescent channels using an Andor iXion897 EMCCD camera cooled to 80° C. The microscope was controlled using µmanager open source microscope management software (NIH and UCSF, USA). A 30 ms exposure time was used for DAPI.

Exposure times ranged from 200 to 500 ms for other dyes. Each field of view was captured as a series of images acquired on multiple focal planes through the samples, across a range of 210 mm in the axial plane. A 0.2 mm piezo step-size was used for z-stacks. Signal intensities were measured using the methods of Fiji. The contrast of images shown was adjusted to fit a 16 bit gray scale.

DISCUSSION

Figure 1:
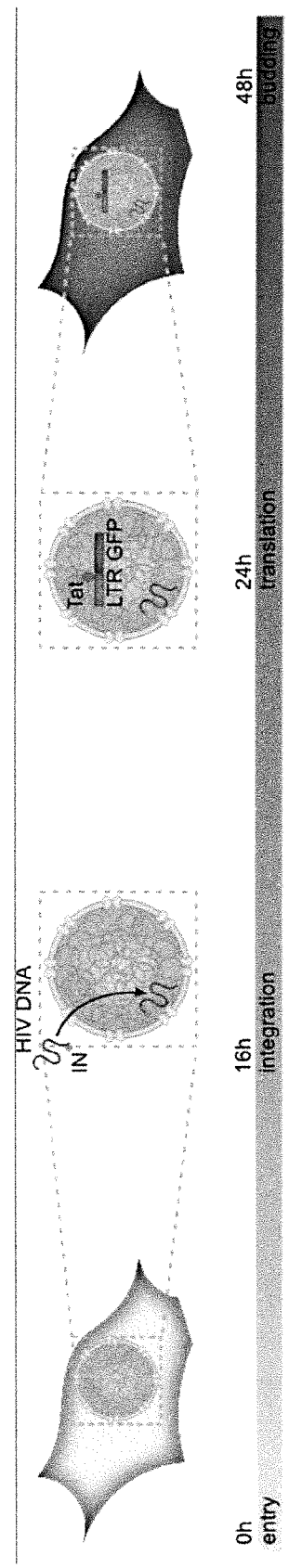
FIG. 1: HIV1 induces DSBs during integration but evades cellular apoptosis by masking DNA damage.

To investigate how HIV1 induces DSBs yet manages to evade the cellular apoptotic response, we used macrophages (induced pluripotent stem cell (iPSC) derived macrophages) and Ghost(3) cells, which contain an integrated fluorescent reporter transcriptionally driven by the HIV LTR promoter. Following integration, host-mediated production of the HIV1 Tat protein drives processive transcription from the integrated viral LTR promoter. Tat also binds the LTR promoter driving the fluorescent reporter in Ghost(3) cells, allowing transcriptional activation to be monitored in real-time in the presence of HIV1 (FIG. 1). Typically, HIV1 integration occurs approximately 16 hours post-infection and Tat-mediated activation of an integrated LTR-reporter can be detected from approximately 18 hours post-infection culminating in maximum GFP expression and HIV1 Gag production at 48 hours. When using physiologically relevant macrophages that do not contain an HIV-specific reporter, viral p24 capsid protein can be detected by immunofluorescence and western blot at earlier time points as compared to reporter cells.

We infected macrophages and Ghost(3) cells with HIV1 BaL.01 and visualized DSBs by immunofluorescent staining for H2A.X. This histone variant is rapidly recruited to DSBs where it is phosphorylated at Ser139 within minutes and persists until the DSB is repaired. By concurrently assessing the production of activated caspase 3 as a marker of apoptosis induction (shown as percentage cell survival), we were able to determine that despite inducing multiple DSBs within 24 hours, apoptosis does not occur in HIV-infected cells (FIG. 2). A similar effect was also observed in HIV-infected macrophages. Consistent with other studies, a lethal dose of Doxorubicin induced extensive H2A.X staining within 8 hours of treatment followed by apoptosis at 48 hours (FIG. 2). We were able to abrogate this effect with the integrase (IN) inhibitor Raltegravir, revealing that the integration event itself is required to induce H2A.X staining in infected cells.

Since HIV-infected cells generated DSBs but did not undergo apoptosis and supported successful viral replication, we reasoned that only a portion of the cellular DSB surveillance mechanism may be intact. Thus infection may protect cells from apoptosis in the presence of additional lethal concentrations of chemical DNA damaging agents. To ascertain this, we repeated the prior experiment adding a lethal dose of Doxorubicin after HIV1 infection (FIG. 3). Cells that received Doxorubicin prior to HIV1 infection underwent apoptosis. Surprisingly, cells infected 24 hours before being exposed to the same duration of Doxorubicin treatment were protected from apoptosis (60% survival vs 32% survival for Doxo. only) and supported viral replication. These striking data suggested that while HIV1 integration induces DSBs, the virus is able to decouple the DNA damage surveillance mechanism from the apoptotic response in infected cells. Furthermore, the protection afforded by infection persisted despite additional challenges to the genomic integrity of cells.

The cellular response to DSBs is exquisitely sensitive and damage is recognized by members of the phosphoinositide3kinase-related protein kinases (PIKKs) family including Ataxia-telangiectasia mutated (ATM) which is recruited to DSBs by the Mre11Rad50Nbs1 (MRN) complex and activated by auto phosphorylation of Ser1981. A key downstream target of ATM is p53, which is phosphorylated at multiple residues including Ser46. Phosphorylation at Ser46 specifically directs cellular responses towards apoptosis. As DSBs are known to trigger ATM and p53 activation, we assessed their phosphorylation states in response to viral and chemical agent-induced DNA damage. Doxorubicin treatment resulted in the phosphorylation of both ATMpSer1981 and p53pSer46 in the nucleus within 8 hours (FIGS. 4 and 5). In contrast, HIV1 infection did not lead to activation of either of these residues over 48 hours (FIGS. 4 and 5). Quantitative real-time RTPCR analysis revealed that p53 expression was significantly decreased during the same time course in the presence of virus (FIG. 6). CDKN1A/p21, the major cell cycle arrest factor induced by p53 was also reduced during HIV1 infection (FIG. 6). This latter observation combined with the absence of apoptosis-specific marks in HIV-infected cells provides further evidence that the virus is able to carefully orchestrate the cellular response to DSBs, thereby avoiding apoptosis.

Figure 8:
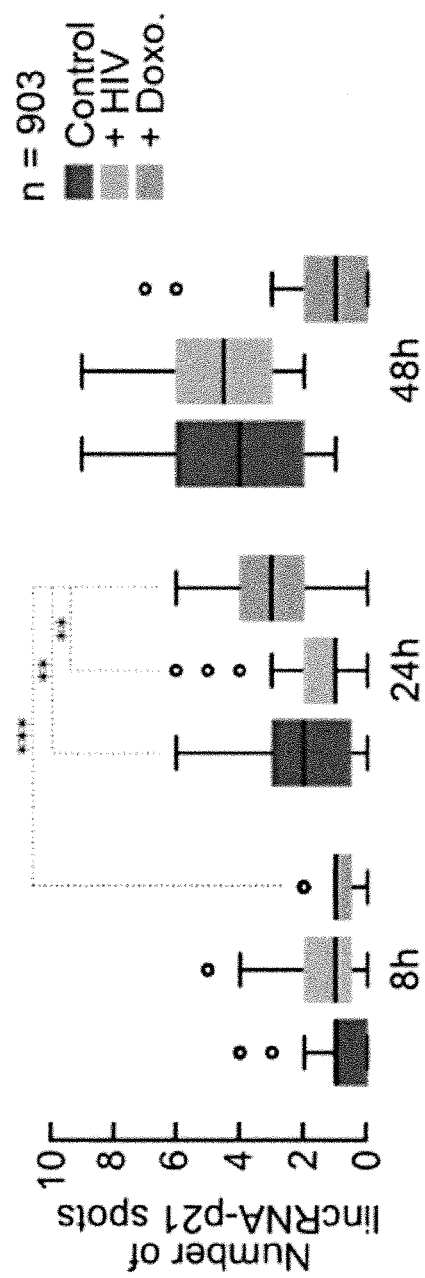

A critical portion of the p53-mediated apoptotic transcriptional response was recently shown to be controlled by the long intergenic noncoding RNA lincRNAp21. In response to DNA damage, p53 transcriptionally activates lincRNAp21 which is located on chromosome 6 upstream of CDKN1A/p21 in human cells (FIG. 7). Since HIV1 had neutralised the apoptotic response, we examined the status of lincRNAp21 in HIV-infected and control cells. We designed RNA FISH probes to target the first and second exons of lincRNAp21 and each set was conjugated to spectrally distinct fluorophores. RNA FISH revealed that both exons co-localize within the nucleus of cells. As previously noted, lincRNAp21 was enhanced in Doxorubicin-treated cells, but HIV-induced DNA damaged cells showed no increase in lincRNAp21 expression as measured by smFISH spot count analysis and qRTPCR (FIGS. 8 and 9). Unsurprisingly, no change in lincRNAp21 expression was observed in cells treated with Raltegravir (FIG. 10).

The cellular response to DNA damage involving p53 includes a robust regulation of gene expression at the posttranscriptional level by RNA-binding proteins (RBPs) and microRNAs. While many RBPs associate with mRNAs and increase their stability in response to cellular stress, it was recently shown that the RBP HuR/ELAV1 associated with lincRNAp21 in the nucleus and decreased its stability through the recruitment of Ago2 and the let7 microRNA. We hypothesized that HIV1 may co-opt this pathway to decrease lincRNAp21 expression in infected cells. Unexpectedly, we observed a significant difference in the cellular location of HuR in cells infected with HIV1 as compared to chemically induced DSBs (FIG. 11). In Doxorubicin treated cells, HuR moved from the nucleus into the cytoplasm within 8 hours of treatment, consistent both with its role in mRNA stabilization and our observed increase in lincRNAp21 expression (FIG. 9). However, despite HIV1 integration and concomitant induction of DSBs occurring approximately 16 hours post infection (as visualized by H2A.X staining in FIG. 2), HuR failed to localize in the cytoplasm of HIV-infected cells at this time (FIG. 11).

Since HIV infected cells failed to respond apoptotically to lethal levels of chemically induced DNA damage and lincRNAp21 levels were lowered by nuclear resident HuR, we reasoned that we could reverse the decline in lincRNAp21 levels by silencing HuR. We delivered siRNAs targeted to HuR in HIV infected cells and observed a rise in lincRNAp21 as detected by qRTPCR (FIGS. 12 and 13). However, siHuR treated cells continued to support HIV1 replication to the same extent as untreated cells (FIG. 14). These data suggested that although the virus manipulates HuR location in order to control lincRNAp21 expression, this alone could not account for the block in apoptosis observed in infected cells. In support of this, exogenously overexpressed full-length lincRNAp21 was decreased in HIV infected cells (FIGS. 15 and 16) and did not lead to apoptosis as observed for similarly treated Doxorubicin-induced DNA damaged cells. Collectively these data pointed to additional molecular mechanisms by which HIV1 is able to evade apoptosis.

LincRNAp21 acts within the p53-mediated apoptosis pathway by physically associating with hnRNPK in the nucleus of cells and localizing the protein to promoters of p53 repressed genes, in cis and in trans. The interplay between p53, lincRNAp21 and hnRNPK ensures repression of a specific set of genes that are part of the p53 DNA damage response. Key to this repression is the formation of a lincRNAp21-hnRNPK interaction in the nucleus. Thus by interacting with, and altering the localisation of hnRNPK, lincRNAp21 controls cellular apoptosis in response to DNA damage including DSBs. As lincRNAp21 is negatively regulated under normal conditions by HuR in the nucleus of cells, the balance of interactions between this lincRNA and its protein binding partners allow for regulation of cellular apoptosis (FIG. 17). Since nuclear localization of hnRNPK is required for its repressive function, and as HIV1 is able to avoid apoptosis, we hypothesised that in addition to reducing nuclear levels of lincRNAp21, the virus was altering hnRNPK's location within infected cells. We monitored hnRNPK at several time points following DNA damage induced either by Doxorubicin treatment or HIV1 infection (FIG. 18). Notably, hnRNPK was detected in the nucleus of Doxorubicin-treated cells between 2 and 4 hours post-treatment and by 24 hours, cells were apoptotic. Remarkably, hnRNPK remained cytoplasmic in HIV-infected cells throughout the duration of the time course and no apoptosis occurred. Furthermore, this effect was also observed in infected macrophages (FIG. 19) revealing the same response in physiologically relevant cells. This observation parsimoniously explained the inability to trigger transcription of genes, since hnRNPK is unable to associate with lincRNAp21 in the nucleus. Furthermore, it explained why the addition of exogenous lincRNAp21 is unable to cause apoptosis in HIV-infected cells.

We deepened these observations using antiretroviral therapeutics that target discrete points in the viral life cycle. Cells exposed to HIV1 and concurrently treated with Maraviroc, a CCR5 antagonist that prevents viral entry, remained uninfected and showed no nuclear hnRNPK. Similarly, cells exposed to HIV1 and concurrently treated with Tenofovir, a reverse transcriptase inhibitor (NRTI), showed no nuclear hnRNPK. Finally, cells exposed to HIV1 and concurrently treated with Raltegravir to inhibit integration, showed no nuclear hnRNPK over time (FIG. 20). Importantly, the localisation of hnRNPK in these cells was expected as they had not been exposed to DNA damage. Thus we repeated the same experiments with the addition of Doxorubicin 24 hours post concurrent infection and drug treatment. In all cases, hnRNPK localized to the nucleus and the cells underwent apoptosis (FIG. 20). Taken together, these data reveal that integration, as opposed to the presence of incoming proviral DNA or any of the associated HIV1 proteins, is required for the virus to exclude hnRNPK from the nucleus. In addition, these data suggest that HIV1 is able to block the association of lincRNAp21 and hnRNPK, thereby negating the proper localization required for transcriptional repression, and evade apoptosis (FIG. 21).

Figure 22:
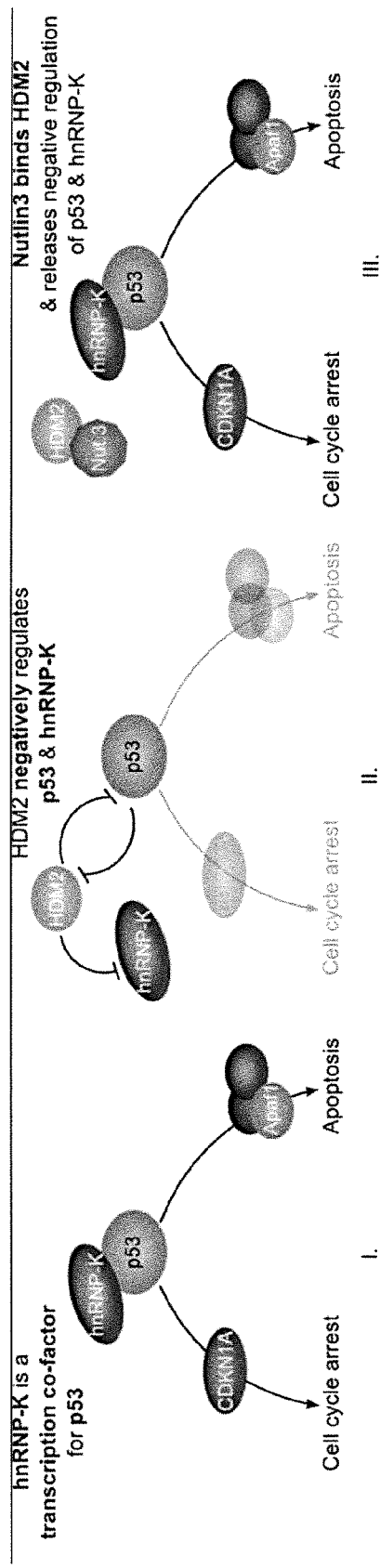

To conclusively demonstrate that the sequestration of hnRNPK in the cytoplasm by HIV1 coupled to an HuR-mediated reduction in lincRNAp21 levels is the mechanism by which HIV1 evades apoptosis, we designed an experiment by which we would restore hnRNPK to the nucleus during HIV1 infection and concurrently boost lincRNAp21 levels. We reasoned that overcoming this block would help to re-establish hnRNPK's interaction with lincRNAp21 and trigger cellular apoptosis in infected cells. DNA damage signaling culminates in hnRNPK activation chiefly through inhibition of its ubiquitin-mediated degradation by the E3 ligase HDM2. Both p53 and hnRNPK are thus activated in response to DNA damage and both are negatively regulated through the action of HDM2. Nutlin3a is a small molecule inhibitor that activates p53 by binding to HDM2. As Nutlin3a had previously been linked to activation of hnRNPK, we hypothesized that treatment with this inhibitor may allow hnRNPK to move into the nucleus of HIV-infected cells (FIG. 22). Control cells treated with Nutlin3a in the absence of any DNA damage showed no nuclear hnRNPK (FIG. 23) revealing that even if the negative regulation mediated by HDM2 is released, DNA damage is still required to trigger nuclear localization of hnRNPK. In contrast, Nutlin3a treatment following 24 hours of infection resulted in nuclear localisation of hnRNPK in HIV-infected cells only (FIG. 23). This result demonstrates that the addition of Nutlin3a after infection is sufficient to prevent the virus from excluding hnRNPK from the nucleus. We also observed that when Nutlin3a was added prior to HIV1 infection, no nuclear hnRNPK was observed. This suggests that post-integration, the virus loses the capacity to counteract the effects of Nutlin3a and further implicates the components involved in the integration event itself in viral mediated control of hnRNPK nuclear localisation.

Though Nutlin3a treatment could lead to nuclear localisation of hnRNPK in the presence of HIV1, we sought to combine this effect with elevated lincRNAp21 expression. Since HIV1 infection lowers lincRNAp21 levels by HuR mediated degradation (FIGS. 8, 9, 15 and 16), overcoming the nuclear exclusion of hnRNPK is insufficient to induce apoptosis if lincRNAp21 levels are not concomitantly up-regulated. We had previously observed that overexpressed lincRNAp21 did not lead to apoptosis in HIV infected cells and further determined that there was no nuclear localisation of hnRNPK in these cells. We then sought to verify that the combination of overexpressed lincRNAp21 and Nutlin3a in the absence of HIV1 did not lead to nuclear localisation of hnRNPK and apoptosis. We transfected cells for 24 hours with either the full-length or truncated lincRNAp21 sequences followed by the addition of Nutlin3a and observed cytoplasmic hnRNPK and no apoptosis under both conditions. Finally, we transfected cells for 24 hours with either the full-length or truncated lincRNAp21 sequences, infected for 24 hours, followed by Nutlin3a treatment. In the presence of the full-length lincRNAp21 construct only, HIV-infected cells treated with Nutlin3a showed nuclear hnRNPK and underwent apoptosis (FIG. 24). Similarly treated cells that received the truncated version of lincRNAp21, which is unable to bind hnRNPK, also showed nuclear hnRNPK but did not undergo apoptosis (FIG. 24). Together, these results indicate that restoring nuclear hnRNPK in the presence of elevated levels of full-length lincRNAp21 leads to apoptosis in HIV-infected cells.

Our findings demonstrate the deliberate and focused attack HIV1 aims at lincRNAp21 to mask IN-induced DSBs and evade cellular apoptosis (FIG. 1 to 6). This virus does so by hijacking cellular HuR to degrade lincRNAp21 (FIG. 7 to 16) and cripples its association with the nuclear protein binding partner hnRNPK (FIG. 17 to 21) by spatially separating the two molecules. Appropriate interaction between lincRNAp21 and hnRNPK can be restored through the combined action of Nutlin3a and overexpressed lincRNAp21 (FIG. 22 to 25). We propose a model (FIG. 25) in which proviral integration does not lead to complete p53 activation, specifically phosphorylation of Ser46 (FIG. 1 to 6), and thus transcription of proapoptotic lincRNAp21 is suppressed. In addition, by physically altering the location of both of lincRNAp21's protein binding partners (HuR and hnRNPK) in response to integration, HIV1 is able to control cellular apoptosis. Overexpression of lincRNAp21 and addition of Nutlin3a in the presence of infection support this possibility (FIGS. 7 to 16 and 22 to 25). These findings also highlight that three discrete but tightly coordinated events are required for apoptosis to occur. Firstly, DNA damage such as DSBs must lead to complete activation of p53 such that downstream transcription of associated targets is initiated. Secondly, lincRNAp21 expression levels must be enhanced. This is connected to p53 activation and HuR-mediated degradation but can be bypassed through exogenous overexpression. Third and lastly, hnRNPK must translocate to the nucleus to ensure its association with lincRNAp21 and subsequent suppression of pro-survival genes. An absence of any one of these events is sufficient for the evasion of apoptosis as summarised by our findings.

While it is not unusual for pathogens to manipulate host signalling pathways, our data illuminate a unique strategy whereby HIV1 is able to control the cellular response to DNA damage via a long noncoding RNA. We hypothesise that the virus is mediating such a controlled effect on the two proteins, HuR and hnRNPK via manipulation of shared members of the kinase family responsible for phosphorylating both HuR and hnRNPK. It has been observed that Adenovirus onco-proteins are able to inactivate the DNA repair MRN complex at viral replication centers, masking host genome instabilities that are instigated by this generally non-integrative DNA virus. Furthermore, the phosphorylation of p53 at key residues, required to ensure its stabilization as well as to facilitate DNA binding, is also inhibited in adenovirus-infected cells. Intriguingly, in the presence of exogenous genotoxic stress, p53 was phosphorylated at multiple residues and thus stabilized to a greater extent than untreated cells, but the presence of adenovirus ensured that p53 failed to activate downstream transcription. As the constitutive expression of p53 in the absence of DNA damage is controlled through HDM2-mediated degradation, the phosphorylation of p53 is synonymous with its resistance to such degradation and transcription of downstream effectors. Given that viruses contribute to 20% of cancers worldwide, it is important to understand how genomic instabilities are propagated following challenge, as well as how apoptosis is evaded. While HIV1 itself does not cause cancer, our observations that HIV-mediated resistance to apoptosis occurs through manipulation of a host long noncoding RNA and its protein binding partners, reveals a novel mechanism whereby genomic integrity can be severely challenged yet the cells survive. Thus HIV1 may be an informative tool in the study of human malignancies. Finally, our data provide a glimpse of how pathogens with limited coding capacity can significantly restructure major cellular pathways using lncRNAs, thereby adding a new layer of complexity to host-pathogen interactions.

EXAMPLE 2

Cell Culture

Ghost(3) cells (AIDS Research and Reference Reagent Program, Division of AIDS, NIAID, NIH) were cultured in DMEM (Invitrogen) supplemented with 10% heat-inactivated fetal bovine serum (FBS; Biochrom), 0.2 mM GlutaMAX™ (Life Tech), 500 µg/mL G418 (Sigma), 100 µg/mL Hygromycin (Sigma) and 1 µg/mL Puromycin (Sigma). Mouse NIH3T3 cells (AIDS Research and Reference Reagent Program, Division of AIDS, NIAID, NIH) were cultured in DMEM-F12 (Invitrogen) supplemented with 10% heat-inactivated FBS and 0.2 mM GlutaMAX™ (Life Tech). HEK293T and TZM-BI cells (AIDS Research and Reference Reagent Program, Division of AIDS, NIAID, NIH) were cultured in DMEM (Invitrogen) supplemented with 10% heat-inactivated FBS. Macrophages were derived from induced pluripotent stem cells, characterised and cultured in X-Vivo-15 media (Lonza) supplemented with 1× Glutamax (Invitrogen), 50 µM β-mercaptoethanol (Sigma), 25 ng/mL IL-3 (Invitrogen) and 100 ng/mL M-CSF (Peprotech).

Viral Plasmids, Virus Stocks, Infections and Drugs

Viral stocks were generated by co-transfecting HEK293T cells with HIV-1 clones BaL.01 and pSG3Δenv (AIDS Research and Reference Reagent Program, Division of AIDS, NIAID, NIH) using Fugene6 (Roche). Supernatants were collected 48 hours post-transfection, supplemented with FBS to a final concentration of 20% and stored in aliquots at −80° C. Viral stocks were titred using TZM-BI cells and used to infect Ghost(3) cells using an MOI=1.0, or IPSO-derived macrophages using an MOI=0.5. Where indicated, cells were treated with 10 µM of either Raltegravir, Maraviroc, Tenofovir (AIDS Research and Reference Reagent Program, Division of AIDS, NIAID, NIH) or Doxorubicin (Sigma-Aldrich), or Nutlin3a (Sigma-Aldrich), or MAP2K1 inhibitor (U-0126) or ERK2 inhibitor (FR180204) for up to 48 hours.

Cloning and Transfections

Ghost(3) cells were transfected for 48 hours prior to infection with 25 nM (final concentration) of ON-TARGETplus human HuR/ELAV1 siRNA SMARTpool (5' GAC AAA AUC UUA CAG GUU U 3' (SEQ ID NO:1), 5' GAC AUG UUC UCU CGG UUU G 3' (SEQ ID NO:2), 5' ACA AAU AAC UCG CUC AUG C 3' (SEQ ID NO:3), 5' GCU CAG AGG UGA UCA AAG A 3' (SEQ ID NO:4); ThermoScientific) using RNAiMax (Invitrogen). Mouse full-length lincRNA-p21 (3073 bp) (GenBank Accession Number: HM210889) and truncated lincRNA-p21 (1889 bp) sequences were synthesised (GeneArt, Life Technologies) and sub-cloned via 5' SacI and 3' EcoRI into pCi-Neo (Promega). Ghost(3) cells were transfected for 21 hours prior to infection with either construct using Lipofectamine2000 (Invitrogen).

Immunofluorescence

For each experiment, cells were infected or treated with drugs on coverslips, fixed for 10 mins in fresh 4% paraformaldehyde at room temperature, then washed 3 times in PBS and permeabilised for 10 mins in ice-cold methanol at −20° C. Coverslips were washed once in PBS and incubated in blocking buffer (5% goat serum, 0.3% Triton-X100 in PBS) for 60 mins at room temperature. Cells were incubated in primary antibody solution (1% BSA, 0.3% Triton X-100 in PBS) overnight at 4° C. Double strand breaks were detected using rabbit polyclonal anti-phospho-histone H2A.X Ser139 (Cell Signaling). Activated ATM was detected using rabbit monoclonal anti-phospho-ATM Ser1981 (Cell Signaling). The ability of p53 to regulate apoptosis was detected using rabbit polyclonal anti-phospho-p53 Ser46 (Cell Signaling). Viral p24 was detected using mouse monoclonal anti-HIV-1-p24 (AIDS Research and Reference Reagent Program, Division of AIDS, NIAID, NIH). HuR was detected using mouse monoclonal anti-HuR 3A2 (Santa Cruz Biotechnology). hnRNP-K was detected using goat polyclonal anti-hnRNP-K P-20 (Santa Cruz Biotechnology). Coverslips were washed 3 times (5 mins each on an orbital shaker) with wash buffer (0.05% Tween-20 in PBS), followed by incubation with secondary antibodies conjugated to either Atto-550 or Atto-565 or Atto-647 for 60 mins at room temperature. Coverslips were washed 3 times (5 mins each on an orbital shaker) with wash buffer (0.05% Tween-20 in PBS). Coverslips were incubated in equilibration buffer (0.4% glucose, 2×SCC) for 5 mins and counter stained with 1 mg/ml DAPI (4',6-diamidino-2-phenylindole; Life Technologies). Coverslips were mounted in glox buffer (3.7 mg/ml glucose oxidase, 1 U catalase) and imaged.

Quantitative RT-PCR

For each experiment, cells were infected or treated with drugs over time and total RNA was extracted from cells using TRIzol® (Life Technologies), treated with RQ1 RNase-free DNase (Promega) and reverse transcribed using SuperScript III Reverse Transcriptase (Life Technologies). Quantitative RT-PCR was performed using Sso Fast EvaGreen™ supermix (BioRad) on a Bio-Rad CFX96 real-time PCR detection system. PCR primer sets used: p53 (forward 5' TGA CAC GCT TCC CTG GAT TG 3' (SEQ ID NO:5), reverse 5' ACC ATC GCT ATC TGA GCA GC 3' (SEQ ID NO:6)), CDKN1A/p21 (forward 5' AGT CAG TTC CTT GTG GAG CC 3' (SEQ ID NO:7), reverse 5' AGG AGA ACA CGG GAT GAG GA 3' (SEQ ID NO:8)), bcl-xL (forward 5' TAG CCA TCT GTG CCC ACT CT 3' (SEQ ID NO:9), reverse 5' GCT CCA CAC TCC ACA CTA CC 3' (SEQ ID NO:10)), HIV-1 Gag (5' GGC CTT CAG CCC AGA AGT AA 3' (SEQ ID NO:11), reverse 5' CTT TAT GGC TGG GTC CTC CC 3' (SEQ ID NO:12)), lincRNA-p21 (forward 5' CAG GGA ACC CCT TCA ATC CC 3' (SEQ ID NO:13), reverse 5' TTT TTG CCC ACA TGA GCC TG 3' (SEQ ID NO:14)), HuR (forward 5' AGA GCG ATC AAC ACG CTG AA 3' (SEQ ID NO:15), reverse 5' TAA ACG CAA CCC CTC TGG AC 3' (SEQ ID NO:16)) and HPRT (forward 5' GCA GCC CTG GCG TCG TGA TTA 3' (SEQ ID NO:17), reverse 5' CGT GGG GTC CTT TTC ACC AGC A 3' (SEQ ID NO:18)).

Apoptosis Assay

Apoptosis was measured in Ghost(3) cells 30 hours post-infection or drug treatment using the NucView™ 488 Caspase-3 Assay Kit (Biotium) in a 96 well format. Data was analysed in MATLAB using a probabilistic region method to measure cell attachment and expressed as percentage cell survival. Notably, as the kit was only available with a 488 nM dye, cells were analysed at the 30 hour time-point to minimise GFP input from the integrated Tat-driven reporter. An average of 3000 cells per condition were analysed with the exception of cells treated with Doxorubicin followed by HIV-infection (FIG. 27), cells transfected with lincRNA-p21 overexpression constructs followed by Doxorubicin treatment (FIG. 36), and cells transfected with full-length lincRNA-p21, infected with HIV-1 and treated with Nutlin3 (FIG. 45). These latter conditions (⚌) yielded too few attached cells (<20) at 30 hours for similar analysis.

Western Blot

IPSO-derived macrophages were infected for 6 or 24 hours followed by lysis in RIPA buffer (50 mM Tris-HCl pH 7.5, 150 mM KCl, 1 mM EDTA, 0.5% Triton X-100) supplemented with protease inhibitors (Roche) for 30 mins at room temperature on an orbital shaker. Lysates were centrifuged for 10 mins at 9000×g and 4° C., and supernatants were pre-cleared using the same conditions. Total protein was quantified using a Bradford Assay (Sigma), equal concentrations of protein per sample were mixed with sample loading buffer (BioRad), separated by 15% denaturing PAGE and transferred to PVDF. Blots were blocked in 0.8% milk prior to incubation with mouse monoclonal anti-HIV-1-p24 (AIDS Research and Reference Reagent Program, Division of AIDS, NIAID, NIH) or mouse monoclonal anti-active and pro-caspase 3 (Abcam) or anti-actin C-11 (Santa Cruz Biotechnology) antibodies. Appropriate secondary antibodies were detected by chemiluminescence using an ECL kit (BioRad) according to the manufacturer's protocol.

Imaging and Analysis

Cells were imaged on a custom built Nikon Ti Eclipse widefield TIRF microscope using a 100×N.A. 1.49 Nikon Apochromat TIRF oil immersion objective. Imaging was done using mercury lamp illumination through the appropriate filter sets at low camera gain in each of the fluorescent channels using an Andor iXion897 EMCCD camera cooled to −80° C. The microscope was controlled using μmanager open source microscope management software (NIH and UCSF, USA). A 30 ms exposure time was used for DAPI. Exposure times ranged from 200 to 500 ms for other dyes. Each field of view was captured as a series of images acquired on multiple focal planes through the samples, across a range of 2-10 mm in the axial plane. A 0.2 mm piezo step-size was used for z-stacks. Signal intensities were measured using Fiji31 (Schindelin). The contrast of images shown was adjusted to fit a 16 bit gray scale.

HIV-1 Masks DNA Damage and Prevents lincRNA-p21 Up-Regulation

To investigate how HIV-1 induces DSBs yet manages to evade the cellular apoptotic response, we used macrophages (induced pluripotent stem cell (iPSC)-derived macrophages) and Ghost(3) cells, which contain an integrated fluorescent reporter transcriptionally driven by the HIV LTR promoter. Following integration, host-mediated production of the HIV-1 Tat protein drives processive transcription from the integrated viral LTR promoter. Tat also binds the LTR promoter driving the fluorescent reporter in Ghost(3) cells, allowing transcriptional activation to be monitored in real-time in the presence of HIV-1 (FIG. 1). Typically, HIV-1 integration occurs approximately 16 hours post-infection and Tat-mediated activation of an integrated LTR-reporter can be detected from approximately 18 hours post-infection culminating in maximum GFP expression and HIV-1 Gag production at 48 hours. When using physiologically relevant macrophages that do not contain an HIV-specific reporter, viral p24 capsid protein can be detected by immunofluorescence and western blot at earlier time points as compared to reporter cells.

As HIV-1 infection does not generally lead to apoptosis in macrophages and chronically infected U937 monocyte-like cells are more resistant to DNA-damaging agents, we reasoned that only a portion of the cellular DSB surveillance mechanism may be intact in the presence of virus. To ascertain this, we added a lethal dose of Doxorubicin after infection of macrophages and Ghost(3) cells with HIV-1 BaL.01, and visualized DSBs by immunofluorescent staining for H2A.X (FIG. 27). This histone variant is rapidly recruited to DSBs where it is phosphorylated at Ser139 within minutes and persists until the DSB is repaired. By concurrently assessing the production of activated caspase 3 as a marker of apoptosis induction (shown as percentage cell survival), we observed that cells which received Doxorubicin prior to HIV-1 infection underwent apoptosis. However, cells infected 24 hours before being exposed to the same duration of Doxorubicin treatment were protected from apoptosis (60% survival vs 32% survival for Doxo. only) and supported viral replication. These striking data suggested that the virus is able to decouple the DNA damage surveillance mechanism from the apoptotic response in infected cells. In addition the protection from apoptosis afforded by infection persists despite additional challenges to the genomic integrity of cells.

The cellular response to DSBs is exquisitely sensitive and damage is recognized by members of the phosphoinositide-3-kinase-related protein kinases (PIKKs) family including Ataxia-telangiectasia mutated (ATM) which is recruited to DSBs by the Mre11-Rad50-Nbs1 (MRN) complex and activated by auto phosphorylation of Ser1981. A key downstream target of ATM is p53, which is phosphorylated at multiple residues including Ser46. Phosphorylation at Ser46 specifically directs cellular responses towards apoptosis. As DSBs are known to trigger ATM and p53 activation, we assessed their phosphorylation states in response to viral and chemical agent-induced DNA damage. Doxorubicin treatment resulted in the phosphorylation of both ATMpSer1981 and p53pSer46 in the nucleus within 8 hours (FIGS. 28 and 29). In contrast, HIV-1 infection did not lead to activation of either of these residues over 48 hours (FIGS. 28 and 29). Quantitative real-time RT-PCR analysis revealed that p53 expression was significantly decreased during the same time course in the presence of virus (FIG. 30 upper panel). CDKN1A/p21, the major cell cycle arrest factor induced by p53 was also reduced during HIV-1 infection (FIG. 30 lower panel). This latter observation combined with the absence of apoptosis-specific marks in HIV-infected cells provides further evidence that the virus is able to carefully orchestrate the cellular response to DSBs, thereby avoiding apoptosis.

A critical portion of the p53-mediated apoptotic transcriptional response was recently shown to be controlled by the long intergenic noncoding RNA lincRNA-p21. In response to DNA damage, p53 transcriptionally activates lincRNA-p21 which is located on chromosome 6 upstream of CDKN1A/p21 in human cells (FIG. 30). Since HIV-1 had neutralised the apoptotic response, we examined the status of lincRNA-p21 in HIV-infected and control cells. As previously noted, lincRNA-p21 was enhanced in Doxorubicin-treated cells, but HIV-induced DNA damaged cells showed no increase in lincRNA-p21 expression (FIG. 31). The implication of this finding is that HIV-1 is able to prevent apoptosis by regulating lincRNA-p21.

HIV-1 Manipulates lincRNA-p21's Protein Binding Partners

LincRNA-p21 acts within the p53-mediated apoptosis pathway by physically associating with hnRNP-K in the nucleus of cells and localising the protein to promoters of p53-repressed genes, in cis and in trans. As lincRNA-p21 is negatively regulated under normal conditions by HuR/ELAV1 in the nucleus of cells, the balance of interactions between this lincRNA and its protein binding partners allow for regulation of cellular apoptosis (FIG. 33). HuR association with lincRNA-p21 decreases its stability through the recruitment of Ago2 and the let-7 microRNA. We hypothesised that HIV-1 may co-opt this pathway to decrease lincRNA-p21 expression in infected cells. Unexpectedly, we observed a significant difference in the cellular location of HuR in cells infected with HIV-1 as compared to chemically induced DSBs (FIG. 34). In Doxorubicin-treated cells, HuR moved from the nucleus into the cytoplasm within 8 hours of treatment, consistent both with its role in mRNA stabilisation and our observed increase in lincRNA-p21 expression (FIG. 31). However, despite HIV-1 integration and concomitant induction of DSBs (as visualized by H2A.X staining in, HuR failed to localise in the cytoplasm of HIV-infected cells at this time (FIG. 34).

Since HIV-infected cells failed to respond apoptotically to lethal levels of chemically-induced DNA damage and lincRNA-p21 levels were lowered by nuclear resident HuR, we reasoned that silencing HuR should permit the levels of lincRNA-p21 to be sufficiently elevated to trigger apoptosis. We delivered siRNAs targeted to HuR in HIV-infected cells and observed a rise in lincRNA-p21 as detected by qRT-PCR (FIG. 35 left panel). However, siHuR-treated cells continued to support HIV-1 replication to the same extent as untreated cells (FIG. 35 right panel). These data suggested that although the virus manipulates HuR location in order to control lincRNA-p21 expression, this alone could not account for the block in apoptosis observed in infected cells. In support of this, exogenously overexpressed full-length lincRNA-p21 was decreased in HIV-infected cells (FIG. 36 left panel) and did not lead to apoptosis as observed for similarly treated Doxorubicin-induced DNA damaged cells (FIG. 36 right panel). Collectively these data pointed to additional molecular mechanisms by which HIV-1 is able to evade apoptosis.

The interplay between p53, lincRNA-p21 and hnRNP-K ensures repression of a specific set of genes that are part of the p53 DNA damage response. Key to this repression is the formation of a lincRNA-p21-hnRNP-K interaction in the nucleus. Thus by interacting with, and altering the localisation of hnRNP-K, lincRNA-p21 controls cellular apoptosis in response to DNA damage including DSBs. Since nuclear localisation of hnRNP-K is required for its repressive function, and as HIV-1 is able to avoid apoptosis, we hypothesised that in addition to reducing nuclear levels of lincRNA-p21, the virus was altering hnRNP-K's location within infected cells. We monitored hnRNP-K at several time points following DNA damage induced either by Doxorubicin treatment or HIV-1 infection (FIGS. 37 and 38). Notably, hnRNP-K was detected in the nucleus of Doxorubicin-treated cells between 2 and 4 hours post-treatment and by 24 hours, cells were apoptotic. Remarkably, hnRNP-K remained cytoplasmic in HIV-infected cells throughout the duration of the time course and no apoptosis occurred. This observation parsimoniously explained the inability to trigger transcription of proapoptotic genes, since hnRNP-K is unable to associate with lincRNA-p21 in the nucleus. Furthermore, it explained why the addition of exogenous lincRNA-p21 is unable to cause apoptosis in HIV-infected cells (FIG. 39).

HIV-1 Requires MEK1 and ERK2 to Ensure hnRNP-K's Cytoplasmic Localisation

The cytoplasmic localisation of hnRNP-K is dependent on the action of ERK2-mediated phosphorylation, which in turn is activated specifically by MAP2K1. In addition, MAP2K1-activated ERK2 phosphorylates HDM2, resulting in ubiquitin-mediated degradation of hnRNP-K and p53. Constitutive activation of MAP2K1 results in cytoplasmic accumulation of hnRNP-K, while inhibition of MAP2K1 or ERK2 abolishes this localisation (FIG. 40). As the active MAP2K1/ERK2 cascade maintains cytoplasmic hnRNP-K in healthy cells, while MAP2K1 transcription is negatively regulated by lincRNA-p21/hnRNP-K as part of the proapoptosis pathway, we sought to determine if HIV-1 secures cellular survival via MAP2K1/ERK2.

Immunofluorescence of hnRNP-K in HIV-infected cells exposed to either a MAP2K1 or ERK2 inhibitor revealed a strong nuclear localisation of hnRNP-K and infected cells underwent apoptosis. This result suggested that the virus requires both MAP2K1 and ERK2 to secure the prosurvival pathway, but did not reveal which of the two is specifically targeted by HIV-1. ERK2 was the most likely candidate due to its known interaction with the (preintegration complex) PIC. However, our experiments were specifically conducted 30 hours post-infection with clone BaL.01 to ensure integration of HIV-1 had already successfully occurred (as confirmed by GFP expression in Ghost cells). We thus extended our immunofluorescence assays to include HuR and observed that only in the presence of an ERK2 inhibitor (i.e. in cells with active MAP2K1), is HIV-1 able to sequester HuR in the nucleus. Notably, the addition of either inhibitor led to apoptosis of infected cells, consistent with the quantitative RT-PCR data (FIG. 42). These findings support the hypothesis that HIV-1 requires ERK2 for integration but has evolved an additional strategy to secure the prosurvival pathway post-integration, probably via MAP2K1. Thus HIV-1 requires activated ERK2 to integrate as well as to ensure cytoplasmic accumulation of hnRNP-K. As ERK2 is specifically phosphorylated by MAP2K1, HIV-1 also requires activated MAP2K1. Given that lincRNA-p21 in a complex with hnRNP-K shuts down expression of MAP2K1, by targeting the epistatic host protein, MAP2K1, HIV-1 is able to prevent nuclear hnRNP-K and apoptosis post-integration by maintaining MAP2K1 signaling.

Nutlin3a Confirms Pivotal Role of hnRNP-K in Apoptosis Evasion by HIV-1

To confirm our MAP2K1/ERK2 findings and conclusively demonstrate that cytoplasmic accumulation of hnRNP-K plays a central role in the mechanism HIV-1 uses to evade apoptosis, we interrogated the pathway by using drugs that regulate hnRNP-K activity in response to DNA damage and p53-mediated apoptosis. We designed an experiment by which we would restore hnRNP-K to the nucleus during HIV-1 infection and concurrently boost lincRNA-p21 levels. We reasoned that overcoming this block would help to re-establish hnRNP-K's interaction with lincRNA-p21 and trigger cellular apoptosis in infected cells. DNA damage signaling culminates in hnRNP-K activation chiefly through inhibition of its ubiquitin-mediated degradation by the E3 ligase HDM2. Both p53 and hnRNP-K are thus activated in response to DNA damage and both are negatively regulated through the action of HDM2. Nutlin3a is a small molecule inhibitor that activates p53 by binding to HDM2. As Nutlin3a had previously been linked to activation of hnRNP-K, we hypothesised that treatment with this inhibitor may allow hnRNP-K to move into the nucleus of HIV-infected cells (FIG. 43). Control cells treated with Nutlin3a in the absence of any DNA damage showed no nuclear hnRNP-K (FIG. 44 bottom panel) revealing that even if the negative regulation mediated by HDM2 is released, DNA damage is still required to trigger nuclear localisation of hnRNP-K. In contrast, Nutlin3a treatment following 24 hours of infection resulted in nuclear localisation of hnRNP-K in HIV-infected cells only (FIG. 44 upper panel). This result demonstrates that the addition of Nutlin3a after infection is sufficient to prevent the virus from excluding hnRNP-K from the nucleus. Further demonstrating the highly focused viral attack on hnRNP-Khnrnpk nuclear localization.

Though Nutlin3a treatment could lead to nuclear localisation of hnRNP-K in the presence of HIV-1, we sought to combine this effect with elevated lincRNA-p21 expression. Since HIV-1 infection lowers lincRNA-p21 levels by HuR-mediated degradation (FIGS. 34 and 35), overcoming the nuclear exclusion of hnRNP-K is insufficient to induce apoptosis if lincRNA-p21 levels are not concomitantly upregulated. We had previously observed that overexpressed lincRNA-p21 did not lead to apoptosis in HIV-infected cells (FIG. 36) and further determined that there was no nuclear localisation of hnRNP-K in these cells. We then sought to verify that the combination of overexpressed lincRNA-p21 and Nutlin3a in the absence of HIV-1 did not lead to nuclear localisation of hnRNP-K and apoptosis. We transfected cells for 24 hours with either the full-length or truncated lincRNA-p21 sequences followed by the addition of Nutlin3a and observed cytoplasmic hnRNP-K and no apoptosis under both conditions. Finally, we transfected cells for 24 hours with either the full-length or truncated lincRNA-p21 sequences, infected for 24 hours, followed by Nutlin3a treatment. In the presence of the full-length lincRNA-p21 construct only, HIV-infected cells treated with Nutlin3a showed nuclear hnRNP-K and underwent apoptosis (FIG. 45). Similarly treated cells that received the truncated version of lincRNA-p21, which is unable to bind hnRNP-K, also showed nuclear hnRNP-K but did not undergo apoptosis (FIG. 45). Together, these results indicate that restoring nuclear hnRNP-K in the presence of elevated levels of full-length lincRNA-p21 leads to apoptosis in HIV-infected cells. Underlining the pivotal role that the long non coding RNA plays in HIV apoptosis evasion mechanisms.

DISCUSSION

Our findings demonstrate the deliberate and focused attack HIV-1 aims at lincRNA-p21 to mask IN-induced DSBs and evade cellular apoptosis (FIG. 26 to 32). The virus does so by hijacking cellular HuR to degrade lincRNA-p21, and cripples its association with the nuclear protein binding partner hnRNP-K by spatially separating the two molecules (FIG. 33 to 39). HIV-1 ensures nuclear accumulation of hnRNP-K via the previously demonstrated but until now poorly understood action of MAP2K1 and ERK2 (FIG. 40 to 42). Appropriate interaction between lincRNA-p21 and hnRNP-K can be restored through the inhibition of MAP2K1 or ERK2 (FIG. 40 to 42), or via the combined action of Nutlin3a and overexpressed lincRNA-p21 (FIG. 43 to 45). We propose a model (FIG. 46) in which HIV-1 secures the prosurvival pathway by ensuring activated MAP2K1 continues to phosphorylate ERK2 thereby leading to cytoplasmic accumulation of hnRNP-K as well as phosphorylation of HDM2. The latter action of ERK2 ensures ubiquitin-mediated degradation of nuclear hnRNP-K as well as p53. In addition, HIV-1 integration does not lead to complete p53 activation, specifically phosphorylation of Ser46 (FIG. 26 to 32), and thus transcription of proapoptotic lincRNA-p21, and inactivation of prosurvival MAP2K1, is suppressed. Furthermore, by physically altering the location of both of lincRNA-p21's protein binding partners (HuR and hnRNP-K), HIV-1 is able to control cellular apoptosis. Overexpression of lincRNA-p21 and addition of MAP2K1/ERK2 inhibitors or Nutlin3a in the presence of infection support this hypothesis (FIG. 40 to 45). These findings also highlight that three discrete but tightly coordinated events are required for apoptosis to occur. Firstly, DNA damage such as DSBs must lead to complete activation of p53 such that downstream transcription of associated targets is initiated. Secondly, lincRNA-p21 expression levels must be enhanced. This is connected to p53 activation and HuR-mediated degradation but can be bypassed through exogenous overexpression. Third and lastly, hnRNP-K must translocate to the nucleus to ensure its association with lincRNA-p21 and subsequent suppression of prosurvival genes such as MAP2K1. An absence of any one of these events is sufficient for the evasion of apoptosis as summarised by our findings.

While it is not unusual for pathogens to manipulate host signaling pathways, our data illuminate a unique strategy whereby HIV-1 is able to control the cellular response to DNA damage via a long noncoding RNA. It has been observed that Adenovirus oncoproteins are able to inactivate the DNA repair MRN complex at viral replication centers, masking host genome instabilities that are instigated by this generally non-integrative DNA virus. The phosphorylation of p53 at key residues, required to ensure its stabilization as well as to facilitate DNA binding, is also inhibited in adenovirus-infected cells. Intriguingly, in the presence of exogenous genotoxic stress, p53 was phosphorylated at multiple residues and thus stabilized to a greater extent than untreated cells, but the presence of adenovirus ensured that p53 failed to activate downstream transcription. As the constitutive expression of p53 in the absence of DNA damage is controlled through HDM2-mediated degradation, the phosphorylation of p53 is synonymous with its resistance to such degradation and transcription of downstream effectors. Given that viruses contribute to 20% of cancers worldwide, it is important to understand how genomic instabilities are propagated following challenge, as well as how apoptosis is evaded. While HIV-1 itself does not cause cancer, our observations that HIV-mediated resistance to apoptosis occurs through manipulation of a host long noncoding RNA and its protein binding partners, reveals a novel mechanism whereby genomic integrity can be severely challenged yet cells survive. Thus HIV-1 may be an informative tool in the study of human malignancies.

Finally, our data provide a glimpse of how pathogens with limited coding capacity can significantly restructure major cellular pathways using host lncRNAs. This is even more striking in the context of cell-specific transcription: activated CD4+ T cells express low levels of MAP2K1/ERK2, and are highly sensitive to HIV-induced apoptosis. In contrast, MAP2K1/ERK2 expression remains high in macrophages, and these cells resist viral-induced apoptosis. MAP2K1 and lincRNA-p21 are at the nexus of these pathways and their manipulation by HIV-1 adds a new layer of complexity to host-pathogen interactions.

The invention claimed is:

1. A method for inducing apoptosis in a cell infected with Human Immunodeficiency Virus (HIV), the method comprising:
    elevating levels of full-length lincRNA-p21 in the cell by activating the transcription of lincRNA-p21 in the cell or by transfecting the cell with full-length lincRNAp21; and
    inducing localisation of hnRNP-K to the nucleus of the cell by inhibiting HDM2, MAP2K1 or ERK2;
        wherein in response to a double stranded break in the cell's DNA, caused by the infection with the HIV, lincRNA-p21 associates with hnRNP-K in the nucleus and induces apoptosis in the cell.

2. The method of claim 1, wherein the cell is treated with (−)-4-(4,5-Bis(4-chlorophenyl)-2-(2-isopropoxy-4-methoxyphenyl)-4,5-dihydro-1H-imidazole-1-carbonyl) piperazin-2-one, and wherein the (−)-4-(4,5-Bis(4-chlorophenyl)-2-(2-isopropoxy-4-methoxyphenyl)-4,5-dihydro-1H-imidazole-1-carbonyl)piperazin-2-one binds to and inhibits HDM2.

3. The method of claim 1, wherein inhibition of HDM2 by the inhibitor results in the release of the negative regulation of hnRNP-K, which induces localisation of hnRNP-K to the nucleus.

4. The method of claim 1, wherein the elevating levels of full-length lincRNA-p21 in the cell is by activating the transcription of lincRNA-p21 in the cell.

5. The method of claim 1, wherein the elevating levels of full-length lincRNA-p21 in the cell is by transfecting the cell with full-length lincRNAp21.

* * * * *

SEQUENCE LISTING

```
<160> NUMBER OF SEQ ID NOS: 18

<210> SEQ ID NO 1
<211> LENGTH: 19
<212> TYPE: RNA
<213> ORGANISM: Homo sapiens

<400> SEQUENCE: 1
gacaaaaucu uacagguuu                                                   19

<210> SEQ ID NO 2
<211> LENGTH: 19
<212> TYPE: RNA
<213> ORGANISM: Homo sapiens

<400> SEQUENCE: 2
gacauguucu cucgguuug                                                   19

<210> SEQ ID NO 3
<211> LENGTH: 19
<212> TYPE: RNA
<213> ORGANISM: Homo sapiens

<400> SEQUENCE: 3
acaaauaacu cgcucaugc                                                   19

<210> SEQ ID NO 4
<211> LENGTH: 19
<212> TYPE: RNA
<213> ORGANISM: Homo sapiens

<400> SEQUENCE: 4
gcucagaggu gaucaaaga                                                   19

<210> SEQ ID NO 5
<211> LENGTH: 20
<212> TYPE: DNA
```

```
<213> ORGANISM: Homo sapiens

<400> SEQUENCE: 5
tgacacgctt ccctggattg                                               20

<210> SEQ ID NO 6
<211> LENGTH: 20
<212> TYPE: DNA
<213> ORGANISM: Homo sapiens

<400> SEQUENCE: 6
accatcgcta tctgagcagc                                               20

<210> SEQ ID NO 7
<211> LENGTH: 20
<212> TYPE: DNA
<213> ORGANISM: Homo sapiens

<400> SEQUENCE: 7
agtcagttcc ttgtggagcc                                               20

<210> SEQ ID NO 8
<211> LENGTH: 20
<212> TYPE: DNA
<213> ORGANISM: Homo sapiens

<400> SEQUENCE: 8
aggagaacac gggatgagga                                               20

<210> SEQ ID NO 9
<211> LENGTH: 20
<212> TYPE: DNA
<213> ORGANISM: Homo sapiens

<400> SEQUENCE: 9
tagccatctg tgcccactct                                               20

<210> SEQ ID NO 10
<211> LENGTH: 20
<212> TYPE: DNA
<213> ORGANISM: Homo sapiens

<400> SEQUENCE: 10
gctccacact ccacactacc                                               20

<210> SEQ ID NO 11
<211> LENGTH: 20
<212> TYPE: DNA
<213> ORGANISM: Human immunodeficiency virus type 1

<400> SEQUENCE: 11
ggccttcagc ccagaagtaa                                               20

<210> SEQ ID NO 12
<211> LENGTH: 20
<212> TYPE: DNA
<213> ORGANISM: Human immunodeficiency virus type 1

<400> SEQUENCE: 12
ctttatggct gggtcctccc                                               20

<210> SEQ ID NO 13
<211> LENGTH: 20
```

```
<212> TYPE: DNA
<213> ORGANISM: Homo sapiens

<400> SEQUENCE: 13
cagggaaccc cttcaatccc                                              20

<210> SEQ ID NO 14
<211> LENGTH: 20
<212> TYPE: DNA
<213> ORGANISM: Homo sapiens

<400> SEQUENCE: 14
tttttgccca catgagcctg                                              20

<210> SEQ ID NO 15
<211> LENGTH: 20
<212> TYPE: DNA
<213> ORGANISM: Homo sapiens

<400> SEQUENCE: 15
agagcgatca acacgctgaa                                              20

<210> SEQ ID NO 16
<211> LENGTH: 20
<212> TYPE: DNA
<213> ORGANISM: Homo sapiens

<400> SEQUENCE: 16
taaacgcaac ccctctggac                                              20

<210> SEQ ID NO 17
<211> LENGTH: 21
<212> TYPE: DNA
<213> ORGANISM: Homo sapiens

<400> SEQUENCE: 17
gcagccctgg cgtcgtgatt a                                            21

<210> SEQ ID NO 18
<211> LENGTH: 22
<212> TYPE: DNA
<213> ORGANISM: Homo sapiens

<400> SEQUENCE: 18
cgtggggtcc ttttcaccag ca                                           22
```